(12) United States Patent
Bashir et al.

(10) Patent No.: US 9,376,713 B2
(45) Date of Patent: Jun. 28, 2016

(54) LABEL FREE DETECTION OF NUCLEIC ACID AMPLIFICATION

(75) Inventors: Rashid Bashir, Champaign, IL (US); Yi-Shao Liu, Champaign, IL (US); Eric Salm, Champaign, IL (US); Woo-Jin Chang, Urbana, IL (US); Nicholas N. Watkins, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 779 days.

(21) Appl. No.: 12/888,917

(22) Filed: Sep. 23, 2010

(65) Prior Publication Data

US 2011/0086352 A1    Apr. 14, 2011

Related U.S. Application Data

(60) Provisional application No. 61/245,083, filed on Sep. 23, 2009.

(51) Int. Cl.
| | | |
|---|---|---|
| C12Q 1/68 | (2006.01) | |
| B01L 3/00 | (2006.01) | |
| B01L 7/00 | (2006.01) | |
| B03C 5/02 | (2006.01) | |
| B01L 3/02 | (2006.01) | |

(52) U.S. Cl.
CPC ........... *C12Q 1/6825* (2013.01); *B01L 3/5027* (2013.01); *B01L 3/502784* (2013.01); *B01L 7/52* (2013.01); *B03C 5/026* (2013.01); *B01L 3/0241* (2013.01); *B01L 3/502746* (2013.01); *B01L 3/502761* (2013.01); *B01L 2200/0668* (2013.01); *B01L 2200/10* (2013.01); *B01L 2200/143* (2013.01); *B01L 2200/147* (2013.01); *B01L 2300/0645* (2013.01); *B01L 2300/0681* (2013.01); *B01L 2300/0867* (2013.01); *B01L 2300/1822* (2013.01); *B01L 2300/1827* (2013.01); *B01L 2400/0418* (2013.01); *B01L 2400/0424* (2013.01); *B01L 2400/084* (2013.01)

(58) Field of Classification Search
None
See application file for complete search history.

(56) References Cited

U.S. PATENT DOCUMENTS

| | | | |
|---|---|---|---|
| 5,795,782 A | 8/1998 | Church et al. | |
| 6,015,714 A | 1/2000 | Baldarelli et al. | |
| 6,267,872 B1 | 7/2001 | Akeson et al. | |
| 6,325,904 B1 | 12/2001 | Peeters | |
| 6,355,431 B1 | 3/2002 | Chee et al. | |
| 6,426,231 B1 | 7/2002 | Bayley et al. | |
| 6,428,959 B1 | 8/2002 | Deamer | |
| 6,465,193 B2 | 10/2002 | Akeson et al. | |
| 6,617,113 B2 | 9/2003 | Deamer | |
| 6,627,067 B1 | 9/2003 | Branton et al. | |
| 6,746,594 B2 | 6/2004 | Akeson et al. | |
| 6,824,659 B2 | 11/2004 | Bayley et al. | |
| 6,916,665 B2 | 7/2005 | Bayley et al. | |
| 6,927,070 B1 | 8/2005 | Bayley et al. | |
| 6,977,171 B1 | 12/2005 | Dennis et al. | |
| 7,015,701 B2 | 3/2006 | Wiegand et al. | |
| 7,060,507 B2 | 6/2006 | Akeson et al. | |
| 7,122,152 B2 | 10/2006 | Lewis et al. | |
| 7,135,294 B2 | 11/2006 | Lee et al. | |
| 7,157,232 B2 * | 1/2007 | Miles et al. | 506/39 |
| 7,189,503 B2 | 3/2007 | Akeson et al. | |
| 7,195,780 B2 | 3/2007 | Dennis et al. | |
| 7,238,485 B2 | 7/2007 | Akeson et al. | |
| 7,258,838 B2 | 8/2007 | Li et al. | |
| 7,259,019 B2 | 8/2007 | Pawliszyn et al. | |
| 7,385,267 B2 | 6/2008 | Liber et al. | |
| 7,393,644 B2 | 7/2008 | Lee et al. | |
| 7,452,669 B2 | 11/2008 | Kim et al. | |
| 2002/0072054 A1 * | 6/2002 | Miles et al. | 435/6 |
| 2004/0136866 A1 | 7/2004 | Pontis et al. | |
| 2005/0032100 A1 | 2/2005 | Heath et al. | |
| 2005/0995698 | 5/2005 | Carlson | |
| 2005/0127035 A1 | 6/2005 | Ling | |
| 2005/0208574 A1 | 9/2005 | Bayley et al. | |
| 2006/0063171 A1 | 3/2006 | Akeson et al. | |
| 2006/0228723 A1 | 10/2006 | Bradley et al. | |
| 2007/0042366 A1 | 2/2007 | Ling | |
| 2007/0114573 A1 | 5/2007 | Han et al. | |
| 2007/0132043 A1 | 6/2007 | Bradley et al. | |

(Continued)

FOREIGN PATENT DOCUMENTS

| | | |
|---|---|---|
| EP | 1225234 | 11/2007 |
| WO | 2008/070058 | 6/2008 |

(Continued)

OTHER PUBLICATIONS

Hodio et al. (Proc. SPIE, 2001, vol. 4265, p. 65-74).*

(Continued)

*Primary Examiner* — Stephanie K Mummert
(74) *Attorney, Agent, or Firm* — Lathrop & Gage LLP

(57) ABSTRACT

Provided are methods and devices for label-free detection of nucleic acids that are amplified by polymerase chain reaction. A solution containing the components necessary for a PCR is introduced to a microfluidic amplification chamber and an electric field applied to a confined region in which PCR occurs. PCR product generated in the confined region is detected by measuring an electrical parameter that is, for example, solution impedance. The devices and methods provided herein are used, for example, in assays to detect one or more pathogens or for point-of-care tests. In an aspect, the PCR product is confined to droplets and the assay relates to detecting an electrical parameter of a flowing droplet, thereby detecting PCR product without a label. In an aspect, the PCR occurs in the droplet.

41 Claims, 28 Drawing Sheets

(56) References Cited

U.S. PATENT DOCUMENTS

| | | |
|---|---|---|
| 2007/0190542 A1 | 8/2007 | Ling et al. |
| 2007/0235760 A1 | 10/2007 | Shim et al. |
| 2008/0025875 A1 | 1/2008 | Martin et al. |
| 2008/0280776 A1 | 11/2008 | Bashir et al. |
| 2012/0021918 A1 | 1/2012 | Bashir et al. |

FOREIGN PATENT DOCUMENTS

| | | |
|---|---|---|
| WO | 2010/037085 | 4/2010 |
| WO | 2011/163058 | 12/2011 |
| WO | 2012/078340 | 6/2012 |

OTHER PUBLICATIONS

Beer et al. (Anal Chem, 2007, vol. 79, p. 8471-8475).*
Zhao et al. (SPIE, 2002, 4936, p. 321-326).*
Chang et al. (Biomedical Microdevices, 2003, 5(4):281-290).*
Yun et al., (Proc of SPIE, 2006, 6172, Abstract).*
Sista et al. (Lab on Chip, 2008, vol. 8, p. 2091-2104).*
Chang et al. (Biomed Microdevices, 2006, vol. 8, p. 215-225).*
International Search Report and Written Opinion, Corresponding to International Application No. PCT/US2009/058739, Mailed Nov. 19, 2009, 11 pp.
International Search Report and Written Opinion, Corresponding to International Application No. PCT/US07/24804, Mailed Apr. 3, 2008, 6 pp.
Akin et al. (2007) "Bacterial Mediated Delivery of Nanoparticles and Cargo into Cells," Nature Nanotechnol. 149(2):441-449.
Bajaj et al. (Published online May 2007) "Ultrananocrystalline Diamond Film as an Optimal Cell Interface for Biomedical Applications," Biomed. Microdev. 9:787-794.
Baker-Jarvis et al. (1998) "Electrical Properties and Dielectric Relaxation of DNA in Solution," NIST Technical Note 1509, 70 pp.
Banada et al. (2006) "Performance Evaluation of a Low Conductive Growth Medium (LCGM) for Growth of Healthy and Stressed *Listeria monocytogenes* and Other Common Bacterial Species," Int. J. Food Microbiol 111:12-20.
Baranski, A. (2002) "Hot Microelectrodes," Anal. Chem. 74:1294-1301.
Bashir, R. (Online article accepted May 15, 2004) "BioMEMS: State-of-the-Art in Detection, Opportunities and Prospects," Adv. Drug Deliv. Rev., 22 pp.
Bashir, R. (Sep. 23, 2008) "Silicon Based Nanosensors for Biology and Medicine," AIChE Midwest Regional Conference, 59 pp.
Belgrader et al. (Apr. 16, 1999) "PCR Detection of Bacteria in Seven Minutes," Science 284:449-450.
Berdat et al. (Oct. 25, 2006) "DNA Biosensor Using Fluorescence Microscopy and Impedance Spectroscopy," Sensors and Actuators B, 118(1-2):53-59.
Bhattacharya et al. (2008) "PCR-Based Detection in a Micro-Fabricated Platform," Lab on a Chip 8:1130-1136.
Bhattacharya et al. (2007) "BioMEMS and Nanotechnology-Based Approaches for Rapid Detection of Biological Entities," J Rapid Methods Automation Microbiol. 15:1-32.
Cady et al. (2005) "Real-Time PCR Detection of *Listeria monocytogenes* Using and Integrated Microfluidics Platform," Sensors Actuators B 107:332-341.
Chang et al. (2004) "DNA-Mediated Fluctuations in Ionic Current through Silicon Oxide Nanopore Channels," Nano Letters 4(8):1551-1556.
Chang et al. (2006) "Fabrication and Characterization of Solid State Nanopores Using Field Emission Scanning Electron Microscope," Appl. Phys. Lett. 88:103109, 3 pp.
Chang et al. (Sep. 2006) "DNA Counterion Current and Saturation Examined by a MEMS-Based Solid State Nanopore Sensor," Biomedical MicroDevices 8(3):263-269.
Chang et al. (2003) "Poly(dimethlsiloxane) (PDMS) and Silicon Hybrid Biochip for Bacterial Culture," Biomed. Microdev. 5(4):281-290.
Chen et al. (1996) "Identification and Differentiation of *Mycobacterium Avium* and *M. intreacellulare* by PCR," J. Clin. Microbiol. 34(5):1267-1269.
Cheng et al. (Jun. 2007) "Cell Detection and Counting Through Cell Lysate Impedance Spectroscopy in Microfluidic Devices," Lab on a Chip 7:746-755.
Choi et al. (2007) "A Cellular Trojan Horse for Delivery of Therapeutic Nanoparticles into Tumors," Nanolett. 7(12):3759-3765.
Chrisey et al. (1996) "Covalent Attachment of Synthetic DNA to Self-Assembled Monolayer Films," Nuc. Acids Res 24(15):3031-3039.
Cui et al. (2001) "Electrothermal Modeling of Silicon PCR Chips," Proceedings of SPIE 4407:275-280.
El-Ali et al. (2004) "Simulation and Experimental Validation of a SU-8 Based PCR Thermocycler Chip with Integrated Heaters and Temperature Sensor," Sensors and Actuators A 110:3-10.
Elibol et al. (May 2007) "Selective Heating Characterization of Nanoplate Devices for Sensing Applications," NSTI-Nanotech 2007, Santa Clara, CA 2:198-201.
Elibol et al. (2009) "Localized Heating on Silicon Field Effect Transistors: Device Fabrication and Temperature Measurements in Fluid," Lab on a Chip 9(19):2789-2795.
Elibol et al. (2008) "Localized Heating and Thermal Characterization of High Electrical Resistivity Silicon-on-Insulator Sensors Using Nematic Liquid Crystals," Appl. Phys. Lett. 93(13):131908, 3pp.
Elibol et al. (Dec. 1, 2003) "Integrated Nanoscale Silicon Sensors Using Top-Down Fabrication," Appl. Phys. Lett. 83(22):4613-4615.
Fologea et al. (2005) "Slowing DNA Translocation in a Solid-State Nanopore," Nano Lett. 5(9):1734-1737.
Fritz et al. (Oct. 29, 2002) "Electronic Detection of DNA by its Intrinsic Molecular Charge," Proc. Nat. Acad. Sci. USA 99(22):14142-14146.
Gomez et al. (2002) "Microscale Electronic Detection of Bacterial Metabolism," Sensors and Actuators B 86:198-208.
Gomez-Sjoberg et al. (2005) "Impedance Microbiology-on-a-Chip: Microfluidic Bioprocessor for Rapid Detection of Bacterial Metabolism," IEEE/ASME Journal of Microelectromechanical Syst. 14(4):829-838.
Gu et al (Apr. 22, 1999) "Stochastic Sensing of Organic Analytes by a Pore-Forming Protein Containing a Molecular Adapter," Nature 398:686-690.
Guiducci et al. (Oct. 2006) "Microelectrodes on a Silicon Chip for Label-Free Capacitive DNA Sensing," IEEE Sensors J. 6(5):1084-1093.
Gupta et al. (Mar. 15, 2004) "Single Virus Particle Mass Detection Using Microresonators with Nanoscale Thickness," Appl. Phsy. Lett. 84(11):1976-1978.
Gupta et al. (Sep. 2006) "Anomalous Resonance in a Nanomechanical Biosensor," Proc. Nat. Acad. Sci. USA 103(36):13362-13367.
Hanss et al. (Sep. 1973) "Dielectric Relaxation and Orientation of DNA Molecules," Biopolymers 12(9):2151-2159.
Hashimoto et al. (Apr. 15, 2006) "Polymerase Chain Reaction/Ligase Detection Reaction/Hybridization Assays Using Flow-Through Microfluidic Devices for the Detection of Low-Abundant DNA Point Mutations," Biosens and Bioelectron 21(10):1915-1923.
Hong et al. (2004) "A Dielectric Biosensor Using the Capacitance Change with AC Frequency Integrated on Glass Substrates," Japan. J. of Applied Physics 43(8A):5639-5645.
Hou et al. (2007) "Integrated Microelectronic Device for Label-Free Nucleic Acid Amplification and Detection," Lab on a Chip 7:347-354.
Howorka et al. (2001) "Sequence-Specific Detection of Individual DNA Strands Using Engineered Nanopores," Nature Biotechnol. 19:636-639.
Huang et al. (2006) "An Integrated Microfluidic Chip for DNA/RNA Amplification, Electrophoresis Separation and On-Line Optical Detection," Electrophoresis 27:3297-3305.
Huang et al. (2006) "Surface-Directed Boundary Flow in Microfluidic Channels," Langmuir 22(14):6429-6437.
Iqbal et al. (Web Release Apr. 1, 2007) "Solid-State Nanopore Channels with DNA Selectivity," Nature Nanotechnol, plus Supplementary Online Material, 25 pp.

(56) References Cited

OTHER PUBLICATIONS

Johnson et al. (2006). "Characterization of vaccinia Virus Particles Using Microscale Silicon Cantilever Resonators and Atomic Force Microscopy," Sensors and Actuators B-Chemical 115(1):189-197.

Jungner et al. (May 28, 1949) "Molecular Weight Determination no Thymonucleic Acid Compounds by Dielectric Measurements," Nature 163(4152):849-850.

Kajiyama et al. (2003) "Genotypnig on a Thermal Gradient DNA Chip," Genome Res.13:467-475.

Kasianowicz et al. (Nov. 1996) "Characterization of Individual Polynucleotide Molecules Using a Membrane Channel," Proc. Nat. Acad. Sci. USA 93:13770-13773.

Kasianowicz et al. (2006) "Enhancing Molecular Flux Through Nanopores by Means of Attractive Interactions," Proc. Nat. Acal Sci. USA 103(31):11431-11432.

Katz et al. (2003) "Probing Bimolecular Interactions at Conductive and Semiconductive Surfaces by Impedance Spectroscopy: Routes to Impedimetric Immunosensors, DNA-Sensors, and Enzyme Biosensors," Electroanalysis 15(11):913-947.

Ke et al. (2007) "Single Step Cell Lysis/PCR Detection of *Escherichia coli* in an Independently Controllable Silicon Microreactor," Sensors Actuators B 120:538-544.

Khandurina et al. (Jul. 2000) "Integrated System for Rapid PCR-Based DNA Analysis in Microfluidic Devices," Anal. Chem. 72:2995-3000.

Kohli et al. (Aug. 13, 2004) "DNA-Functionalized Nanotube Membranes with Single-Base Mismatch Selectivity," Science 305:984-986.

Kulski et al. (1995) "Use of a Multiplex PCR to Detect and Identify *Mycobacterium avium* and *M. intracellulare* in Blood Culture Fluids of AIDS Patients," J. Clin. Microbiol. 33(3):668-674.

Lagally et al. (Feb. 2001) "Single-Molecule DNA Amplification and Analysis in an Integrated Microfluidic Device," Anal. Chem. 73:565-570.

Lee et al. (2003) "Dielectrophoresis and Electrohydrodynamics-Mediated Fluidic Assembly of Silicon Resistors," Appl. Phys. Lett. 83(18):3833-3835.

Li et al. (Feb. 2005) "Characterization and Modeling of a Microfluidic Dielectrophoresis Filter for Biological Species," J. Microelectromech. Syst. 14(1):103-112.

Li et al. (Jul. 12, 2001) "Ion-Beam Sculpting at Nanometre Length Scales," Nature 412:166-169.

Li et al. (2002) "Dielectrophoretic Separation and Manipulation of Live and Heat-Treated Cells of *Listeria* on Microfabricated Devices with Interdigitated Electrodes," Sens. Actuators B 86:215-221.

Liao et al. (2005) "Micromachined Polymerase Chain Reaction System for Multiple DNA Amplification of Upper Respiratory Tract Infectious Diseases," Biosens. Bioelectron. 20:1341-1348.

Liu et al. (May 28, 2009) "Label Free Detection of PCR (Polymerase Chain Reaction) Amplification," Presentation given at the; $215^{th}$ ECS Meeting, San Francisco, CA, May 24-29, 33 pp.

Liu et al. (Oct. 2008) "Label Free Detection of PCR Amplification," The $7^{th}$ IEEE Conference on Sensors, Lecce, Italy, Oct. 26-29, pp. 550-553.

Liu et al. (2008) "Electrical Characterization of DNA Molecules in Solution Using Impedance Measurements," Appl. Phys. Lett. 92:143902, 3pp.

Liu et al. (2007) "Electrical Detection of Germination of Model *Bacillus anthracis* Spores in Microfluidic Biochips," Lab on a Chip 7:603-610.

Liu et al. (2008) "Electrical Detection of DNA Molecules," BMES Bulletin 32(3):14-15.

Liu et al. (Oct. 27, 2008) "Label Free Detection of PCR Amplification," $7^{th}$ IEEE Conference on Sensors, Lecce, Italy, 45 pp.

Lopez-Buedo et al. (1998) "Thermal Testing on Programmable Logic Devices," Proc. IEEE ISCAS Conf. 2:240-243.

Lu et al. (2007) "Hexamethyldisilazane-Mediated Controlled Polymerization of α-Amino Amino Acid N-Carboxyanhydrides," J. Am. Chem. Soc. 129:14114-14115.

Meller et al. (Feb. 1, 2000) "Rapid Nanopore Discrimination Between Single Polynucleotide Molecules," Proc. Nat. Acad. Sci. USA 97(3):1079-1084.

Park et al. (2007) "Selective Functionalization of Silicon Micro/Nanowire Sensors via Localized Joule Heating," Proceedings of $2^{nd}$ IEEE-NEMS 2:899-904.

Park et al. (2008) "'Living Cantilever Arrays' for Characterization of Mass of Single Live Cells in Fluids," Lab on a Chip 8:1034-1041.

Pourmand et al. (2006) "Direct Electrical Detection of DNA Synthesis," Proc. Nat. Acad. Sci. USA 103(17):6466-6470.

Reddy et al. (Published online Jan. 4, 2011) "High-k Dielectric $Al_2O_3$ Nanowire and Nanoplate Field Effect Sensors for Improved pH Sensing," Biomed. Microdev. 13:335-344.

Rodriguez et al. (2005) "A Microchip CD4 Counting Method for HIV Monitoring in Resource-Poor Settings" PLoS Med 2(7):e182, pp. 0663-0672.

Sin et al. (2008) "Scaling Analysis of a Universal Electrode for Molecular Biosensors," Proceedings of 3rd IEEE International Conference on Nano/Micro Engineered and Molecular Systems, NEMS, pp. 1151-1155.

Singh et al. (2006) "PCR Thermal Management in an Integrated Lab on Chip," J. Phys Conf. Series 34:222-227.

Steitz, T.A. (1999) "DNA Polymerases: Structural Diversity and Common Mechanisms," J. Biol. Chem. 274(25):17395-17398.

Taylor et al. (Aug. 1, 1997) "Optimization of the Performance of the Polymerase Chain Reaction in Silicon-Based Microstructures," Nucleic Acids Res. 25(15):3164-3168.

Venkatesan et al. (2009) "Highly Sensitive, Mechanically Stable Nanopore Sensors for DNA Analysis," Adv. Materials 21(7):2771-2776.

Wang et al. (2006) "A Disposable Microfluidic Cassette for DNA Amplification and Detection," Lab on a Chip 6(1):46-53.

Waters et al. (1998) "Multiple Sample PCR Amplification and Electrophoretic Analysis on a Microchip," Anal. Chem. 70:5172-5176.

Woolley et al. (Dec. 1996) "Functional Integration of PCR Amplification and Capillary Electrophoresis in a Microfabricated DNA Analysis Device," Anal. Chem.68:4081-4086.

Yamamoto et al. (2002) "Phospholipids Promote Dissociation of ADP from the *Mycobacterium avium* DnaA Protein," J. Biochem. 131(2):219-224.

Yang et al. (Dec. 20, 2005) "Conductivity and pH Dual Detection of Growth Profile of Healthy and Stressed *Listeria monocytogenes*," Biotech. Bioeng. 92(6):685-694.

Yang et al. (2006) "A Multifunctional Micro-Fluidic System for Dielectrophoretic Concentration Coupled with Immuno-Capture of Low Numbers of *Listeria monocytogenes*," Lab on a Chip 6:896-905.

Yi et al. (Jan. 15, 2005) "Theoretical and Experimental Study Towards a Nanogap Dielectric Biosensor," Biosens. Bioelectron 20(7):1320-1326.

Yoon et al. (2002) "Precise Temperature Control and Rapid Thermal Cycling in a Micromachined DNA Polymerase Chain Reaction Chip," J. Micromech. Microeng. 12:813-823.

\* cited by examiner

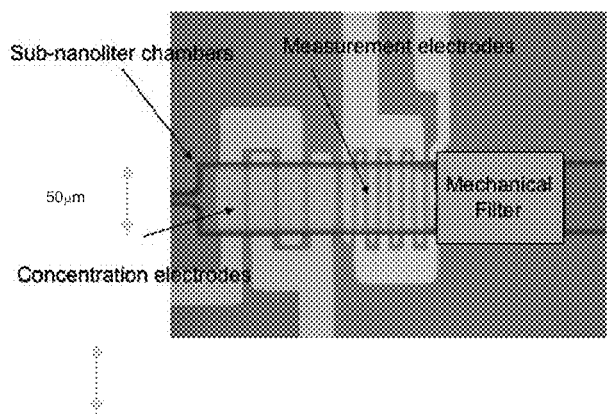 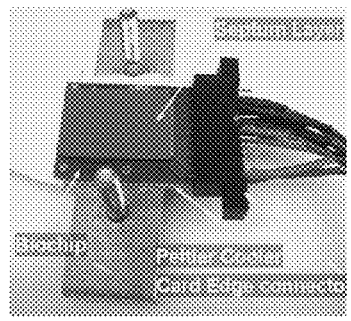
Figure 9A     Figure 9B
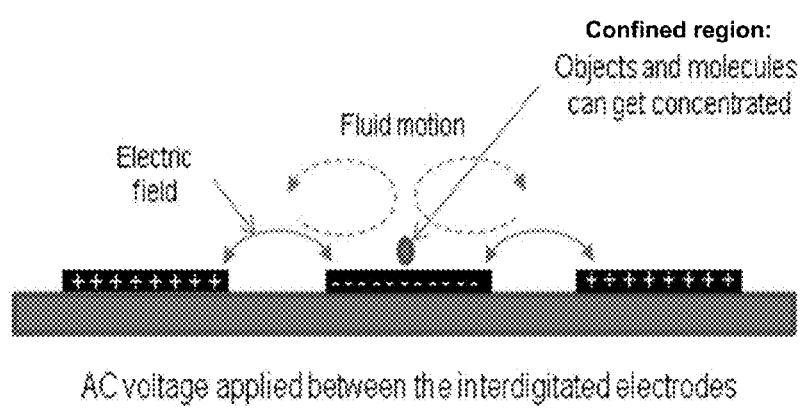
Figure 10

| Material | Electrical Resistivity (Ω·m) |
|---|---|
| DI water | 1.8e5 |
| Mineral Oil | 1.0e8 |
| [BMIM][PF6] | 6.9 |
| PBS | 0.57 |

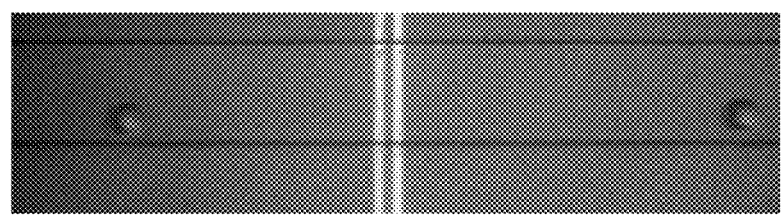
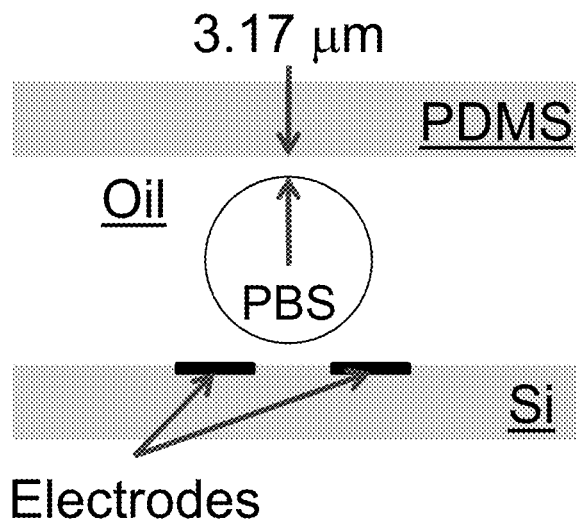
$R_{Oil} >> R_{PBS}$
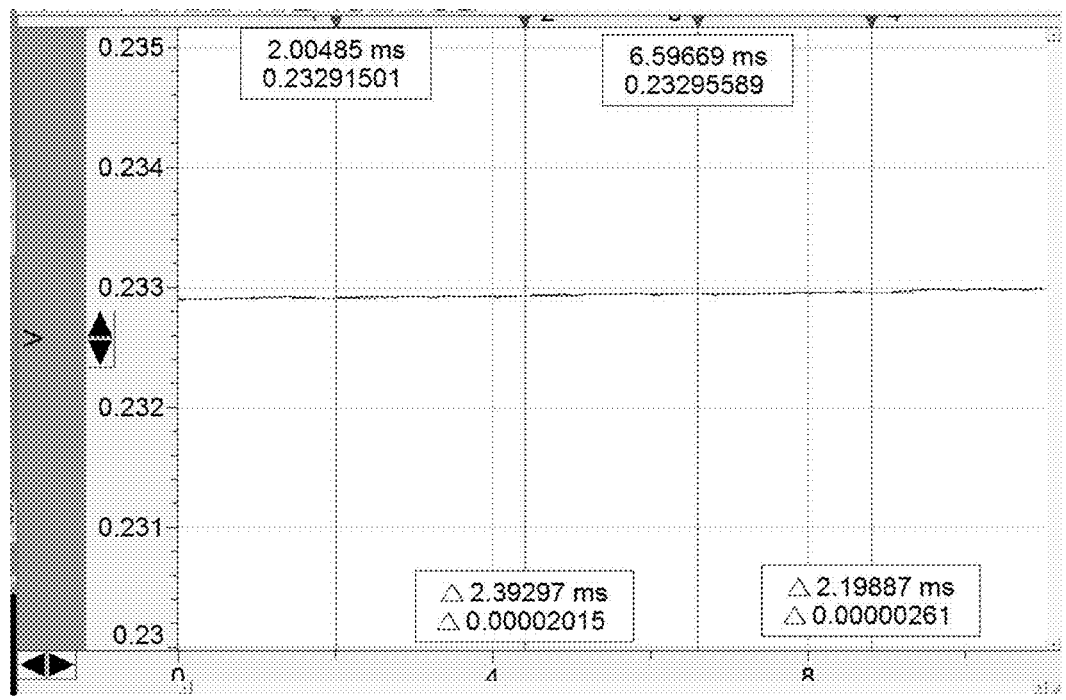
Figure 18

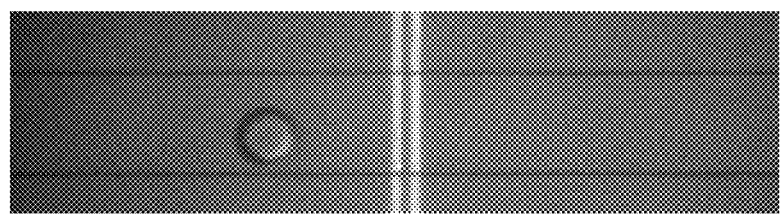
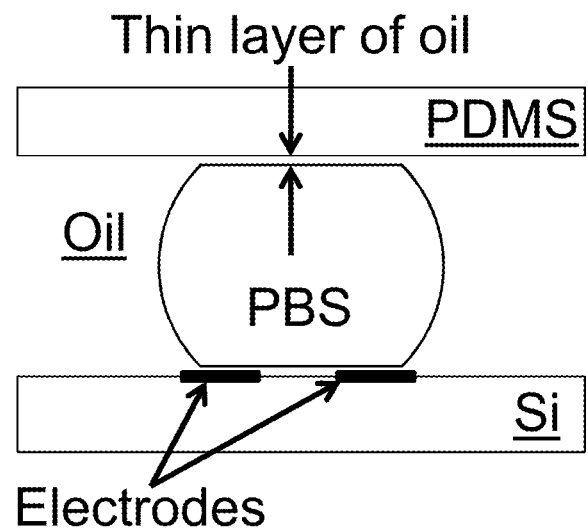
$R_{Oil} >> R_{PBS}$
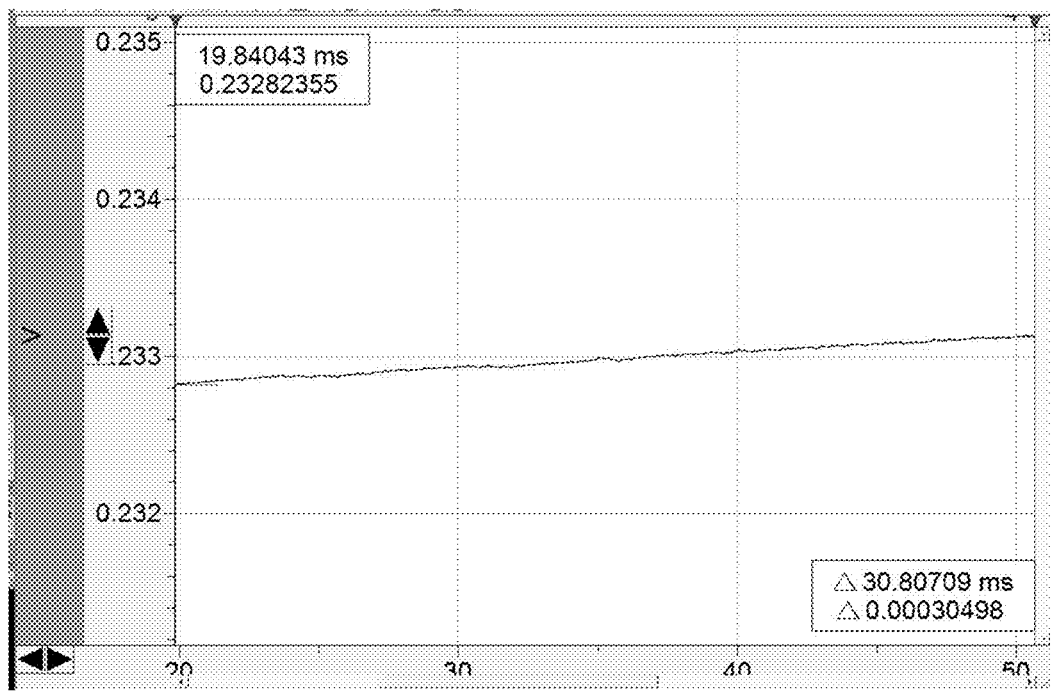
Figure 19

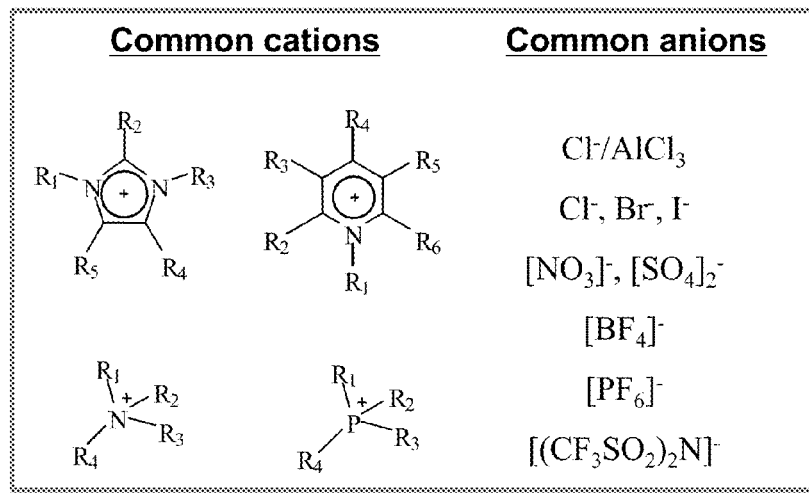
Immidazolium-based ILs
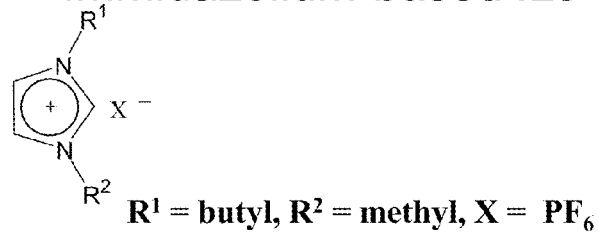
$R^1$ = butyl, $R^2$ = methyl, $X$ = $PF_6$
[bmim]$PF_6$:
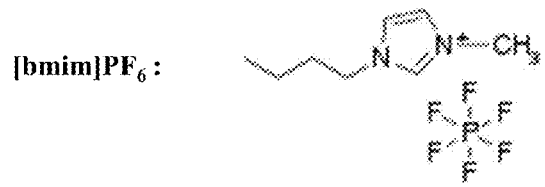
|  | Miscibility with $H_2O$ | M.P. (°C) | Density (gcm$^{-3}$) | Viscosity (cP) (25°C) | Conductivty (S/m) |
|---|---|---|---|---|---|
| [emim][PF$_6$] | ○ | 60 | – | – | – |
| [bmim][PF$_6$] | × | -61 | 1.37 | 272.1 | 0.146 |
| [hmim][PF$_6$] | × | -73.5 | 1.30 | 497 | 0.110 |
Figure 20

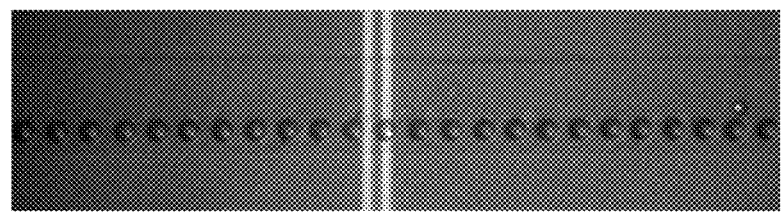
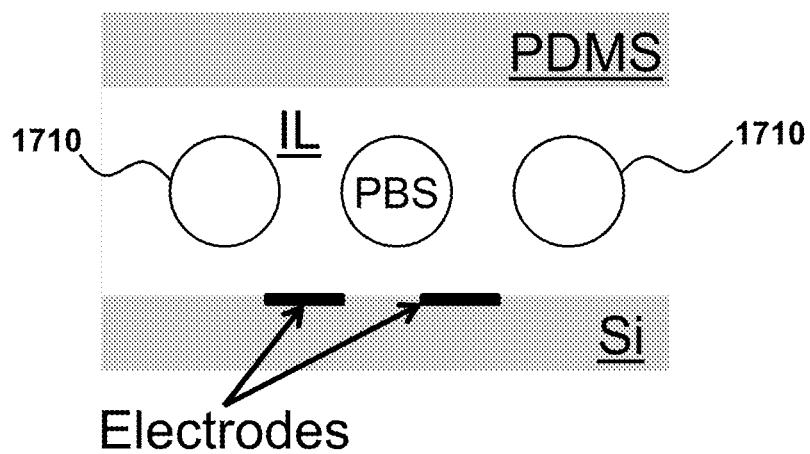
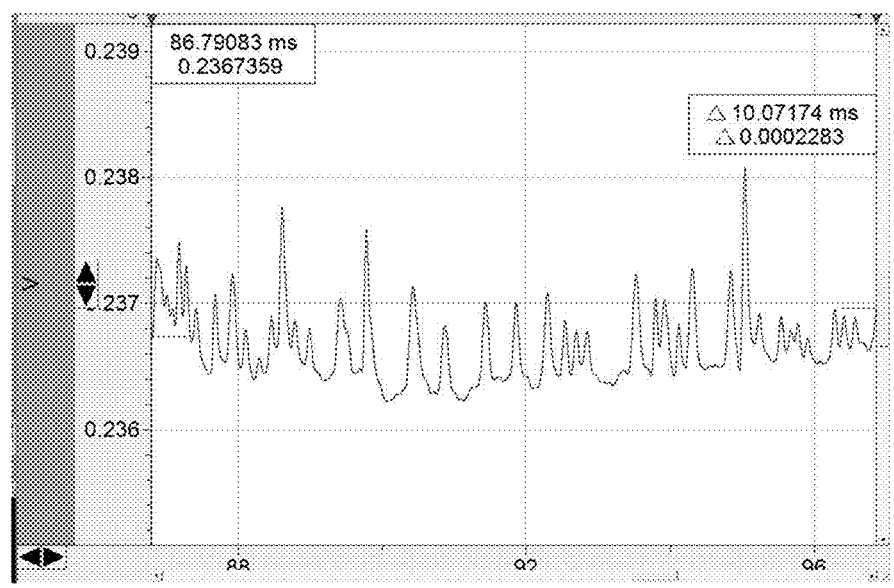
Figure 21

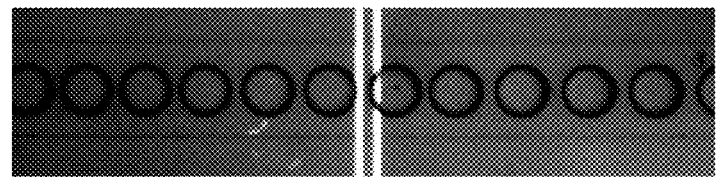
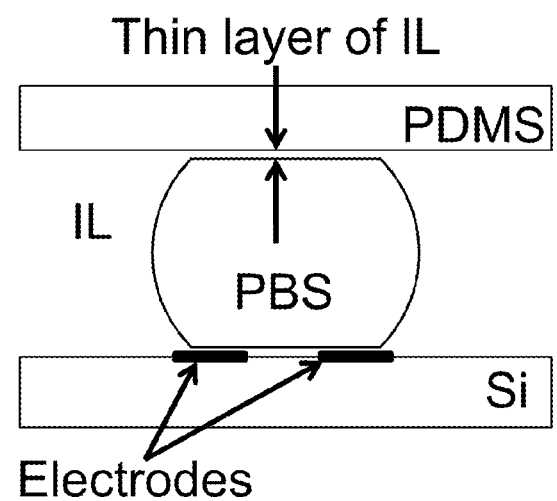
$R_{IL} > R_{PBS}$
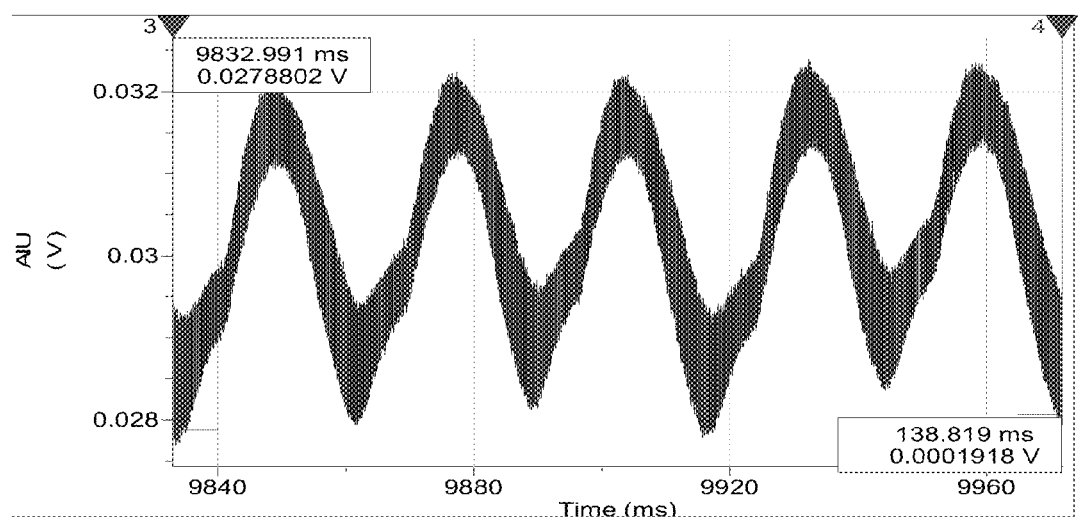
Figure 22

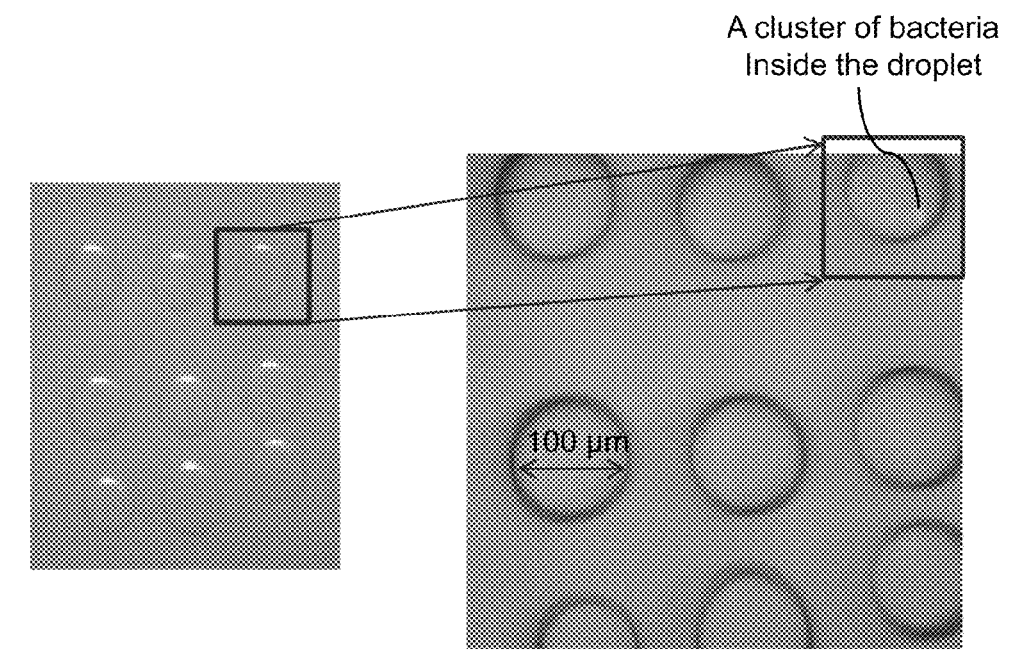
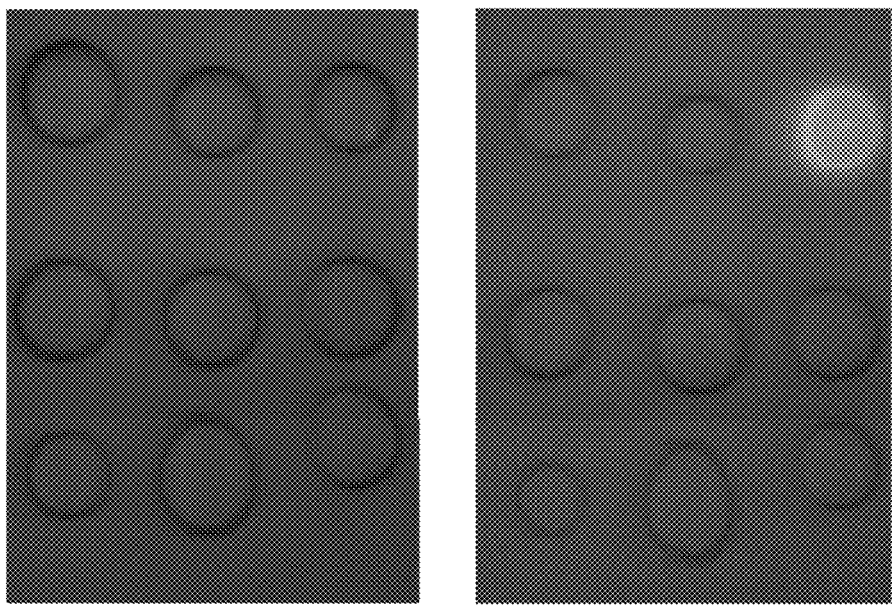
Figure 24

LABEL FREE DETECTION OF NUCLEIC ACID AMPLIFICATION

CROSS-REFERENCE TO RELATED APPLICATIONS

This application claims benefit of U.S. Provisional Patent App. No. 61/245,083 filed Sep. 23, 2009, which is specifically incorporated by reference herein to the extent not inconsistent with the present application.

STATEMENT REGARDING FEDERALLY SPONSORED RESEARCH OR DEVELOPMENT

This invention was made at least in part with U.S. government support under 1935-42000-035 awarded by the U.S. Department of Agriculture and by EEC-0914790 awarded by the National Science Foundation. The government has certain rights in the invention.

REFERENCE TO A SEQUENCE LISTING

A sequence listing containing SEQ ID NOs: 1-6 is submitted herewith and is specifically incorporated by reference.

BACKGROUND OF THE INVENTION

Provided herein is label free electrical methods of detection and characterization of nucleic acid amplification products by probing the dielectric properties of the molecules in solution in a microfluidic device with an interdigitated electrode array.

Currently, the state of the art micro-fabricated devices for polymerase chain reaction (PCR) detection focus mainly on optical detection approach, such as on-chip capillary electrophoresis detection or labeling the amplified products with an intercalating fluorescent dye and reporter particles for detection. Although, those methods are very efficient in comparison to conventional gel electrophoresis methods, the requirement of an optical component integrated into micro-fabricated devices not only limits portability, but also increases the labor and total cost of those devices. Instead of using fluorescence label for optical detection, the electrical properties of DNA molecules can be a good candidate for developing a non-optical PCR detection method.

DNA molecules when suspended in solution will have counter ions surrounding them. These counter ions have two layers; one is associated with the bounded ions, i.e. condensed ions, and the other one is a loosely surrounded ion cloud. When the DNA molecules are probed in an electrical field, the DNA molecules will have longitudinal and transverse dipole moments, formed by counter ions and negatively charged backbone phosphate group.

Most of the research and detection methods of DNA dielectric properties in the past few decades focus on the range of frequency lower than kilohertz, where longitudinal dipole moments dominates the response. However, most of the applications utilizing the longitudinal dipole moments as a means of detection mechanism have not been successful due to complex influences from different types of background ions, charge neutralization and binding to the back-bone, mixed signals from longitudinal and transverse dipole moments, and also length-dependent alpha relaxation.

Instead, by probing at an appropriate frequency range (kilo-Hertz to mega-Hertz), and fitting the measured impedance versus frequency characteristics to an equivalent circuit model, the transverse dipole moment of DNA molecules can be explicitly extracted from mixed dipole moments (longitudinal and transverse) and can be shown to impact the solution dielectric capacitance. This method can also avoid the interference of ionic interactions of DNA solution with a measurement device, such as double layer perturbation, and electrode polarization.

The method, when performed in an integrated manner, can provide point-of-care label-free electronic detection of PCR reactions and nucleic acids in general for a wide range of applications in clinical diagnostics, global health, and individualized medicine.

SUMMARY OF THE INVENTION

Disclosed are methods, and related devices, that provide PCR product detection by electrical means that does not require any label. In particular, nucleic acid amplification products are detected and/or characterized by probing the dielectric properties of the amplified products in the PCR solution.

The methods rely on probing of the PCR solution at an appropriate frequency range (kHz to MHz) and fitting the measured impedance versus frequency characteristics to an equivalent circuit model. The transverse dipole moment of nucleic acid molecules, such as DNA, is explicitly extracted from mixed dipole moments (longitudinal and transverse) to show the impact on solution dielectric capacitance. One advantage of the methods provided herein is the avoidance of the interference arising from the interference of ionic interaction of DNA solution with the measurement device, such as double layer perturbation, and electrode polarization. In addition, by confining the PCR to a local region having a relatively small volume, significant increases in sensitivity and accuracy is achieved that cannot be obtained in conventional methods that do not use such a confined volume.

The processes disclosed herein are useful in a number of fields, including for detection of RNA by isothermal amplification, by thermal cycling for detection of amplified DNA. The devices and methods are optionally further combined with lysing and amplification (e.g., culturing) processes and devices to provide high sensitivity and reliability for various applications including point-of-care label-free electronic detection of PCR reactions, clinical diagnostics, global health and individualized medicine.

In one embodiment, provided is a method for detecting a PCR product in solution by providing a microfluidic amplification chamber comprising an electrode array on at least one surface of the microfluidic amplification chamber. A PCR solution is introduced that may contain a template to be amplified by PCR in the microfluidic chamber. A PCR is performed on the PCR solution, wherein the PCR is performed in a confined region to generate an amplified PCR product in solution. Alternatively, or in addition, PCR product is contained in the confined region, thereby effectively increasing the concentration of PCR product in a confined region. In that aspect, PCR may occur in a separate region, and PCR product then introduced to a confined region. In an aspect, the confined region is characterized by a volume, such as a confined region having a volume that is less than or equal to 500 µL or less than or equal to 200 µL. In an aspect, the confined region corresponds to a droplet surrounded by surrounding media, such as an ionic liquid, that is immiscible with the droplet. In an aspect, the droplet contains the ingredients required for PCR (e.g., PCR reagents and the nucleic acid material being tested, such as from a biological cell) and PCR is conducted in the droplet. Alternatively, PCR product is confined to a droplet that is electrically characterized. In an aspect, the droplet is described in terms of a droplet parameter, such as droplet diameter, droplet volume, of for droplets flowing past the electrode array, droplet spacing (e.g., distance between adjacent flowing droplets). An electric potential is applied to the electrode array to produce an electric field in the confined region and an electrical parameter of the PCR solution in the confined region is measured. In an aspect the electrical parameter is solution impedance. The magnitude of the impedance depends on the amount of nucleic acid in the confined region.

In another aspect, the volume of the confined region is described functionally, such as by providing a minimum concentration of template in the confined region. Providing a confined region for PCR effectively increases the concentration of the template, thereby increasing the system's sensitivity. Conventional PCR in larger volumes results in a lower concentration of template, and associated PCR product, making it more difficult to reliably detect changes in the electrical parameter associated with increase PCR product during the PCR cycling. By monitoring the electrical parameter in the confined region, however, the processes and devices disclosed herein are able to reliably detect PCR product with a lower number of PCR cycles, thereby significantly reducing the time required to detect PCR product. In an aspect, the invention provides reliable detection of PCR product after between about 5 to about 10 PCR cycles.

In an embodiment, the confined region has a volume that depends on the application of interest. For example, the confined region may have a volume that is less than or equal to 1 pL for detecting a PCR product from a bacterial cell. In another example, the confined region may have a volume that is less than or equal to 10 pL for detecting a PCR product from a mammalian cell. These relatively small volumes may be achieved by controllably introducing PCR solution to a confined region, such as by using flow control valves, pumps, pressure-driven flow or electrokinetics. In an aspect, local thermal variations may be used to precisely confine PCR by appropriately confining the template and/or PCR reaction to the confined region, such as a confined region that is within the microfluidic amplification chamber. Alternatively, droplets containing needed PCR components may be correspondingly confined to the droplet interior and manipulated to be positioned within the electric field generated by the electrode area. Any one or more of these methods or others known in the art may be used to provide a confined region, such as a confined region that is in the sub-nanoliter range. Alternatively, the microfluidic amplification chamber itself may be designed to correspond to the confined region, such as a microfluidic amplification chamber having a volume that is less than about 200 μL, or that is in the sub-nL range.

To further increase sensitivity and detection characteristics, another aspect of the invention relates to selecting a media that surrounds the droplet to further improve electrical measurement, detection and signal to noise ratio. Any media that is conductive and water immiscible can be used to confine a droplet with surrounding media. For example, in aspects where the droplet contains PCR product to be detected and/or corresponding required PCR reagents, an ionic liquid (IL) surrounds the droplet, such as an IL comprising a cation. In an aspect, any of the methods and devices provided herein relate to a flow of droplets suspended in flowing ionic liquid that is not miscible with the droplet.

Any of the methods and devices provided herein optionally further relate to the application of a hydrophobic surface coating to increase droplet stability throughout the thermocycling process. The hydrophobic surface coating is also advantageous in that it provides increased droplet maneuverability, placement and control. In an embodiment, the hydrophobic surface coating is trichloro-perfluorooctyl-silane (PFO). A hydrophobic surface coating, such as a PFO coating, minimizes the adsorption of protein to the device surface which in turn allows droplets to maintain a more stable contact angle with the device. In an aspect, PFO is mixed with anhydrous ethanol and the solution is applied to the device surface, such as by pipetting, and the ethanol allowed to evaporate. Excess PFO is removed using an acetone, methanol, DI rinse.

In an aspect, the ionic liquid is described in accordance with desired physical and chemical properties, such as being electrically conductive and immiscible with an aqueous solution. Preferably, the IL has no effective vapor pressure, is non-flammable, and has high ionic conductivity, such as a conductivity that is greater than or equal to 0.1 S/m or greater than or equal to 0.14 S/m. Preferably, the IL has a wide liquid range up to 300° C., and is thermally stable up to about 200° C. In an aspect, the IL is selected for the capability of dissolving a wide range of inorganic, organometallic compounds, and a capability to capture small molecules (e.g., $H_2$, CO, $CO_2$, and $O_2$). In an aspect, the IL is immiscible with certain organic solvents (e.g., alkanes). In an aspect, the IL is highly polar but is non-coordinating. In an aspect, the IL is selected so that polarity and hydrophilicity/lipophilicity can be easily tailored, such as by the selection of R groups to provide desired polarity and hydrophilicity/lipophilicity to the IL.

In an aspect, the ionic liquid is a cation/anion mixture. In an embodiment, the IL is imidazolium-based. In an embodiment, the IL comprises a first compound selected from the group consisting of:

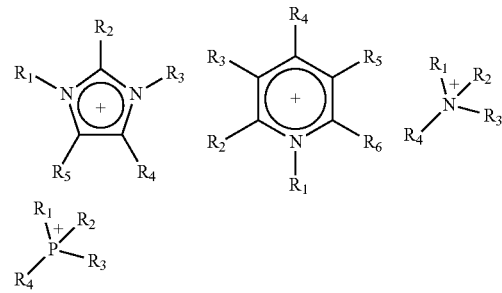

and a second compound selected from the group consisting of:

$Cl^-/AlCl_3$
$Cl^-$, $Br^-$, $I^-$
$[NO_3]^-$, $[SO_4]_2^-$
$[BF_4]^-$
$[PF_6]^-$
$[(CF_3SO_2)_2N]^-$

In an aspect, R1-R6 are individually independently selected to be H or alkyl, such as alkyl ranging in length from 1 to 10, or any of the other groups described hereinbelow.

In an aspect, the ionic liquid is an immidazolium-based ionic liquids of formula:

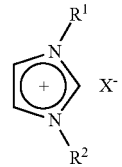

wherein X is an anion, such as Cl$^-$/AlCl$_3$, PF$_6$, BF$_4$, Cl, Br, I, NO$_3$, [SO$_4$]$_2$; (CF$_3$SO$_2$)$_2$N; and R1 and R2 are alkyl, such as R1 butyl and R2 methyl, or any of the other groups described hereinbelow.

Examples of ionic liquids conductive and immiscible with aqueous solution include, but are not limited to: (1) a PF6 anion, such as: 1-butyl-3-methylimidazolium hexafluorophosphate ([BMIM][PF6]), 1-hexyl-3-methylimidazolium hexafluorophosphate ([HMIM][PF6]), 1-octyl-3-methylimidazolium hexafluorophosphate ([OMIM][PF6]); (2) Tf2N anion: 1-ethyl-3-methylimidazolium bis(trifluoromethylsulfonyl)imide ([EMIM][Tf2N]), 1-butyl-3-methylimidazolium bis(trifluoromethylsulfonyl)imide ([BMIM][Tf2N]), 1-hexyl-3-methylimidazolium bis(trifluoromethylsulfonyl) imide ([HMIM][Tf2N]), 1-octyl-3-methylimidazolium bis (trifluoromethylsulfonyl)imide ([OMIM][Tf2N]), 1-phenylpropyl-3-methylimidazolium bis(trifluoromethylsulfonyl) imide ([PMIM][Tf2N]); SbF6 anion: 1-butyl-3-methylimidazolium hexafluoroantimonate ([BMIM][SbF6]), 1-hexyl-3-methylimidazolium hexafluoroantimonate ([HMIM][SbF6]), 1-Phenylpropyl-3-methylimidazolium hexafluoroantimonate ([PMIM][SbF6]). Although the exemplified ILs are imidazolium-based, the methods and devices described herein are not limited solely to imidazolium-based ionic liquids and the exemplified cations. Instead, any ionic liquid is compatible so long as it is conductive and immiscible with aqueous solution. For example, a "molten salt" is optionally used as the ionic liquid.

In another embodiment, the confined region has a volume selected from a range that is greater than or equal to 0.5 pL and less than or equal to 1 nL.

Although the devices and methods may use a wide variety of electrode arrays in a wide range of geometry, in one embodiment the electrode array is positioned on one surface of the microfluidic amplification chamber, such as a bottom surface over which a PCR solution flows. Alternatively, the electrode array may be configured such that one array is provided on one surface, and another array is provided on a correspondingly opposed surface. The applied voltage and frequency are selected to provide detectable electrical parameters over the confined region. In an aspect, a single electrode is used. In an aspect, a pair of electrodes are used. In an aspect, three electrodes are used. In an embodiment, the electrodes are configured and positioned to electrically detect a droplet flowing past the electrodes.

In one embodiment, the electrode array comprises an interdigitated array of electrodes having a width selected from a range that is greater than or equal to 10 nm and less than or equal to 100 µm and a separation distance between adjacent electrodes selected from a range that is greater than or equal to 10 nm and less than or equal to 100 µm. In an aspect, the dimensions are approximately 25 µm. The electrodes are formed of any material known in the electrode art, such as a metal or from a combination of metals.

In another embodiment, the microfluidic amplification chamber comprises side walls formed of PDMS and a bottom surface of a Si-containing material, such as SiO$_2$, wherein the bottom surface supports the electrode array. Optionally, the microfluidic amplification chamber is controllably fluidically isolated by one or more fluid control valves, such as by being operably connected to a reservoir containing the solution for performing PCR or to a reservoir containing the solution that may contain template to be amplified by PCR reaction (e.g., the sample reservoir or source). In an aspect, the fluidic control relates to generating droplets and/or separating droplets, such as by a network of conduits or channels to controllably effect fluid flow and corresponding droplet generation. In an aspect, the conduits have diameters that are selected from a range that is greater than or equal to 10 µm and less than or equal to 500 µm, and having a network geometry and physical characteristics as desired. For example conduit bifurcation angle, dimension, taper, input and/or output flow rate ratio, are selected depending on the desired droplet characteristics (e.g., size, separation, position). For example, one fluid stream may relate to sample-containing material, another to PCR-containing materials, and another to IL in which the droplet is surrounded to improve electrical detection of droplets and/or to improve the signal to noise ratio.

In an embodiment where the confined region is functionally defined, the volume may be selected to provide a minimum concentration of template in the confined region that is greater than or equal to 10 template molecules per pico liter of volume. For example, any of the methods and devices provide a detection limit of as low as 0.1 µg DNA templates in the confined volume, or is capable of reliably detecting a PCR product from a starting concentration that is as low as 10 template molecules/pL.

In an embodiment, any of the methods provided herein are performed continuously over the PCR cycle. In an embodiment, the detecting step is performed continuously or after each PCR cycle. In an aspect, the determining step is capable of determining step is capable of resolving a PCR product concentration difference between consecutive PCR cycles, such as for a PCR cycle number that is less than or equal to 10, less than or equal to 5, or between 4 and 9. By optionally concentrating the initial starting template molecule concentration, the process is capable of detecting PCR product after a significantly lower number of cycles than conventional processes.

Detecting is used broadly herein. For example, the detecting step may simply correspond to identifying a presence or an absence of the PCR product. Absence of PCR product indicates that template in the original sample is absent. In embodiments where the method relates to detection of pathogen, absence of PCR product then corresponds to a sample that is substantially or completely free of pathogen.

In an embodiment, the sample comprises one or more target cells, and the method further comprises lysing the target cells and contacting the lysate with the PCR solution. Lysing refers to a process that ensures that nucleic acid is released from a cell and made available to necessary components of the PCR solution, such as for example, primers, dNTPs and polymerases. Examples of such processes include heating, chemical exposure, or both. In an aspect, any of the methods are for a PCR product (e.g. a template) that is a contiguous sequence of DNA or RNA from bacterial, mammalian or viral cells.

Systems and devices provided herein are particularly useful as they are capable of performing PCR, and corresponding PCR detection, on a wide range of samples, including samples that may be made of target cells comprising one or a plurality of cell populations. In this manner, a single test may be used to simultaneously screen for the presence of one of a plurality of pathogens. For example, the method optionally relates to detecting a liquid- or food-borne pathogen.

Any of the methods and devices provided herein are designed to have a confined region of a defined volume and/or spatial boundary. For example, the confined region may, in fact, be the microfluidic amplification chamber (e.g., fixed spatial boundary). Alternatively, the confined region may correspond to a droplet containing said PCR solution, or a fluid containing a template to be amplified (e.g., defined volume). In this manner, PCR occurs in a well-defined "confined region". In an aspect, the droplet is formed by surrounding the PCR solution with a hydrophobic liquid. In an aspect, the hydrophobic liquid is mineral oil. In an aspect, the surrounding media is an electrically-conductive liquid, including an ionic liquid that is not miscible with the droplet. In an aspect, the surrounding media is any of the ionic liquids disclosed herein.

Any of the methods or devices provided herein provide a detection having a sensitivity that is as low as 1 template molecule/10 pL.

In an aspect, the microfluidic amplification chamber has a volume that is selected from a range of 10 µL to 150 µL. In an aspect where the microfluidic amplification chamber corresponds to a droplet, the droplet has a user-selected volume, such as a volume selected from a range that is greater than or equal to 1 µL and less than or equal to 500 µL, and any sub-range therebetween. In an aspect, any of the methods and devices provided herein relate to selectively adjusting orientation, configuration, flow-rate of and/or compositions of a first flow-inlet containing PCR-related materials and a second flow-inlet containing the surrounding media to selectively adjust droplet volume and/or droplet spacing.

In another embodiment, prior to the PCR step, the PCR solution comprises DNA having a concentration that is selected from a range that is greater than or equal to $5*10^8$ DNA molecules/µL and less than or equal to $10^{10}$ DNA molecules/µL.

In an aspect, any of the methods and devices is for a PCR product that is DNA.

In another aspect, any of the methods and devices is for a PCR product that is RNA, wherein the PCR is by isothermal amplification. In an aspect, the RNA is microRNA.

In an embodiment, the PCR product is DNA having a length that is selected from a range that is greater than or equal to 50 base pairs and less than or equal to 5000 base pairs.

In an aspect, any of the devices or methods relate to a point-of-care detection assay. In an aspect, any of the devices or methods relate to detection of PCR product that is label-free. In an aspect, any of the devices or methods relate to identifying the presence or absence of a PCR product. In an aspect, any of the devices or methods relate to determining the concentration of the PCR products or the number of PCR products.

The invention also relates to a method of detecting a PCR product in solution from a sample, such as by obtaining a sample comprising cells. The sample is introduced to an integrated biochip, wherein the integrated biochip comprises a microfluidic amplification chamber having an electrode array on one or more surfaces of said microfluidic amplification chamber, and performing one or more or all of the following steps on the integrated biochip: (i) concentrating the cells; (ii) lysing the cells to obtain a lysate; (iii) introducing to the microfluidic chamber the lysate and a solution for performing a PCR on a template contained in said lysate, thereby forming a PCR solution; (iv) performing a PCR on said PCR solution, wherein said PCR is performed in a confined region to generate from the template an amplified PCR product in solution; (v) applying an electric potential to the interdigitated electrode array to produce an electric field in the confined region; and (vi) measuring an electrical parameter of the PCR solution in the confined region, wherein the electrical parameter is solution impedance, thereby detecting the PCR product in solution. Optionally, the PCR and/or PCR end product are confined in a droplet that flows past the electrodes for electrical detection. In this aspect, the methods and device, including the integrated biochip, further comprise a fluid network for controllably generating droplets containing the PCR product surrounded by a surrounding media that is ionically conductive and immiscible with the aqueous droplet. In this aspect, the fluid network comprises a plurality of fluid conduits configured to provide control of a droplet characteristic (e.g., droplet size, droplet spacing, concentration or amount of biological material or PCR product in the droplet).

In an embodiment, the method further comprises growing, such as culturing, the cells in the integrated biochip, thereby increasing the number of cells in the integrated biochip, which correspondingly leads to a potential increase in the number of template molecules in the confined region. In an aspect, where the template starting material is present, the step of confining the starting material to a confined region provides at least a 10-fold increase in the starting material compared to processes that do not similarly confine. In an aspect, the concentrating step provides at least a $10^4$-fold or $10^5$-fold increase in concentration of template molecules (or cells containing the template molecule) compared to the template molecule concentration in the introduced sample including, for example, by confining within a droplet.

In an aspect, in any of the methods or devices described herein the confined region is one or more of a droplet that confines the PCR reaction to a volume defined by the droplet, a defined volume that is a sub-region of said microfluidic amplification chamber, or is the microfluidic flow chamber. In an aspect, the droplets are suspended or surrounded by a fluid that is flowing (e.g., "surrounding media"), so that the electrical monitoring corresponds to electrical monitoring of droplets flowing past or over the electrodes.

In an aspect, the confined region has a volume that is less than or equal to 200 µL.

In an embodiment, any of the methods or devices provided herein relate to detecting a product from one or more of bacteria, virus, mammalian, yeast, plant or isolates thereof.

In another aspect, the detection of the PCR product is for the presence or absence of a food-borne pathogen, such as a food-borne pathogen selected from the group consisting of: *Listeria* moncytogenes; *Escherichia coli*; *Campylobacter jejun*; *Listeria innocua*; and *Lactobacillus acidophilus*.

In an aspect, the concentrating step is by dielectrophoresis, antibody-based capture, cell culturing, or any combination thereof. In an aspect, the lysing step is by heating, such as for example by heating generated by electrodes used in the in the dielectrophoresis step. Alternatively, the lysing may be by chemical means.

In another embodiment, the invention relates to devices for carrying out any of the disclosed methods. In one embodiment, the device is an integrated biochip for label-free detection of PCR product, comprising an inflow port for introducing a sample to the integrated biochip. A filter is connected to the inflow port for removing unwanted components from the sample. A microchannel that receives flowing sample is positioned downstream of the filter and inlet port. A first electrode array for concentrating one or more cell populations present in the sample in the microchannel. The first electrode array may be used for dielectrophoresis. A heater for lysing the concentrated cell population is operably connected to the microchannel, and specifically the concentrated cell population(s) in the microchannel. A microfluidic amplification chamber having a confined region is in fluid communication with the microchannel. A second electrode array on at least one surface of the microfluidic amplification chamber generates an electric field in the confined region. An electrical parameter is measured in the confined region, such as with an impedance sensor or analyzer, such as any of those known in the art including U.S. Pat. Nos. 7,393,644, 7,135,294 and 7,452,669.

Optionally, the integrated biochip further comprises a reservoir in fluid communication with the confined region for performing PCR on the biochip, said reservoir comprising one or more reagents required for performing a PCR. In an embodiment, the integrated biochip further comprises a valve positioned between the reservoir and the microfluidic amplification chamber for controllably introducing the PCR reagents to the microfluidic amplification chamber.

Without wishing to be bound by any particular theory, there can be discussion herein of beliefs or understandings of underlying principles or mechanisms relating to embodiments of the invention. It is recognized that regardless of the ultimate correctness of any explanation or hypothesis, an embodiment of the invention can nonetheless be operative and useful.

BRIEF DESCRIPTION OF THE DRAWINGS

FIG. 4A: Pre- and post-PCR summary data with DEP concentration. FIG. 4B: Specificity trials for *L. monocytogenes* V7 with concentrations of 108, 107 and 106 cfu ml-1 sample comprising a 1:1:1 mixture of *L. monocytogenes* V7, *L. innocuo* F4248 and *E. coli* H157:O7 as the starting template. The control sampled comprised a 1:1 mixture of *L. innocuo* F4248 and *E. coli* H157:O7 as the starting template.

FIG. 7A is a plot of the impedance ($C_{di}$) in pF for S0, S30 and C30. FIG. 7B provides the percentage change of $C_{di}$ before and after PCR with and without template.

FIG. 9A: Top view of a silicon chamber for electrical detection of bacterial growth (Gomez, et al. 2005). Drawn area is where the mechanical filters may be formed. FIG. 9B Schematic of the chip with a septum layer on top to prevent evaporation of fluid during the temperature cycling. Sealing the ports in the glass chips is important to prevent evaporation of the small fluid volumes during PCR.

FIG. 10: Cross-section of mechanism of electrokinetic concentration (Lee, et al. 2003; Sin, et al. 2008).

FIG. 18: PBS-in-mineral oil droplets. PBS droplets are generated by introducing to a collecting vessel PBS (0.4 μL/min) and mineral oil (3.0 μL/min). The channel height is 27.5 μm, resulting in a droplet size of 21.161±0.651 μm and a droplet separation of 393.073±5.937 μm. With this configuration (PBS droplets in mineral oil), the PBS droplets are not electronically detected (250 kHz, 2.5V) (bottom panel).

FIG. 19: PBS-in-mineral oil plugs. PBS droplets are generated by introducing to a collecting vessel PBS (0.5 μL/min) and mineral oil (2.0 μL/min). The channel height is 27.5 μm, resulting in a droplet size of 37.566±1.361 μm. With this configuration (PBS plugs in mineral oil), the PBS plugs are not electronically detected (250 kHz, 2.5V) (bottom panel).

FIG. 20: Exemplary embodiments of ionic liquids (IL) for use with droplet detection. The top panel illustrates common cations and anions. In one embodiment, the IL is an imidazolium-based IL. In one embodiment, the imidazolium-based IL is [bmim]PF$_6$ (middle panel). Various physical properties for three different ILs are summarized in the bottom panel table.

FIG. 21: PBS-in-IL ([bmim]PF$_6$) droplets. PBS droplets are generated by introducing to a collecting vessel PBS (0.4 μL/min) and IL (0.018 μL/min). The resulting droplet size is 14.509±0.454 μm and a droplet separation of 7.452±1.412 μm. With this configuration (PBS droplets in IL), the PBS droplets are electrically detected as they pass the electrodes (see bottom panel), in contrast to the systems summarized in FIGS. 18-19.

FIG. 22: PBS-in-IL ([bmim]$PF_6$) plugs. PBS plugs are generated by introducing to a collecting vessel PBS (0.25 µL/min) and IL (0.2 µL/min). The resulting droplet size is 38.871±0.924 µm and a droplet separation of 2.237±1.192 µm. With this configuration (PBS droplets in IL), the PBS droplets are electrically detected as they pass the electrodes (see bottom panel), in contrast to the systems summarized in FIGS. 18-19.

FIG. 24: Illustrates PCR amplification in droplets. The droplets are static PBS suspended in oil. The droplet diameters range in size from 50-200 µm. The cell concentration is about $10^6$ to $10^7$ bacteria cells/mL, with 1 µM each of forward and reverse primer to the *L. monocytogenes* prfA gene (508 bp). The top panels are photographs of the droplets (about 100 µm in diameter) containing a cluster of bacteria. The bottom panels show the droplets before PCR cycling (bottom left panel) and after 30 cycles, 15 s per thermal cycling step, total 1 hour (bottom right panel).

DETAILED DESCRIPTION OF THE INVENTION

Figure 1:
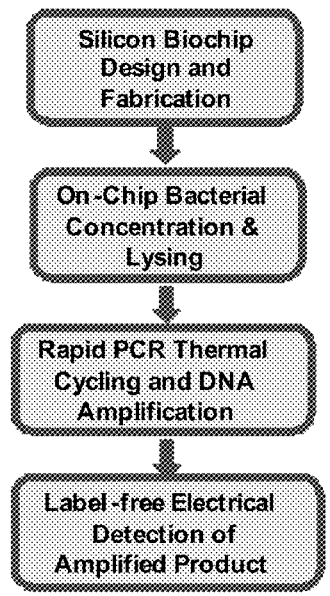
FIG. 1: Functional considerations in the development of devices and processes.

In general, the terms and phrases used herein have their art-recognized meaning, which can be found by reference to standard texts, journal references, including those referenced herein, and contexts known to those skilled in art. The following definitions are provided to clarify their specific use in the context of the invention.

"PCR solution" refers to materials required to perform a PCR as known in the art. Examples of such materials include primers, enzymes such as polymerases (e.g., Taq. polymerase), dNTP, nucleases, salts ($MgCl_2$) and PCR buffers to facilitate effective PCR. In an aspect, the PCR solution contains template, and more specifically a nucleic acid sequence that contains the template as well as flanking sequences. The PCR solution may contain nucleic acid material from a biological cell, such as nucleic acid material from a lysed cell. In an aspect, the PCR solution does not contain template, in which case the absence of template in the system will lead to no detection of PCR product. PCR product refers to the nucleic acid sequence that is produced as a result of the polymerase chain reaction process.

"Template" refers to the nucleic acid that is to be amplified by PCR. The template may be RNA or DNA. In an aspect, the template to be amplified corresponds to a nucleic acid sequence that is uniquely identified with a specific organism. For example, to detect a bacterial pathogen, a template that is a contiguous nucleic acid sequence unique to that pathogen is selected. The genomic DNA surrounding the template informs the selection of primers that provides specific amplification of the template portion. A "template molecule" refers to a piece of nucleic acid that may be larger than the template portion.

A solution that "may contain template" refers to a sample that is introduced to the device in which it is desired to determine whether or not it contains template. For example, in point-of-care diagnostics or assays it is often desired to determine whether any of the DNA in the sample contains template. Similarly, in assays for the detection of a food borne pathogen, the template may correspond to a sequence that uniquely identifies the pathogen of interest. For rapid screening of multiple pathogens, the template may correspond to multiple templates, with each template identifying a specific pathogen. Accordingly, the method may rapidly confirm there is no food borne pathogen, but if there is measureable signal, subsequent tests may be performed, if desired, to identify the specific pathogen. In another aspect, the method relates to introducing a solution that is known to contain the template.

"Electrical parameter" refers to a parameter that is measured in response to the exposure of a solution containing nucleic acid to an electric field. Preferably, the electrical parameter varies with nucleic acid concentration, such as impedance or a parameter related thereto.

"Operationally connected" refers to a configuration of elements such as device components, wherein an action or reaction of one element affects another element, but in a manner that preserves each element's functionality. Operationally connected device components may be in contact, such as a fluid control valve and a microfluidic amplification chamber and/or a reservoir. Alternatively, operationally connected components may be connected by one or more intervening components, such as flow conduits. As used herein, a flow control valve that is operationally connected to a fluid reservoir refers to the functional ability to control flow out of the reservoir. Accordingly, the valve can "controllably isolate", in a fluid sense, the microfluidic amplification chamber. For example, the flow control valve may prevent flow to the chamber, or may provide a controlled introduction of one or more materials (e.g., sample, template, primers and/or polymerase) to a chamber,)and more particularly to a confined region where PCR occurs and PCR product detected by measuring an electrical parameter.

"Target cells" refers to a biological cell whose detection, such as presence or absence, is desired. For example, the target cell may be one or more of a pathogen. The pathogen may be viral, bacterial or mammalian in nature. The methods provided herein are useful for a range of applications, including detecting one or more pathogens, such as a pathogen corresponding to a disease state (e.g., a mutation in the genome associate with a disease state or increased likelihood of the disease state) or a pathogen that may cause a disease state (e.g., the presence of bacterial and/or viral cells). The processes may be used to detect any pathogen of interest, so long as primers are available that are specific to that pathogen.

"Lysing" refers to the release of nucleic from a cell, such that the nucleic acid is made available to a solution having the components necessary for performing PCR.

"Droplet" refers to a defined volume of solution that is separated from surrounding solution. The solution confined in the droplet may be a PCR solution, including a material that is being tested for the presence/absence of a PCR product, such as a material potentially containing a biological cell such as a mammalian or bacterial cell, a virus, or potential genetic mutation that can be detected by PCR or isothermal amplification. Well-defined droplets may be formed by surrounding a water-phase aqueous solution with a hydrophobic solution and/or a liquid immiscible with respect to an aqueous droplet. In an aspect, the surrounding liquid is electrically conductive, such as an ionic liquid that is immiscible with the aqueous solution droplet. Alternatively, artificial membranes may be used, as known in the art, to envelop a PCR solution and the enveloped droplet of PCR solution introduced to the confined region. The droplet may be positioned as desired via flow-control means, such as generation of convective currents in the chamber such as by flow introduction or by selective heat generation to form flow currents that force droplets to the confined region. In an aspect, the electrical measurements relate to measurements of droplets in a flow of fluid, and any of the methods and/or devices provided herein relate to electrical detection and measurement of droplets, where the droplets preferentially contain the to-be-detected product.

"Sensitivity" refers to the minimum amount of template required to reliably detect PCR product. Alternatively, sensitivity refers to the ability to electrically detect differences between consecutive PCR cycles, such as at a low PCR cycle number (e.g., less than about 10 cycles).

"Point-of-care" refers to tests performed on a sample obtained from a patient, wherein the diagnosis is provided at the time of the test. For example, tissue may be obtained directly from the patient, and introduced to any of the systems described herein, and a diagnostic result generated with the test result provided to the patient.

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

EXAMPLE 1

System and Process Design

Nucleic acid-based methods are still considered the gold-standard for detection and identification of microorganisms due to their high specificity and selectivity as compared to antibody-based assays. Two factors limit the wide-spread use of nucleic acid based detection methods in the low-resource settings and as point of care tests, namely, (i) the high cost of reagents and instrumentation for optical detection of the amplified PCR product, and (ii) the long time of PCR amplification. Presented herein are novel solutions to circumvent the above limitations by development of a single use biochip cartridge for the electrical detection of nucleic acids for identification of pathogens from a fluid sample (eventually from throat swab or sputum). *Listeria monocytogenes* and *Mycobacterium avium* (a BSL-2 model for *Mycobacterium tuberculosis*) are used to test the technology platform.

We focus on sample preparation, concentration, and electrical detection of biological entities. More specifically, the processes are based on a recent finding that the presence of dsDNA molecules suspended in solution can be detected by measuring the impedance of the solution that the molecules are suspended in, provided that the concentration of the molecules is above a critical threshold. This threshold is about 1e8 molecules/µL for a 500 bp long ds DNA in de-ionized water (Liu, et al. 2008a,b) and about 1e16 molecules/µL in PCR solution (i.e. in the presence of all components necessary to perform PCR). Accordingly, a solution with about 1000 cells flowing through a channel with mechanical filters at one end to confine the bacteria in a 0.1 mL volume, lysing the bacteria and amplifying the target DNA segment for 30 cycles (PCR or isothermal amplification—amplified by 1e9 times), and confining the amplified product to the same volume, then the amplified product would detectably change the electrical properties of the solution. The electrical properties of the solution are modified due to the increased capacitance and dielectric polarization of the amplified dsDNA, and these modified properties are measureable using impedance spectroscopy through integrated on-chip electrodes. The technique is amenable to employ in a cartridge with an electrical and fluidic interface to a hand held reader, where the assay can identify target pathogenic microorganism based on detection of target nucleic acids in less than 15 minutes. FIG. 1 is a schematic overview of select design elements for a device that may be portable and by utilizing micro- and nano-scale technology systems, provides detection and quantification of unlabeled PCR amplicons and achieves results more rapidly than conventional optical devices.

Referring to FIG. 1, silicon biochips with mechanical filters for concentration of microorganisms, and electrodes for impedance measurements of the solution are provided. Heaters are optionally integrated with the silicon chip, such as by being placed underneath the chip surface, to rapidly heat and cool the target chambers in the chip. That configuration provides concentration and heat-lysing of bacteria in sub-nano-liter scale chambers in a silicon-based micro-fluidic devices. PCR amplification techniques (using existing primers and reagent kits) are used for the rapid amplification of the target gene of interest. The amplified DNA target is concentrated close to the region of interest, such as by electro-osmotic methods in between the amplification cycles. The integrated electrodes measure the impedance of the solution and detect the presence of the amplified DNA molecules in a label-free manner. Reference chambers and electrodes cam be integrated to increase the signal to noise ratio and provide a reliable signal for the identification of the target PCR product. In this example, the presence of PCR product would indicate present of the target bacteria.

The crisis in the management of disease for the global health requires rapid, easy to use, integrate, and cheap diagnostic devices for the detection of bacteria, viruses and other agents of infectious diseases. Particularly important is the need to miniaturize nucleic acid based detection techniques without sacrificing sensitivity and reliability or unduly impacting cost. Nucleic acid-based methods are still considered the gold-standard for detection and identification of microorganisms and viruses due to their high specificity and selectivity as compared to antibody-based assays. The recent technological advances in microfluidics and micro/nanotechnology present new opportunities for development of small, sensitive, single-use, point-of-care diagnostic devices that are capable of rapid analysis of nucleic acid amplification for the global health applications.

Since the invention of Polymerase Chain Reaction (PCR) based amplification of nucleic acids by Kary Mullis in 1983, researchers have spent significant effort to improve the sensitivity and selectivity of PCR assays and dramatically enhanced its application. PCR is now the cornerstone of modern biotechnology and biological identification. Due to the growing demands of on-site diagnosis, attention has been paid in realizing portable, fast and low cost PCR machines. However, there are still two barriers in making PCR truly a point-of-care test, i.e.; (i) the time for performing the thermal cycles and the PCR assays, and (ii) reagents and instrumentation for the optical detection. Much work has been devoted toward reducing performance time by reducing the thermal mass of the reaction volume where the amplification is taking place and, hence, reducing the time for each amplification cycle. Commercial systems now claim complete results in 45 minutes or less. At the research scale, micro-fluidic devices have been reported to reduce the thermal mass significantly, from the first report (Northrup et al. 1993) to many reports in recent years to microliter volumes (Lagally et al., 2001, Khandurina et al., 2000) and nanoliter scale volumes (El-Ali et al., 2004, Liao et al., 2004, Ke et al., 2006, Bhattacharya et al., 2008). The ramp rates for cooling and heating have been improved from ~4° C./s (cooling, Taylor, et al., 1997) and ~6° C./s (heating, Belgrader, et al., 1999) to ~30° C./s and ~50° C./s, respectively, (El-Ali, et al., 2004) potentially realizing 30 cycles to be run within 10 minutes. Other novel designs such as flow-through devices have also been reported, potentially reducing the time for amplification to few minutes (Zhang et al., 2002, Hashimoto et al., 2006).

The second barrier, the optical detection, still has much room for improvement. Current PCR schemes require optical fluorescent labels. However, work is ongoing with respect to label-free detection of DNA molecules, thereby bypassing the need for optical detection. Towards this front, the direct electrical detection of DNA in solution is potentially a very attractive option for detection of PCR products, especially if differences in length and concentrations can be detected directly without any labels or the need to attach the molecules to a surface. The basic mechanism behind the electrical response of DNA molecules in solution under an applied alternating electrical field stems from the formation and relaxation of the induced dipole moment (Jungner et al, 1949). Electrical properties of DNA in aqueous solutions have been explored and the studies indicate that since there is mobile charge in and around the DNA, a dipole can be induced in the DNA when probed electrically in solution (Hanss, 1973; Baker-Jarvis, et al. 1998). To-date, most of the label-free DNA detection mechanisms require DNA attachment to surface electrodes (Fritz, et al. 2002; Guidicci, et al. 2006; Hou, et al. 2007). However, there are a few reports of electrical measurements to detect DNA molecules in solution, with sizes ranging from 20-mer oligonucleotides to λ-DNA (Hong, et al. 2004; Yi, et al. 2005). Those reports show the promise of label-free DNA detection in solution; however, studies are required to explore the sensitivity and limits of detection and the physics behind the detection mechanism. Electrical characterizations of DNA of different lengths and concentrations in solution have been reported (Lee, et al. 2005; Berdet, et al. 2006), and the results showed correlation between changes in solution impedance and the DNA molecules. We have recently shown that the solution with DNA can be modeled as a lump electrical circuit and that the changes in impedance of the solution with the DNA can be correlated to the concentration of DNA. Our measurements also reveal further insight into the dipole moment of the DNA molecules as a function of their length and that the presence of molecules can be detected using direct label free impedance measurements in solution (Liu, et al. 2008a,b).

In summary, combining micro-fabrication techniques with novel design of heating/cooling schemes, and integrating electrical detection of the amplified PCR products, PCR can be made a fast and portable method for point-of-care diagnosis for the global health applications. The applications are much broader, of course, including the clinical diagnostic, food safety, environmental monitoring and homeland security.

EXAMPLE 2

Figure 2:
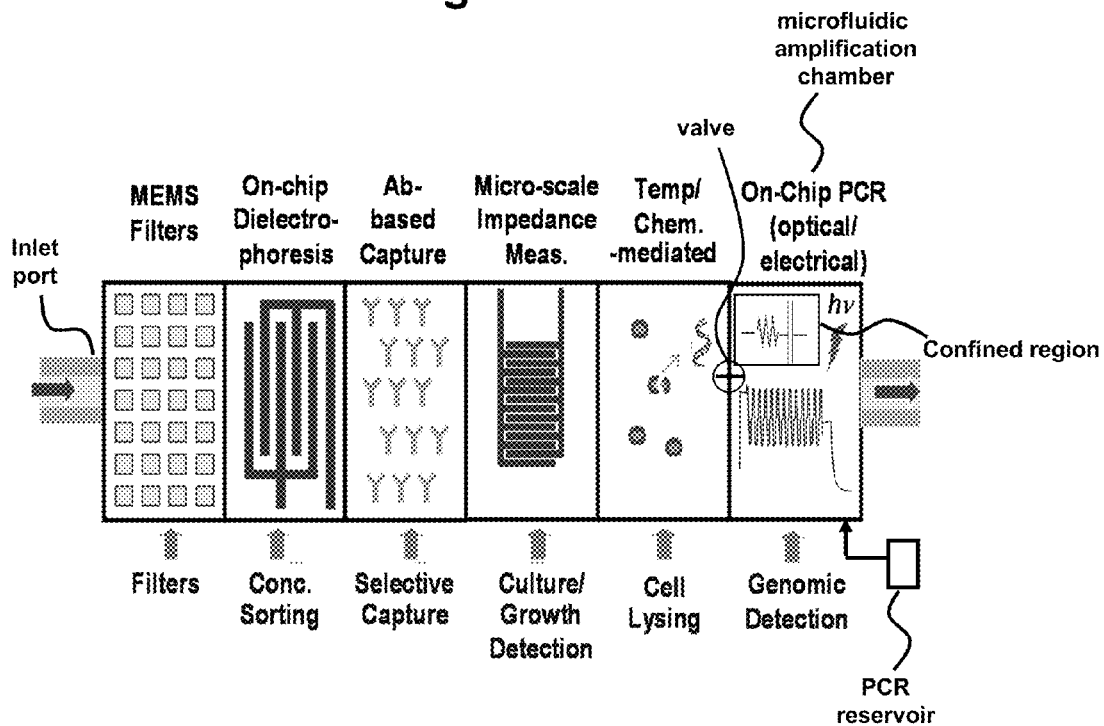
FIG. 2: Overview of the integrated biochip technology platform for on-chip detection of microorganisms. Depending on the specification application, not all modules are necessarily required and the sequence of modules may be rearranged based on the assay type and specification.

Label Free Electrical Detection of Nucleic Acid Amplification: This example provides bacterial detection using micro-fluidic devices. Important aspects relevant in this technique includes microfluidics, bacterial detection on chip, including separation, concentration, growth and culture, growth media development, antibody-based capture, amplification by PCR, and electrical sensing. Each of these aspects are employed to develop integrated devices for electrical detection of PCR product, with bacteria as the target model system for the technology development described. The process and device, however, is compatible with any sample containing nucleic acid or portions thereof amenable to PCR. FIG. 2 illustrates an exemplary technology platform (e.g., an integrated biochip) underlying a rapid, on chip, point-of care assays. It is important to note that this is an exemplary embodiment only, and that the exemplified modules might not all be used for every application; the modules are functional and conceptual, and can be performed in the same physical location on the chip. For the application exemplified herein, relevant modules include increasing concentration using mechanical filters, followed by lysing of the cells, and finally electrical detection of the genomic amplification. In other design configurations, the cells may be lysed first, followed by DNA separation and concentration. In an aspect, an inlet port provides introduction of sample to the integrated biochip. Depicted toward the downstream end of the integrated biochip, a valve facilitates flow control of the concentrated DNA sample to a microfluidic amplification chamber. Other reservoirs may be in fluid communication with the biochip, such as in fluid communication with the microfluidic amplification chamber. Depicted is a PCR reservoir. Optionally a valve is connected thereto to provide controllable introduction of necessary components for PCR. Similarly, multiple reservoirs may be provided, each having independently controlled flow, for added versatility. In this manner, droplets in which PCR product is confined may be generated, thereby improving the ability to electrically detect and characterize PCR product in a label-free manner.

Dielectrophoretic Bacterial Separation and Concentration: Integrated biochip devices that can capture, trap and detect specific bacteria and cells based on dielectrophoresis and antibody-mediated capture (Bashir, et al. 2004, Li, et al., 2005, Yang et al. 2006; see also U.S. Pat. App. 61/101,062 filed Sep. 29, 2008 and corresponding PCT pub. No. WO2010/037085). For these devices, we use dielectrophoresis (DEP) to concentrate bacterial cells to a surface under flow in a micro-channel. We have combined the advantages of DEP concentration and antibody specificity to demonstrate selective capture of target cells from a mixture of cells with similar dielectric properties in a micro-fluidic biochip (Yang et al. 2006). The exemplified device comprises an array of interdigitated electrodes on a flat silicon substrate and a 16 µm tall microchannel within a PDMS cover. Positive DEP (at $20V_{pp}$ and 1 MHz) is used to concentrate *Listeria monocytogenes* V7 cells from the fluid flow. Without DEP, no *Listeria* is observed on the channel surface. For selective capture of *Listeria* from samples, a monoclonal anti-*Listeria* antibody is immobilized onto the surface of the DEP chamber through biotin-streptavidin chemistry. With this device, the lowest number of cells captured by DEP from 5 µl of the sample was roughly 60 cells. When DEP is turned off, about 16 cells are captured from 5 µl. This result indicates that DEP is capable of capturing bacterial cells from a solution having low bacterial cell concentration, which is very useful for detection of pathogenic bacteria from fluid samples. The use of Ab capture coupled with PCR (described later) provides the unique ability to perform multiplexed detection (immuno- and PCR-based) on the same samples.

To reduce the time for detection of culture and perform the detection electrically, a microfluidic chip is used in which a small number of bacterial cells is concentrated from a dilute sample into nanoliter volumes, and then cultured (Gomez, et al., 2005). Taking advantage of the small volume of the biochip, we achieve $10^4$ to $10^5$ fold concentration of bacterial cells from a dilute sample. This novel "Impedance microbiology-on-a-chip" technique can dramatically reduce the requirement for amplifying the bacterial population used in many conventional methods, and thus the sensitivity and speed detection of bacterial growth can be greatly improved. Our measurements in silicon-based micro-fluidic devices indicate that the metabolic activity of just a few cells can be detected (Gomez et al., 2005).

Figures 3A, 3B, 3C:
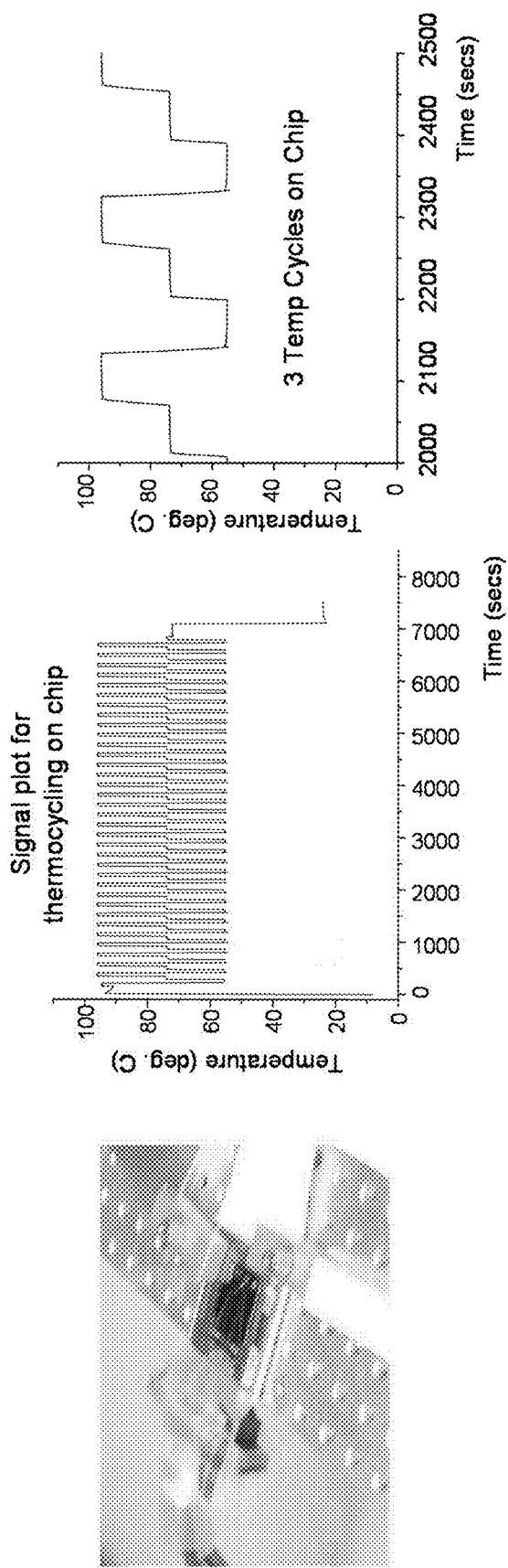
FIG. 3A: Basic arrangement of the thermal cycler (peltier cooler mounted with a PC-board-chip assembly.
FIG. 3B: Signal plot of a full 38 cycle amplification process as recorded from the chip.
FIG. 3C: Expanded view of the signal plot from time 2000-2500 secs.
Figure 4A:
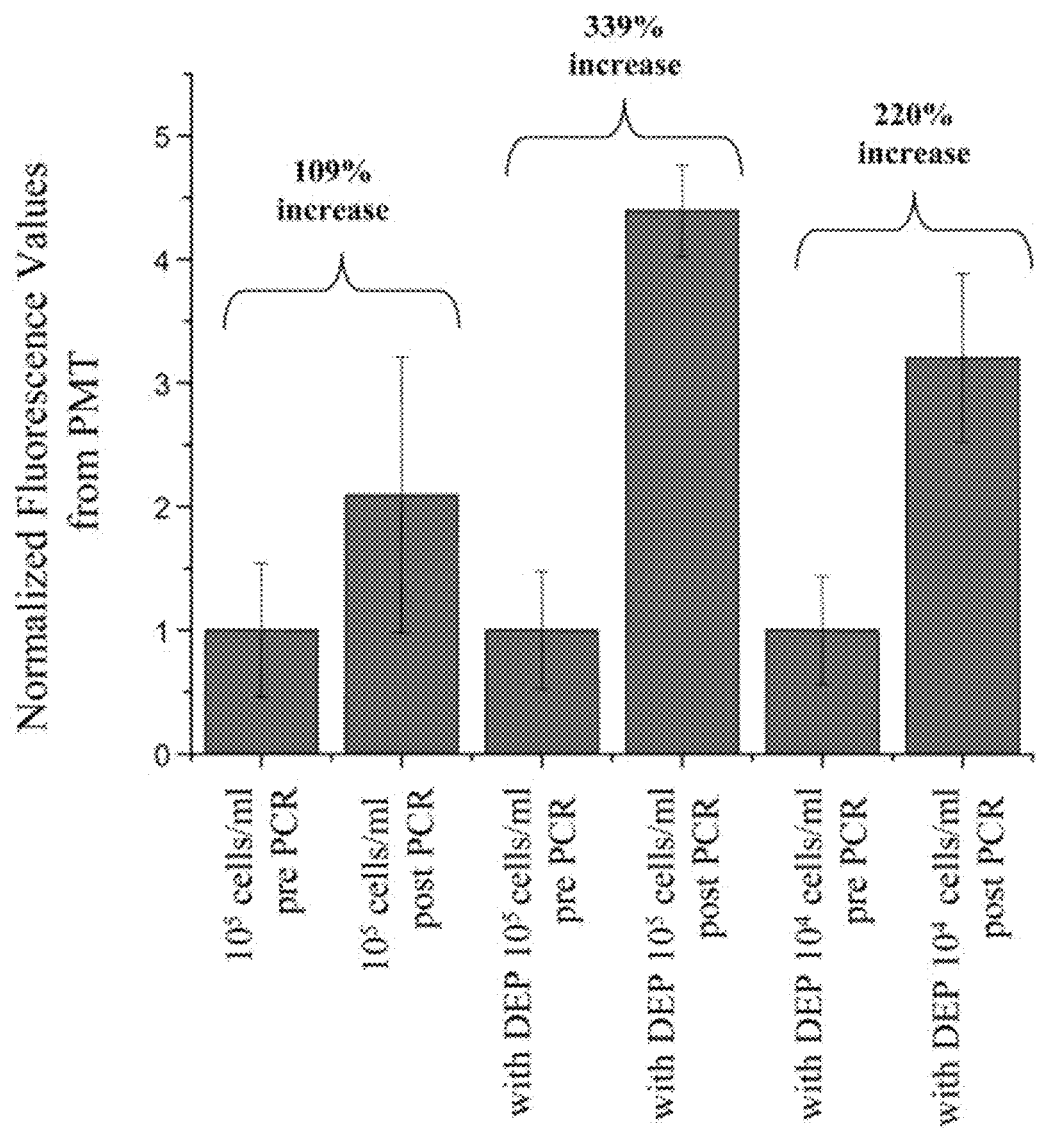
FIG. 4A-4B Fluorescence based detection of PCR amplification.
Figure 4B:
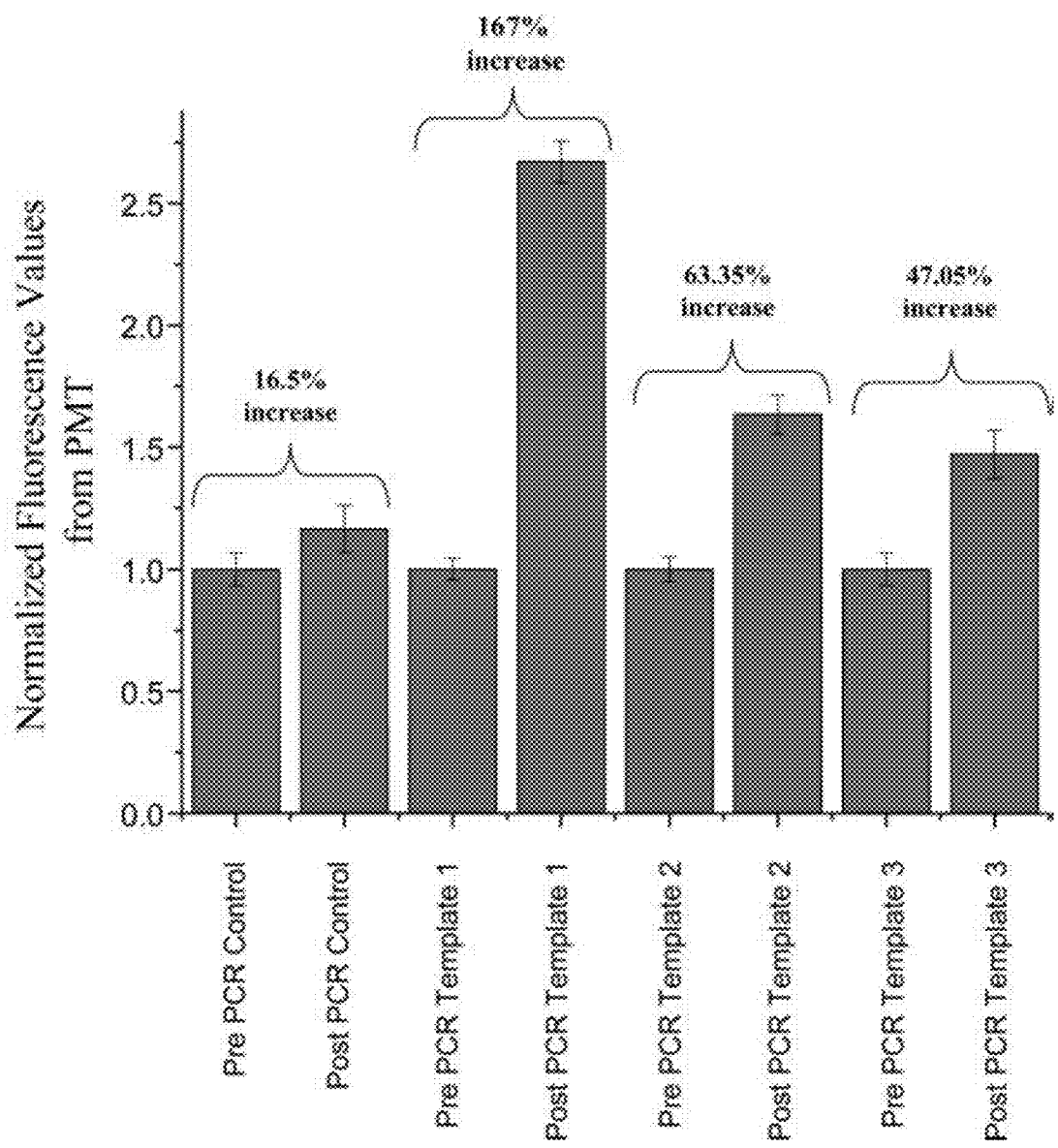

On-Chip Lysing and PCR-on-a-Chip: We have performed polymerase chain reaction amplifications of *Listeria monocytogenes* and that protocol is adapted to our silicon device platform to perform on-chip PCR detection and identification using optical fluorescence detection (Bhattacharya, et al. 2008). We use primers corresponding to a 508 base pair region of the performance regulatory factor A (PRFA) gene, a master controller specific for *Listeria monocytogenes* and critical to its pathogenicity and virulence. We validate protocols for both standard and real-time PCR, the latter using a SYBR green kit (Invitrogen Ltd.) on ABI prism 7000 series qRT-PCR equipment. These modules have also been translated to a glass-silicon biochip, with thermal cycling performed using a PC board (PCB) and other off-chip utilities, such as a programmable power supply, digital multi-meter, a Peltier cooler, with a National instrument DAQ (data acquisition) card. All thermal sensing on-chip is performed using a pre-calibrated thin-film thermocouple (also used earlier for cell growth). FIG. 3A-3C shows the equipment in operation and a signal plot of a complete thermal cycle on the chip. The Peltier cooler is placed at the bottom of the PCB to provide heat sink capabilities. Moderate temperature ramp up/down rates (3-5° C./sec) and a close control of temperature with +/−1° C. are obtained using this setup and various optimization regimes are performed. The average power requirement is about 1.5-2.0 watts. Cell lysis of *L. monocytogenes* is performed using the well-established procedure of thermal lysing of cells before PCR at 95° C. for 5 min in our chips. We perform end-point detection by recording the fluorescent output from the PMT signal with an automated shutter, after 35 cycles. FIG. 4A-4B shows a bar plot of the fluorescence readout from the PMT voltage output from the chambers on chip. On-chip trials, for different concentrations of *L. mono-cytogenes* V7, are performed and the fluorescence values are recorded before and after the thermal cycling. These fluorescence values are taken at multiple points on the chip and their averages and standard deviations are computed and plotted as a bar graph. An error bar, indicating the standard deviation in the fluorescence readings for each concentration, is also added to the average fluorescence bar graph. Trial 1 fluorescence values correspond to no-template control (no cells but all components of the PCR reaction). All fluorescence values are normalized with respect to a baseline. As seen in the average fluorescence plot, for the no-template control, a 28% increase in the fluorescence is recorded which may be attributed to the formation of primer-dimers intercalating with SYBR Green dye molecules. For the $10^8$ cfu ml$^{-1}$, the increase in fluorescence of the post PCR products is 503%. Similarly, for $10^7$ cfu ml-1, the increase is 448% and for $10^6$ cfu ml$^{-1}$, the increase is 177%. For $10^5$ cfu ml$^{-1}$ (corresponding to 60 cells) the average increase in fluorescence is 109% and the normalized fluorescence values of pre- and post-PCR are 1.0±0.4 (pre-PCR) and 2.1±1.1 (post-PCR). The minimum number of cells that can provide a nearly measurable signal in this example is 60. With a flow rate of 0.5 µl min$^{-1}$ and 100% capture efficiency, 500 cells can be trapped inside the chip in one minute, from a concentration of $10^6$ cfu ml$^{-1}$. Similarly, 50 and 5 cells can be trapped in one minute from a concentration of $10^5$ and $10^4$ cfu ml$^{-1}$ respectively. In order to achieve the minimum detectable limit of the system, DEP-based concentration is performed in the chip and dilutions ranging from about $10^5$-$10^4$ cfu ml$^{-1}$ are investigated. FIG. 4A shows that with the DEP-based concentration, the average fluorescence increase in the chamber for the concentration of $10^5$ cfu ml$^{-1}$ is about 339%, and the normalized fluorescence values are 1.0±0.5 and 4.3±0.4 for the pre- and post-PCR samples, respectively. As discussed earlier, this is a marked improvement compared to the trial done without DEP for the same concentration ($10^5$ cfu ml$^{-1}$), wherein, though the average increase in fluorescence is around 109%, the normalized fluorescence values before and after PCR are very close to each other. When using the concentration of $10^4$ cfu ml$^{-1}$ along with DEP, the post-PCR increase in fluorescence is observed to be 220%. The normalized fluorescence values vary in this case from 1.0±0.4 in pre-PCR solution to 3.2±0.68 in the post-PCR product. As stated earlier, the concentration of $10^4$ cfu ml$^{-1}$ is not detectable without DEP-based concentration.

*L. monocytogenes* V7 is used for on-chip DEP and PCR experiments, while *L. innocua* F4248, and *E. coli* O157:H7 are used for specificity testing. In these experiments, a mixture of approx. 108-106 cfu ml$^{-1}$ *L. monocytogenes* V7, 108 cfu ml$^{-1}$ *L. innocua* F4248, and 108 cfu ml$^{-1}$ *E. coli* O157:H7 are mixed in equal proportions. The primers used in these trials are highly specific to *L. monocytogenes* V7, and result in amplification of the 508 by region of the prfa gene. The control sample comprises *L. innocua* F4248 and *E. coli* O157:H7 alone. FIG. 4B illustrates the various normalized fluorescence values using the three cell mixtures. For the control sample the normalized fluorescence signal, after thermal cycle, increases by 16%. For the 108 cfu ml$^{-1}$ *L. monocytogenes* V7, *L. innocua* F4248, and *E. coli* O157:H7 (1:1:1) mixture, the increase in normalized fluorescence was 167%. For 107 and 106 cfu ml$^{-1}$ of *L. monocytogenes*, and 108 cfu ml$^{-1}$ *L. innocua* F4248, and *E. coli* O157:H7 (1:1:1) the recorded increase in fluorescence was 63 and 47% respectively. If we compare these values with the earlier ones involving one cell type (*L. monocytogenes* V7), we find a considerable decrease in the fluorescence values. The lower fluorescence signal in the case of specificity trials may be due to a decrease in the initial available template in this case to 33.33% (one-third) and due to other DNA sequences from *L. innocua* F4248, and *E. coli* O157:H7 that can compete for the total available PCR reactants, thus lowering the amplification efficiency. However, the increase of fluorescence is a positive indication of the presence of *L. monocytogenes* V7.

Figure 5A:
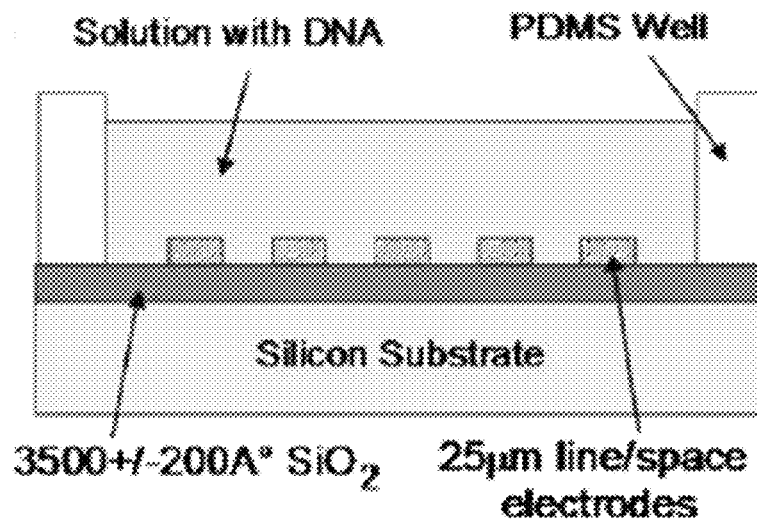
FIG. 5A is a schematic of a device for determining capacitance of a solution containing PCR product.

Electrical Detection of DNA Molecules: We have also recently performed impedance measurements of fluids to examine the impact of the length and concentration of free-floating double-stranded DNA molecules, as a goal towards electrical detection of PCR product (Liu, et al. 2008). We measure the impedance versus frequency characteristics and fit these to an equivalent circuit model including solution dielectric capacitance and conductance. The extraction of these parameters can be used to detect the presence of DNA molecules in the nM range for a 400 by long molecule. Our results indicate that the extracted dielectric capacitance and conductance increase with molecule length and concentration owing to a corresponding increase in number of molecule dipoles and counter-ions in solution. The detection electrodes of one device is fabricated by metal evaporation of 50 nm Ti and 250 nm of Au, 25 μm wide and 25 μm spacing, onto a 3500+/−200 Å thermal $SiO_2$ layer grown on a silicon substrate (FIG. 5A). The DNA molecules are prepared by gel extraction and ethanol precipitation. In that experiment, the DNA molecules are always resuspended in deionized water. An AC voltage with amplitude of 250 mV is applied to the electrodes and impedance was measured with frequency varying from 100 Hz to 1 MHz. Each scan with 19 steps takes about 1 minute to complete and three sweeps are taken for each experiment and averaged.

We first measure the impedance of the DNA solutions as a function of concentration and length of the DNA molecules and the impedance as a function of frequency is plotted for the various concentrations and DNA length. We found that the impedance magnitude decreased as the concentration of the 400 by dsDNA increased. The detection limit is found to be around 1 nM for the 400 by dsDNA molecule. Similarly, at the concentration of $10^9$ molecules/μl, the impedance magnitude is also found to decrease as the length of the dsDNA molecule increases.

Figure 5B:
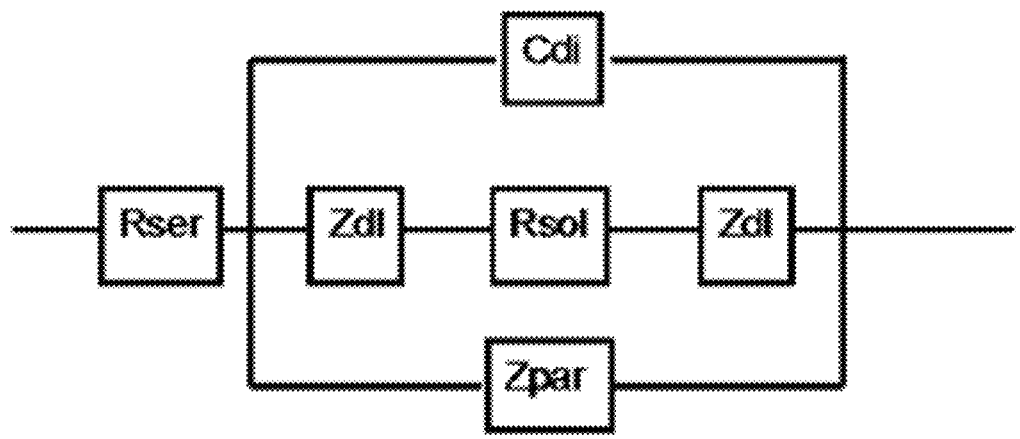
FIG. 5B is an equivalent circuit model diagram of the solution with DNA molecules.
Figure 6A:
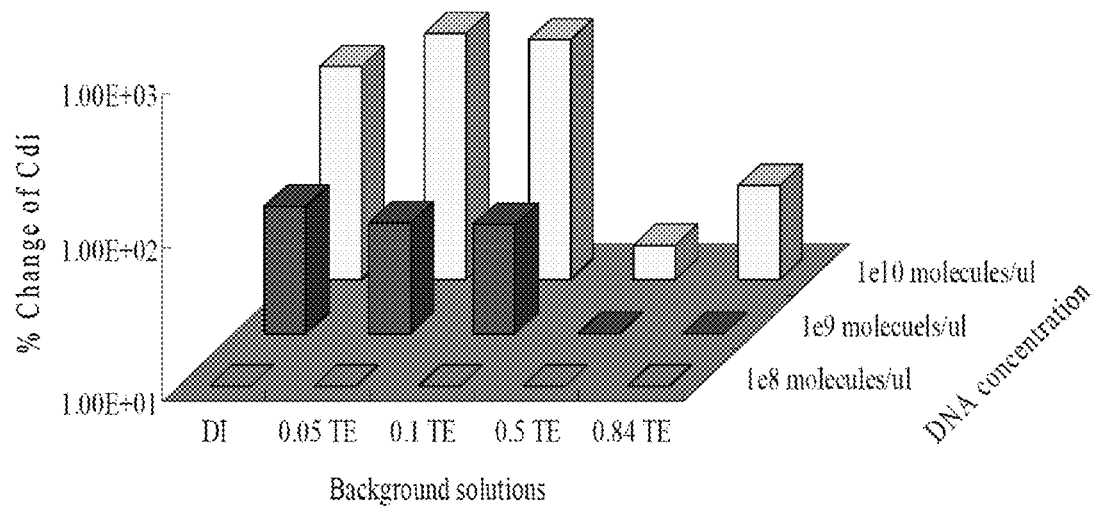
FIG. 6A: Label free detection of DNA molecules of various concentrations (y-axis) suspended in various strength TE buffers α-axis) and de-ionized water (DI).
Figure 6B:
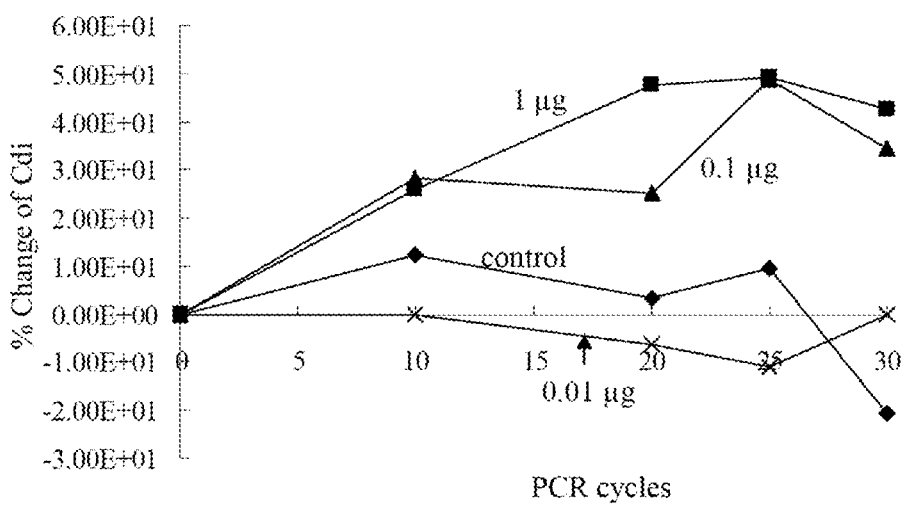
FIG. 6B Change in extracted $C_{di}$ versus PCR cycles for mixture of *Listeria monocytogenes, Listeria innocua,* and *Escherichia coli* templates with different primer concentrations, 1 μM and 0.1 μM, along with control experiments, *Listeria innocua* and *Escherichia coli* only, under same primer condition (Liu, et al. 2008).

We next show that the method can be used to detect the presence of the amplified PCR product in solution in a label free manner. We first measure the changes in impedance of DNA molecules in TE buffers. The data is fitted with an equivalent circuit model (FIG. 5B) and the dielectric capacitance of the solution $C_{di}$ is extracted. As shown in FIG. 6A, the detection threshold (>20% change in $C_{di}$) for a 508 bp long dsDNA molecule, in this experimental configuration, is about $10^9$ molecule/μL in 0.1 TE buffer and $10^{10}$ molecule/μl in 0.5 TE buffer and above. We further extend the process to the direct electrical detection of PCR. FIG. 6B shows the change in $C_{di}$ for the detection of *Listeria monocytogenes* prfA gene from mixture of *L. monocytogenes, Listeria innocua,* and *Escherichia coli* templates with primer concentrations of 1 μM and 0.1 μM. The template concentration is held constant, 1 μg of each bacteria. The target gene can be electrically detected after 10 cycles. It should be noted that 1 μg of initial genomic DNA corresponded to $3 \times 10^8$ bacterial cells, which is mixed in 25 μL solution. This corresponded to ~$10^7$ DNA molecules/μL in the PCR mix. After 20 cycles, this number increases, for example, to $10^{13}$/μL. It should also be noted that $10^7$ DNA molecules/μl corresponds to $10^4$/nL before the 20 cycle PCR. FIG. 6B shows the change in $C_{di}$ for mixture of *L. monocytogenes, L. innocua,* and *E. coli* templates with concentrations of *L. monocytogenes* varying from 1, 0.1, to 0.01 μg, where the primer concentration was held constant at 0.1 μM. The concentrations of *L. innocua* and *E. coli* genomes are kept constant at 1 pg in each reaction. The results show a change of over 40% in the extracted $C_{di}$ when *L. monocytogenes* prfA gene is amplified, while control experiments show an experimental error of less than 20%. Lowering primer or template concentration decreases the change of $C_{di}$; however, depletion of reaction agents also causes the decrease in the signal at the end of PCR process. Further characterization of change in $C_{di}$ is provided in FIG. 7A-7B. Thus our results confirm that the method successfully detects the presence of amplified DNA in solution by electrical monitoring of the PCR solution. Further improvement in sensitivity is achieved by optimization of one or more of concentration, lysing, amplification, and electrical detection of the amplified DNA in an integrated format within a microfluidic biochip.

Figure 8A:
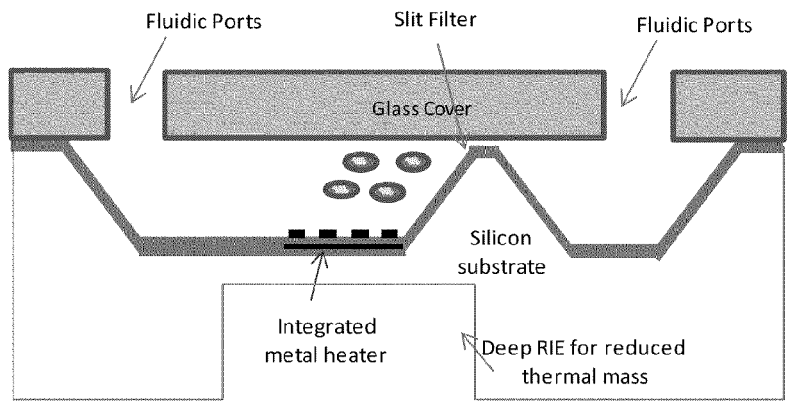
FIG. 8A: Cross-section of the integrated devices for on-chip electrical concentration and detection of DNA amplification.
Figure 8B:
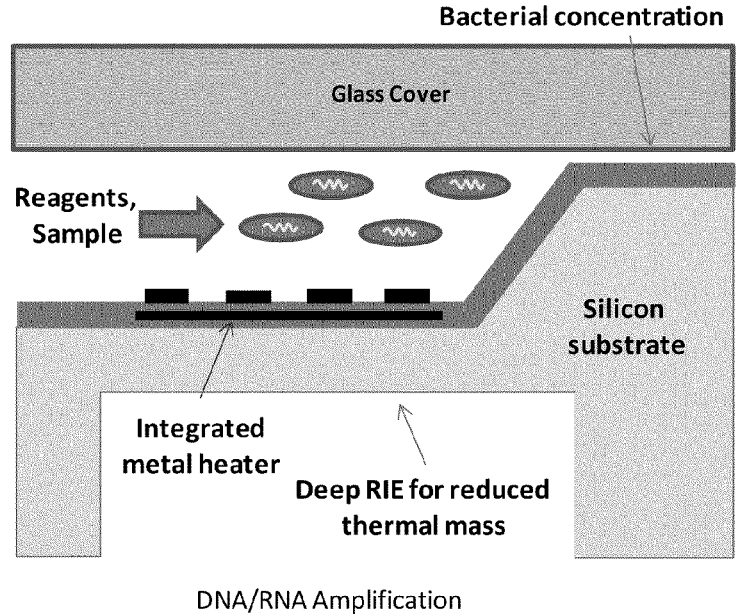
FIG. 8B close up of detection chamber after bacterial concentration.
Figure 8C:
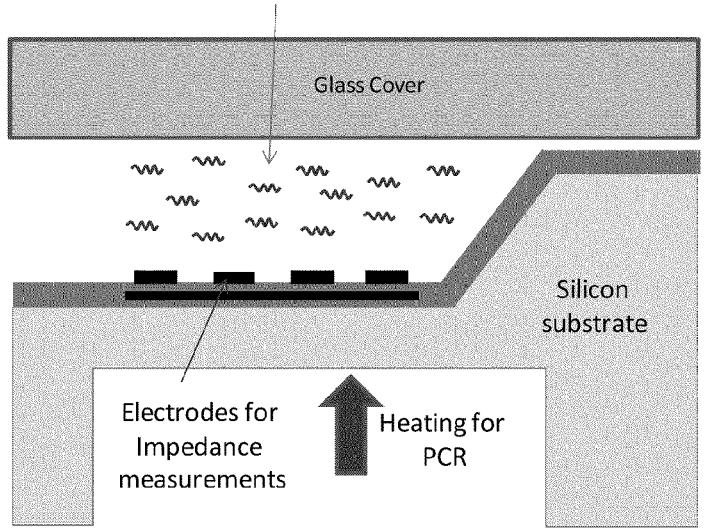
FIG. 8C after lysing, amplification, and detection.

Silicon biochip design and fabrication: Micro-fluidic devices are designed having: (i) integrated mechanical slit filters for on-chip concentration of bacteria or other biological organism, (ii) on-chip concentration electrodes for electrical concentration of the DNA using ac electro-osmosis and impedance measurements, and (iii) integrated heaters and temperature sensors for control of nucleic acid amplification reactions. A cross-sectional schematic of one embodiment is presented in FIG. 8A-8C. A device of interest is for integrated electrical detection of the nucleic acid amplification, including a device requiring reduced time for amplification/total assay. Such a device facilitates PCR tests that can be deployed as an at-point test. FIG. 9A-9B shows top view of a device (Gomez, et al. 2005) on which is added a mechanical filter with slit of 0.2 um for trapping the bacteria within the target chamber of about 1 nL volume. The key fabrication process steps, also adapted and enhanced from earlier work (Gomez, et al. 2005) is as follows: (i) formation of the 10-12 um deep silicon channels using TMAH etch, (ii) thermal oxidation, (iii) deposition and patterning of the metal heater under the chamber, (iii) deposition of PECVD oxide, (iv) etch back of the slits, (v) formation of metal electrodes for concentration and electrical detection, (vi) Deep reactive ion etching of the backside to produce a low thermal mass region, and finally (vii) anodic bonding of the glass cover. The chips are diced and packaged as shown in FIG. 9B. The device layout and the back side etch step is optimized to reduce the thermal mass to achieve complete process cycling in less than 15 minutes.

Typically, a few thousand cells in sub 0.5 nl volumes are required (in this example's configuration) to reliably detect the electrical signal due to a change in dielectric capacitance of the solution when a 500 bp molecule is amplified. For example, 0.1 nl corresponds to a volume of about 50 μm on each side. Thus the detection chamber size may, in an embodiment, be about 12 μm deep, 50 μm wide and 160 μm long. The electrodes may be 6 μm wide with 10 μm space, so that the electric fields would span the entire height of 12 μm (Li, et al. 2005).

Bacterial concentration and thermal lysing in silicon biochips: A whole detection assay can be carried out in the integrated micro-fluidic device ("integrated biochip"). Device and process characterization may use fluorescently labeled *L. monocytogenes* to show the concentration (video microscopy) using the mechanical filter slits in sub-nanoliter chambers on-chip. Then using non-fluorescently labeled *L. monocytogenes*, we demonstrate cell lysing using the embedded heating elements to heat up the chip to 95° C. Two different dyes are used to demonstrate cell lysing, i.e. FITC dye, $DiOC_6(3)$, and nucleic acid dye, propidium iodide. The FITC dye, $DiOC_6(3)$, is a lipophilic dye which stains membrane in both live and fixed cells. The propidium iodide (PI) dye binds to DNA and RNA and is useful for differentiating necrotic, apoptotic and healthy cells. PI can only penetrate compromised membranes and mark the inner DNA and RNA and does not label healthy cells.

Demonstration of local PCR in nanoliter volume with electrical concentration and fluorescence detection in silicon biochips: The released DNA is amplified by PCR amplification (or iso-thermal RNA amplification if information on live/dead bacteria are needed) for rapid amplification of the target gene of interest. The amplified DNA/RNA target is concentrated close to the region of interest by using electroosmotic methods during the thermal cycling. The thermal gradients would otherwise force the DNA molecules to diffuse away from the electrode regions and, hence, it is important to concentrate DNA in the solution to keep DNA confined close to or at the sensing electrodes (e.g., the "confined region"). Since electrophoresis alone is not effective in conductive media due to charge screening, we utilize electrokinetic flows using the same electrodes that are used to measure the impedance signals to detect the presence of DNA. Electrokinetics is utilized by applying an ac voltage between the interdigitated electrodes in the detection chamber to concentrate the DNA molecules on the electrodes as shown in FIG. 10 (Lee, et al. 2003; Sin, et al. 2008). In this manner a confined region is generated as a sub-region of the amplification chamber.

The PCR amplification is detected first using standard optical fluorescence labels (SYBR green) (Bhattacharya, et al. 2008) as a control to make sure that the amplification is indeed taking place and that the amplified molecules are confined to the region of interest in the micro-fluidic biochip. An amplification of a 508 base pair region of the prfA (performance regulatory factor A) gene using primers, which are highly specific to *Listeria monocytogenes*, is performed. The prfA (performance regulatory factor A) gene is the master controller for all other virulent gene expressions and is critical to the pathogenicity of the bacterial strains. Protocols for PCR in the standardized and real time mode are validated. This real time protocol is developed using a SYBR green kit (Invitrogen Ltd.) on a ABI prism 7000 series qRT-PCR equipment and is used the control for comparing the results from the on-chip devices with the low thermal mass. Ideally, the amplification occurs in less than 15 minutes with the optical fluorescence signal. We predict that the system is capable of detecting less than hundred cells using the optical fluorescence techniques (Bhattacharya, et al. 2008).

End-point electrical detection of PCR product DNA in nanoliter volume chambers: Building on this platform, we perform the critical task of electrical impedance measurements using the electrodes in the detection chamber to detect the amplified PCR products. We utilize the same primers (specific to prfA gene) for specific identification of *Listeria monocytogenes* as described above. As shown in FIG. 6B, the detectable change in electrical signal of PCR product generation can be much earlier than the usual 30 cycles. Our results indicate that we can readily observe a change in the dielectric capacitance $C_{di}$ between 10 and 20 cycles. We perform the thermal cycles and measure the end-point signal (differential signal with respect to a reference chamber), at 5, 10, 15, 20, 25, and 30 cycles to test how early the amplification signal can be generated. As per our earlier discussion, a few thousand cells in sub 0.5 nl volumes facilitates the detection of the electrical signal due to change in dielectric capacitance of the solution when a 500 bp molecule is amplified. We focus on using concentrations of starting bacteria in a range sufficiently high to demonstrate the electrical signal for detection of PCR products. Further optimization of the assay and related physical parameters informs sensitivity and selectivity.

Testing of integrated system with *L. monocytogenes* and *M. avium* to test for sensitivity and selectivity: Once the number of *L. monocytogenes* cells that can be electrically detected is determined (expected to be in the range of few thousand cells), we systematically determine the concentration that can be detected in a fluid sample. We flow 10 µl of buffer with varying numbers of bacterial cells, ranging from 10 cells to 10,000 cells (concentrations of $10^3$ cells/ml to $10^7$ cells/ml) and determine the minimum concentration or number of cells that can be reliably electrically detected. We use the same prfA gene primers that are used for earlier studies so that the results can be readily compared. We also use a mixture of *Listeria monocytogenes, Listeria* innocua, and *Escherichia coli* templates with different primer concentrations, 1 µM and 0.1 µM, along with control experiments, *Listeria innocua* and *Escherichia coli* only, under same primer condition to determine the selectivity of the on-chip electrical detection assay (as compared to the off-chip results in FIG. 6A-6B).

Next, we test the system with another model system more closely related to the global health application. *M. avium* complex (MAC) is a group of genetically-related bacteria belonging to the genus *Mycobacterium* and its symptoms and pulmonary involvement are similar to TB (MAC can cause cough, weight loss, upper-lobe x-ray changes, and cavities— all similar to TB). The risk of MAC is inversely related to people's CD4 count, and increases significantly when the CD4 count decreases below 50 cells/mL; therefore, MAC is severe to people who are HIV+. MAC is the most common NTM (Nontuberculous *Mycobacteria*) infection in AIDS.

MAC belong to Runyon's group III bacteria of the mycobacteria and are slow growing, the generating time is about 10 to 12 hours (Yamamoto, et al. 2002). *M. avium* is classified as BSL-2 bacteria and can be purchased from ATCC (ATCC® 19421™, *Mycobacterium avium* subsp. *Avium* Chester deposited as *Mycobacterium tuberculosis* (Zopf) Lehmann and Neumann). *M. avium* can be grown on Middlebrook 7H10 agar plates containing cycloheximide (55 ng/ml) and lincomycin (2 mg/liter) for 6 weeks in 37° C. or grown in Löwenstein-Jensen medium at 37° C. for 3 weeks (ATCC medium 90) or 7H9 broth for 1 week (Chen, et al. 1995). Specific primers target for *M. avium* can be found (Kulski et al. 1995; Chen et al. 1996). Here we utilize the primer set developed in Chen's work. The so-called MAV primer set is specific to *M. avium* (sense, 5'-CCT CAA GAC GCA TGT CTT CT-3' (SEQ ID NO:1); antisense, 5'-ACA GCT CCC TCC CAA AAG GG-3' (SEQ ID NO:2)) and targets the DNA sequences coding for two regions of the 16S rRNA sequences with the largest number of mismatched bases for identification. A universal primer set, MYCOB, contains sense 5'-ATG CAA GTC GAA CGG AAA GG-3' (SEQ ID NO:3) and antisense 5'-TGC ACA CAG GCC ACA AGG GA-3' (SEQ ID NO:4), can also be used for amplification; however, the amplification is not specific among *M. avium* other *Mycobacterium* species. We vary the number and concentrations as described above to determine the sensitivity of the electrical detection assay.

Figure 11:
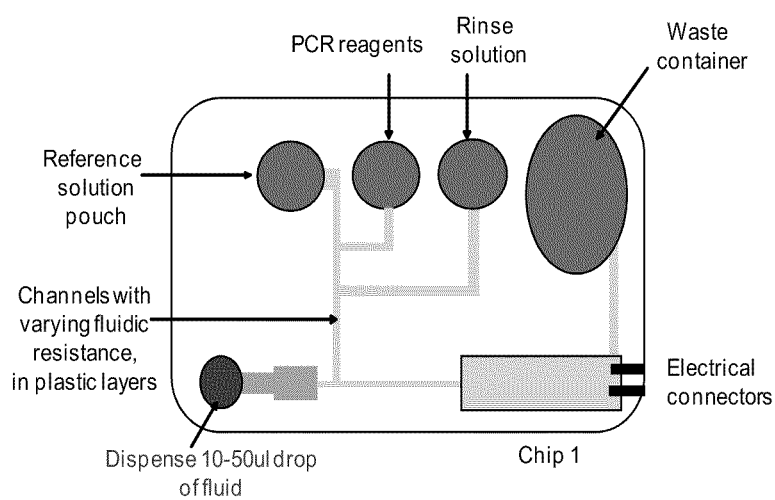
FIG. 11: Schematic of a cartridge to dispense droplets containing potential template nucleic acid and PCR solution to amplify the template.

An integrated system and cartridge: We have designed cartridges for electrical detection of bacterial growth and electrical detection of CD4+ cells from blood (FIG. 11). We utilize the findings and results of the assay development to further refine the specifications of realistic cartridges with the silicon biochips for electrical detection of PCR products (FIG. 11). Such cartridges need to house the chip, provide electrical and fluidic interfaces (optical interfaces not required), and also contain the reagents for the PCR. One of the main concerns related to the use of fluorescent nucleic acid stains is their relatively short shelf life at room temperature and we alleviate this concern through the label free electrical detection methods. The reader is optionally portable, such as about 6"×12"×3" in size, and can be battery operated. The impedance measurement circuitry can easily be designed on a circuit board, also including the circuitry to control the temperature for lysing and PCR on chip.

J. Baker-Jarvis, C. A. Jones, B. Riddle, NIST Technical Note 1509, 1998.

R. Bashir, Advanced Drug Delivery Review, Special issue: Intelligent Therapeutics: Biomimetic Systems and Nanotechnology in Drug Delivery, Edited by N. A. Peppas, Vol 56/11 pp 1565-1586, 2004.

P. Belgrader, W. Benett, D. Hadley, J. Richards, P. Stratton, R. Mariella, F. Milanovich, Science, 1999, 284, 449-450.

D. Berdat, A. Marin, F. Herrera, M. A. M. Gijs, Sensors and Actuators B, 118, 53 (2006).

S. Bhattacharya, S. Salamat, D. Morisette, P. Banada, D. Akin, Y. Liu, A. K. Bhunia, M. Ladisch, and R. Bashir, Lab Chip, 2008, 8, 1130-1136.

Z.-H. Chen, W. R. Butler, B. R. Bumstark, and D. G. Ahearn, Journal of Clinical Microbiology, 1996, 34, 1267-1269.

X. Cheng, Y. Liu, U. Dimirci, D. Irimia, L. Yang, L. Zamir, W. Rodriguez, M. Toner, R. Bashir, Special Issue on Cells and Tissue in Microsystems, Lab. Chip., 2007, 7, 746-755.

Z. Cui, Z. Zhao and S. Xia, Proceedings of SPIE, 2001, 4407, 275-280.

M. Hanss, Biopolymers, 12, 2151 (1973).

G. Jungner, I. Jungner, L. G. Allgen, Nature, 63, 849 (1949).

J. El-Ali, I. R. Perch-Nielsen, C. R. Poulsen, D. D. Bang, P. Telleman, A. Wolff, Sensors and Actuators A, 2004, 110, 3-10.

J. Fritz, E. B. Cooper, S. Gaudet, P. K. Sorger, S. R. Manalis, P.N.A.S., 99, 14142 (2002).

R. Gomez, D. Morrisette, R. Bashir, IEEE/ASME Journal of Microelectromechanical Systems, 2005, 14, 829-838.

C. Guiducci, C. Stagni, A. Fischetti, U. Mastromatteo, L. Benini, IEEE Sensors J., 6 (2006).

M. Hashimoto, F. Barany, S. A. Soper, Biosensors and Bioelectronics, 2006, 21, 1915-1923.

J. Hong, D. S. Yoon, M. Park, J. Choi, T. S. Kim, G. Im, S. Kim, Y. E. Pak, K. No, Japan. J. of Applied Physics, 43, 5639 (2004).

C. J. Hou, M. Godin, K. Payer, R. Chakrabarti, S. R. Manalis, Lab Chip, 7, 347 (2007).

C. Ke, A. Kelleher, H. Berney, M. Sheehan, A. Mathewson, Sensors and Actuators B, 2007, 120, 538-544.

J. Khandurina, T. E. McKnight, Stephen C. Jacobson, Larry C. Waters, Robert S. Foote, and J. Michael Ramsey, Anal. Chem., 2000, 72, 2995-3000.

J. K. Kulski, C. Khinsoe, T. Pryce, and K. Christiansen, Journal of Clinical Microbiology, 1995, 33, 668-674.

E. T. Lagally, I. Medintz, and R. A. Mathies, Anal. Chem., 2001, 73, 565-570.

S. W. Lee, R. Bashir, Appl. Phys. Lett. 83, 3833 (2003)

S. W. Lee, T. Yamamoto, T. Fujii, The 13th International Conference on Solid-State Sensors, Actuators and Microsystems, 2005.

H. Li, Y. Zheng, D. Akin, R. Bashir, IEEE/ASME Journal of Microelectromechanical Systems. Vol. 14, No. 1, February 2005, pp. 105-111

C. Liao, G. Lee, J. Wu, C. Chang, T. Hsieh, F. Huang, C. Luo, Biosensors and Bioelectronics, 2005, 20, 1341-1348.

Y. Liu, P. P. Banada, S. Bhattacharya, A. K. Bhunia, and R. Bashir, Applied Physics Letters, 92, 143902, 2008.

Y. Liu, P. P. Banada, S. Bhattacharya, A. K. Bhunia, and R. Bashir, IEEE Sensors Conference, 2008 (Accepted).

M. A. Northrup, M. T. Ching, R. M. White, R. T. Wltson, Proceedings of Transducers '93, 1993, 924-926.

W. R. Rodriguez, N. Christodoulides, P. N. Floriano, S. Graham, S. Mohanty, et al. PLoS Med 2005; 2:e182.

M. L. Y. Sin, V. U. Constantino, V. Gau, D. A. Haake, P. K. Wong, 3rd IEEE International Conference on Nano/Micro Engineered and Molecular Systems, 2008. NEMS 2008.

T. Taylor, E. Winn-Dean, E. Picozza, T. Woudenberg, M. Albin, Nucleic Acids Res., 1997, 25, 3164-3168.

K. Yamamoto, M. Rajagopalan, and M. Madiraju, J. Biochem., 2002, 131, 219-224.

L. Yang, P. Banada, M. R. Chatni, K, Lim, M. Ladisch, A. Bhunia, R. Bashir, Lab Chip, 6, 896-905, 2006.

M. Yi, K. Jeong, L. P. Lee, Biosensors and Bioelectronics, 20, 1320 (2005).

EXAMPLE 3

Characterization of DNA Detection in Various Strength Buffers and PCR Solutions

We have demonstrated that the dielectric properties of a solution will be altered if there are DNA molecules present above a certain concentration [13]. By fitting the measured impedance versus frequency characteristics to an equivalent circuit model including the solution resistance and dielectric capacitance, the extraction of these parameters can be used to detect the presence of DNA molecules in the solution.

However, the chemical and physical processes in PCR are far more complicated than the case of DNA molecules in de-ionized water. Therefore, we first examine the effect of various DNA concentrations in different strength TE buffers (10 mM Tris-HCL, pH 7.5, 1 mM EDTA). By investigating the dielectric properties of DNA molecules in high ionic buffers, i.e. TE buffers, we gain further insights into the DNA dipole effects when these molecules are suspended in complex solutions. Even though PCR solutions contain additional molecules such as PCR reagents, dNTPs and primers, the experiments provided herein illustrate a linear detection limit of DNA molecules as a function of increasing background conductivity.

After establishing the detection limit of dsDNA molecules in different background conductivities, we apply the label-free impedance spectroscopy method to the detection of PCR amplification. The PCR reagents contains 2.5 units of PuReTaq DNA polymerase, 10 mM Tris-HCl, (pH 9.0 at room temperature), 50 mM KCl, 1.5 mM $MgCl_2$, 200 µM of each dNTP, stabilizers, and BSA. Gene specific primers, targeted on *Listeria monocytogenes* prfA gene, are used for amplification. *Listeria monocytogenes* V7 is used as model microorganism for single strain bacterium detection and for selectivity detection with mixture of *Listeria innocua* F4248, and *Escherichia coli* O157:H7. Three template DNA concentrations, 1 µg, 0.1 µg and 0.01 µg in 25 µl final volume, are examined in selectivity experiments.

Materials and Methods: Sample preparation. All the samples are prepared from fresh colonies on BHI agar plates. The cells of *E. coli, L. innocua*, and *L. monocytogenes* are incubated 18-20 hours in BHI broth in a shaker incubator and then streaked on BHI agar plates for another 24 hours before harvest. The cells are collected from agar plates and heat lysed in a 95° C. water bath for 15 minutes, followed by 5 minutes quench in a −20° C. freezer. Other steps are taken in the following order: spinning down of cell debris (13.2 krpm for 30 seconds, Centrifuge 5415D, Eppendorf), collection of the supernatant, and check the purities and concentrations by a spectral photometer (Nanodrop, Wilmington, Del.). Templates are ready for PCR after these steps.

Correlation of cell concentration and released template DNA was confirmed by BHI agar plating and absorbance using a spectrophotometer. Sample bacteria, *Listeria monocytogenes* V7, with concentration of $2.8 \times 10^8$ cfu/ml contribute to 2 µg/ml DNA templates, corresponding to approximately $6 \times 10^8$ cells/ml (assuming an equal A, T, G, C content).

Two primers are used for PCR reaction targeted on *L. monocytogenes* prfA genes:

```
                                              (SEQ ID NO: 5)
ELMPRFAF  CGGGATAAAACCAAAACAATTT  (5' to 3')

(SEQ ID NO: 6)
ELMPRFAR  TGAGCTATGTGCGATGCCACTT  (5' to 3')
```

The PCR is performed with a pre-heat step of 94° C. for 5 minutes. This ensures that the genomic DNA molecules are completely denatured. The amplification process consists of 30 cycles with each cycle containing three steps: 94° C. for denaturation, 55° C. for annealing, and 72° C. for extension. Each of these steps is 1 minute. At the end the PCR process, 7 minutes of 72° C. is used to guarantee that the extensions are fully completed.

Samples are prepared and PCR is performed with various template concentrations to fully investigate the detection limit. For each PCR condition, there are three replicates, and each replicate has five samples designated for 0, 10, 20, 25 and 30 cycles of PCR. The reaction dynamics for detection can be observed through these designated samples. Samples of designated cycles for each replicate are prepared with all the templates, primers and PCR reagents mixed well before distributing to each PCR reservoir. This minimizes the experimental error due to sample preparation. Each designated PCR reservoir is collected at the end of each dedicated cycle of PCR, i.e. 10, 20, 25 and 30 cycles. The samples are stored at −20° C. and thawed immediately before subjected to impedance measurements.

Samples used for TE buffer experiments are prepared in the same manner with a further process of ethanol precipitation after PCR and checked by spectrophotometer (Nanodrop, Wilmington, Del.) for purity and concentration.

Micro-scale device design and fabrication: The detection electrodes of our device is fabricated by metal evaporation (CHA e-beam evaporator) of 50 nm of Ti and 250 nm of Au, 25 µm wide with 25 µm spacing, onto a 3500+/−200 Å thermal $SiO_2$ layer grown on a silicon substrate. A PDMS ((poly) dimethylsiloxane) well is made from a 10:1 mixture of elastomer base:curing agent (Sylgard 184 Silicone Elastomer, Dow Corning Corporation, Midland, Mich.) and cured in a hard-bake oven at 120° C. for 10 minutes. The PDMS reservoir is aligned and attached on top of electrodes.

Numerical data analysis: The numerical data analysis is performed by fitting measured data to an equivalent circuit model consisting interdigitated electrode structures and electrolyte. The device parasitic impedance originated from the oxide capacitance, and the substrate resistance is defined as $Z_{par} = [(j2\pi f)^n B]^{-1}$. $R_{ser}$ is the fixed resistance of the metal lines leading to the interdigitated electrodes. Both $R_{ser}$ and $Z_{par}$ are extracted from impedance measurement of the device without electrolyte and kept fixed for the rest of the analysis. The extraction of the model parameters is performed using Matlab® software (The MathWorks, Natick, Mass.) by iterating each parameter and minimizing the least square error between the model and the experimental data.

Results and discussions: DNA molecules in various strengths TE buffers. In the TE buffer experiments, the impact of background ionic strength on the extracted circuit parameters and determination of the detection sensitivity is examined. We measure the changes in impedance of solutions with DNA molecules in diluted TE buffers and fitted the data to an equivalent circuit model. The DNA samples are prepared as previously discussed and suspended in TE buffer to reach final concentrations of $10^{10}$, $10^9$, and $10^8$ molecules/µl and achieve the final strength of solutions as 0.05, 0.1, 0.5, and 0.84 with respect to the original TE buffer. As shown in FIG. 6A, the detection limits (defined as a 20% change in $C_{di}$) for a 508 bp long dsDNA molecule suspended in TE buffers, is found to be about $10^9$ molecule/µl in 0.1 TE buffer and $10^{10}$ molecule/µl in 0.5 TE buffer and above.

As discussed, the increase in concentration of DNA molecules gives rise to increase in solution dielectric capacitance due to an increase in the total DNA dipole moments. On the contrary, the dipole moment will decrease either by the fact that the DNA molecules are neutralized by ions in the solution or if the length of the DNA molecules decreases due to structural transition. The latter could happen to DNA molecules, with sizes longer than a certain length, when sufficient counter ions are provided in the solution. Therefore, as we expect, the results indicate that in comparison to the detection limit of dsDNA molecules in de-ionized water [13], i.e. $5 \times 10^8$ molecules/µl, the use of 0.5 TE buffer requires more DNA molecules, on the order of $10^{10}$ molecules/µl in the current configuration, to be detected by impedance measurements.

Detection of single strain PCR amplification: We start from measuring samples containing just one single strain of bacteria. A template concentration of 1 µg *L. monocytogenes* genomic DNA is used for PCR. Two sets of samples contained everything needed for PCR, except with and without the template DNA, are tested by impedance spectroscopy at the beginning and the end of PCR cycles. Results are shown in FIG. 7A-7B.

Figures 7A, 7B:
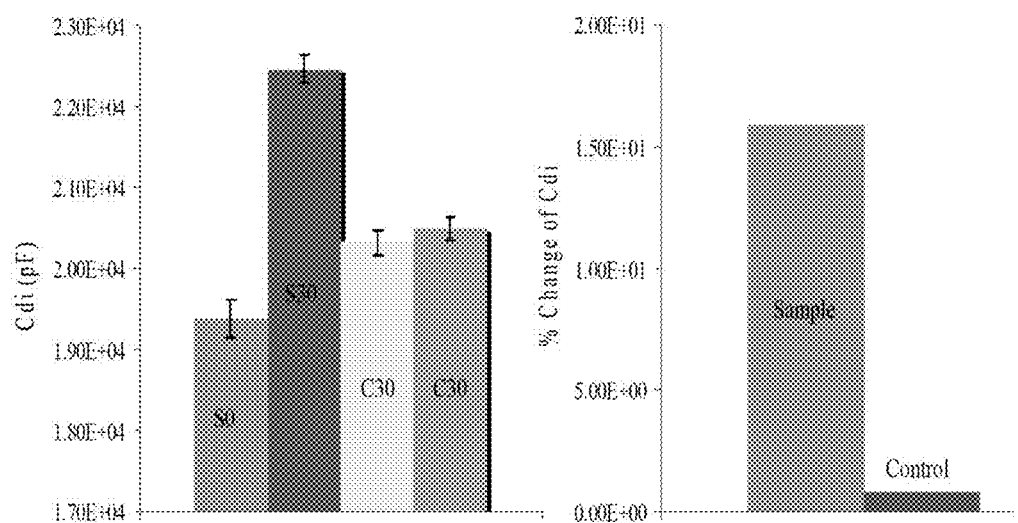
FIG. 7A-7B: Electrical end point detection of PCR. Sample data are identified with an S and control data are identified with a C. The samples and controls are identical except that the control data does not contain template DNA (*L. monocytogenes* genomic DNA). The number of PCR cycles are either 0 or 30, as indicated.

We observe an average of 16% change in solution dielectric capacitance ($C_{di}$) between samples before and after 30 cycles of PCR, in comparison to a 1% change of dielectric capacitance in the control experiment (FIG. 7B). However, in practice, the samples from the environment will not contain just one type of microorganism. Therefore, in order to validate the method for the detection of food-borne pathogens, as one of the application of the impedance-based label free PCR detection method, selectivity experiments of one specific bacterium from a mixture of microorganisms is also examined.

Selectivity detection: Three microorganisms, *L. monocytogenes, L. innocua*, and *E. coli*, are used as sample organisms. The target gene for amplification is the *L. monocytogenes* prfA gene. Three different template concentrations are investigated for detection limit. The results are shown in FIG. 6B.

FIG. 6B shows the change in $C_{di}$ for the detection of the *Listeria monocytogenes* prfA gene from mixture of *Listeria monocytogenes, Listeria innocua*, and *Escherichia coli* templates with concentrations of *Listeria monocytogenes* ranging from 1 µg, 0.1 µg, to 0.01 µg, in each 25 µl reaction volume, where the primer concentration is held constant at 0.1 µM. The concentrations of *Listeria innocua* and *Escherichia coli* genomes are kept the same at 1 µg in each reaction. The results show a change of over 40% in the extracted $C_{di}$ for both 1 µg and 0.1 µg cases when sufficient *Listeria monocytogenes* prfA gene is amplified, while control experiments and 0.01 µg experiment show an experimental error of less than 20%. Lowering template concentration decreases the change of $C_{di}$; however, depletion of reaction agents also causes a decrease in the signal at the end of PCR process as we can see in both 1 µg and 0.1 µg initial template cases. The detection limit in this case, i.e. with stated PCR conditions and examined microorganisms, is about 0.1 µg DNA templates in 25 µl total volumes, which corresponds to about $10^8$ cfu/ml. This number implies that within 10 cells in a sub-nano-liter scale PCR reaction chamber, as stated in most state of the art micro-fabricated PCR devices nowadays, the amplification of specific genes can be detected by the impedance-based label-free method.

In this example, we electrically probe DNA molecules in various concentrations of TE buffers and observe how they affect the solution electrical properties. The results show clear evidence confirming the theoretical predictions: Increasing the background ionic strength neutralized the net charges of DNA molecules and decreased the total DNA dipole moments. The detection limit increased when more ions were presented in the DNA solution, i.e. higher concentration of DNA molecules were needed for detection. Based on these studies, we applied the technique of model-based impedance spectroscopy to provide label-free detection of PCR products. By a variety of combinations of PCR conditions tested, we found a detection limit of as low as 0.1 µg DNA templates in a total 25 µl volumes, which corresponds to 10 cells in a sub-nano-liter reaction chamber, i.e. $10^8$ cells/ml. We conclude that impedance spectroscopy combined with a model-based parameter extraction method can be a very useful tool for low-cost, direct label-free detection of PCR amplicons. This methods and systems provided herein can be beneficial for point-of-care and on-site-diagnostics.

REFERENCES

[1] M. A. Northrup, M. T. Ching, R. M. White, R. T. Wltson, "DNA amplification with a microfabricated reaction chamber," Proceedings of Transducers '93, 1993, 924-926.

[2] E. T. Lagally, I. Medintz, and R. A. Mathies, "Single-Molecule DNA Amplification and Analysis in an Integrated Microfluidic Device," Anal. Chem., vol. 73, pp. 565-570, February 2001

[3] Julia Khandurina, Timothy E. McKnight, Stephen C. Jacobson, Larry C. Waters, Robert S. Foote, and J. Michael Ramsey, "Integrated System for Rapid PCR-Based DNA Analysis in Microfluidic Devices," Anal. Chem., vol. 72, pp. 2995-3000, July 2000.

[4] J. El-Ali, I. R. Perch-Nielsen, C. R. Poulsen, D. D. Bang, P. Telleman, A. Wolff, "Simulation and experimental validation of a SU-8 based PCR thermocycler chip with integrated heaters and temperature sensor," Sensors and Actuators A, vol. 110, pp. 3-10, 2004

[5] Chia-Sheng Liao, Gwo-Bin Lee, Jiunn-Jong Wu, Chih-Ching Chang, Tsung-Min Hsieh, Fu-Chun Huang, and Ching-Hsing Luo, "Micromachined polymerase chain reaction system for multiple DNA amplification of upper respiratory tract infectious diseases," Biosensors and Bioelectronics, vol. 20, pp. 1341-1348, 2005.

[6] Cathy Ke, Ann-Marie Kelleher, Helen Berney, Michelle Sheehan, Alan Mathewson, "Single step cell lysis/PCR detection of *Escherichia coli* in an independently controllable silicon microreactor," Sensors and Actuators B, vol. 120, pp. 538-544, 2007.

[7] Shantanu Bhattacharya, Shuaib Salamat, Dallas Morisette, Padmapriya Banada, Demir Akin, yl-Shao Liu, Arun K. Bhunia, Michael Ladisch, and Rashid Bashir, "PCR-based detection in a micro-fabricated platform," Lab Chip, vol. 8, pp. 1130-1136, 2008.

[8] Adam T. Woolley, Dean Hadley, Phoebe Landre, Andrew J. deMello, Richard A. Mathies, and M. Allen Northrup, "Functional Integration of PCR Amplification and Capillary Electrophoresis in a Microfabricated DNA Analysis Device," Anal. Chem., vol. 68, pp. 4081-4086, December 1996

[9] Larry C. Waters, Stephen C. Jacobson, Natalia Kroutchinina, Julia Khandurina, Robert S. Foote, and J. Michael Ramsey, "Multiple Sample PCR Amplification and Electrophoretic Analysis on a Microchip," Anal. Chem., vol. 70, pp. 5172-5176, 1998.

[10] Fu-Chun Huang, Chia-Sheng Liao, Gwo-Bin Lee, "An integrated microfluidic chip for DNA/RNA amplification, electrophoresis separation and on-line optical detection," Electrophoresis, vol. 27, pp. 3297-3305, 2006.

[11] Nathaniel C. Cady, Scott Stelick, Madanagopal V. Kunnavakkam, Carl A. Batt, "Real-Time PCR detection of *Listeria monocytogenes* using and integrated microfluidics platform," Sensors and Actuators B, vol. 107, pp. 332-341, 2005.

[12] Jing Wang, Zongyuan Chen, Paul L. A. M. Corstjens, Michael G. Mauk and Haim H. Bau, "A disposable microfluidic cassette for DNA amplification and detection," vol. 6, pp. 46-53, 2006.

[13] yl-Shao Liu, Padmapriya P. Banada, Shantanu Bhattacharya, Arun K. Bhunia, and Rashid Bashir, "Electrical characterization of DNA molecules in solution using impedance measurements," Applied Physics Letters, vol. 92, 143902, 2008.

EXAMPLE 4

Droplet-Based Detection and System Characterization

Figure 12:
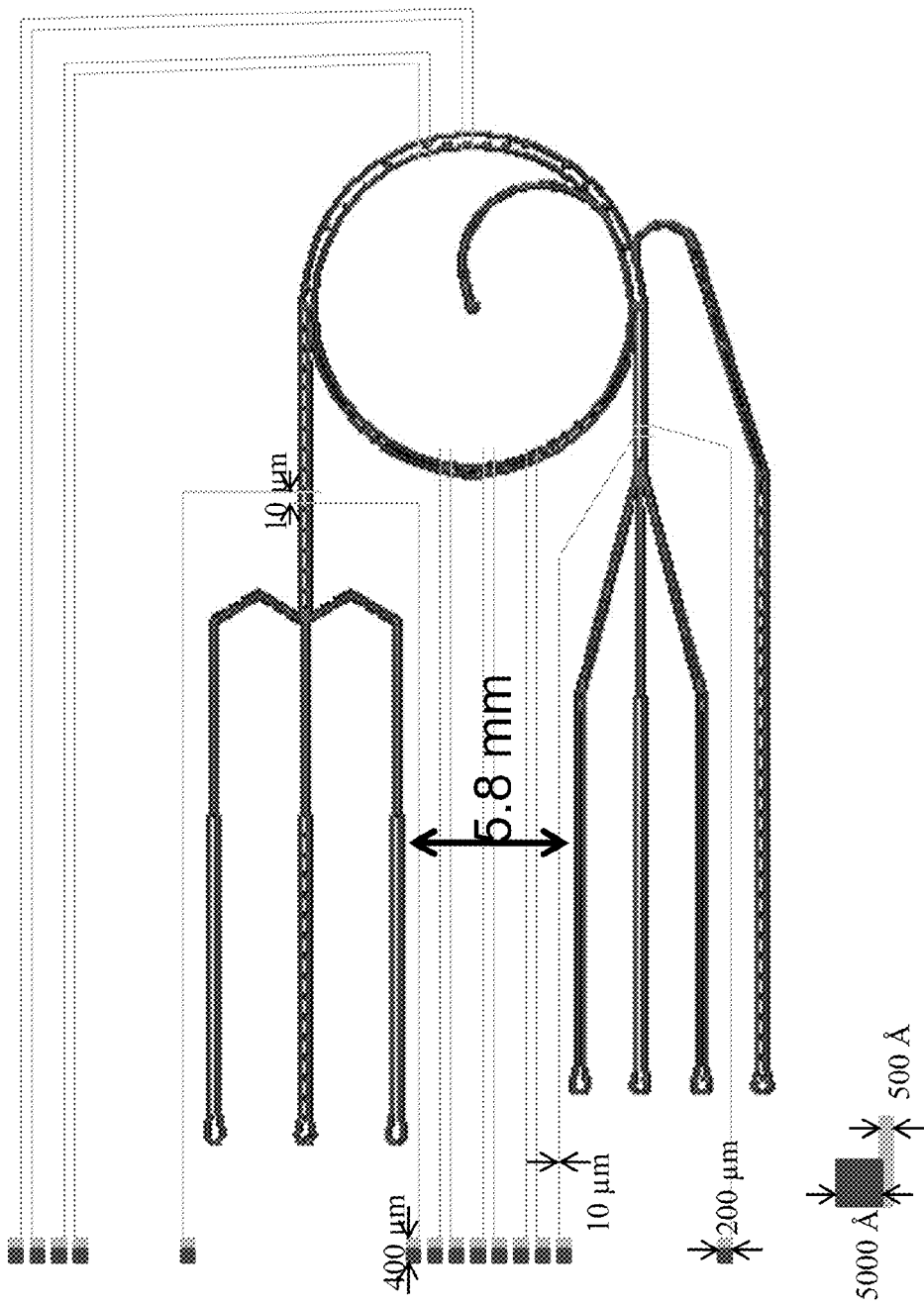
FIG. 12: Schematic illustration of a fluidic system for introducing droplets, PCR reagents, and surrounding media such as ionic liquid for electrical detection.
Figure 13:
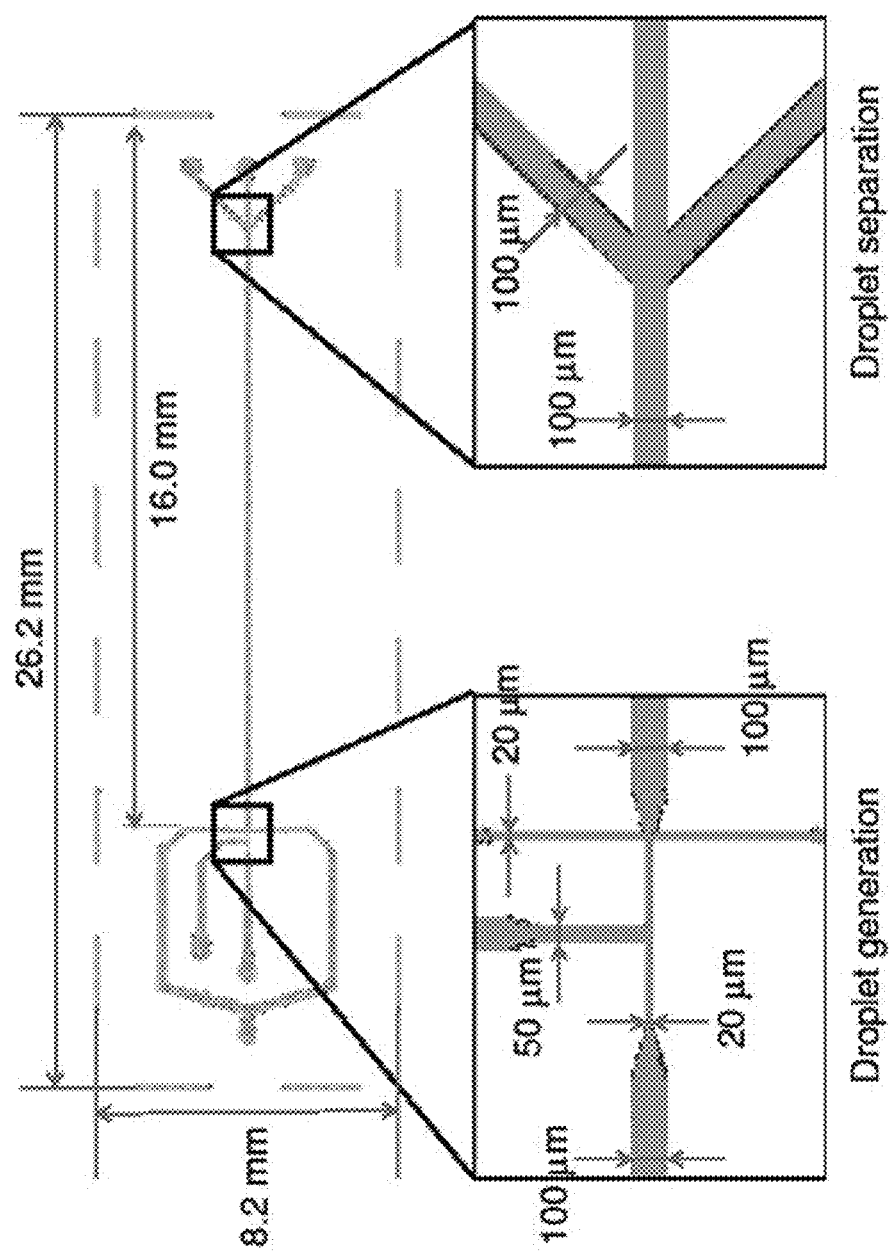
FIG. 13: Schematic illustration of a fluidic system for generating droplets and separating droplets, including droplets containing a to-be-detected PCR product.

Droplet-based PCR provides the ability to significantly increase the sensitivity and reliability of detection by confining the to-be-detected product within the droplet. In addition, fluidic control of the droplet provides the ability to customize the system depending on the experimental conditions, such as the product to be detected and sample concentration. Droplet-based detection is particularly useful because fluidic design and control makes droplet control convenient, precise and reliable. For example, the geometry of the conduit network can be varied to provide optimized droplet generation and PCR cycling. FIG. 12 illustrates one example of a conduit network having a variety of inflow conduits and geometry. Varying fluid properties at a convergence or a bifurcation, such as conduit geometry (e.g., diameters, convergence angle, etc.), fluid properties, and/or relative flow-rates provides the capacity to fine-tune the system to optimize detection sensitivity and accuracy. FIG. 13 illustrates various conduit geometry, such as diameters, taper, and inlet or outlet angle. Droplet control can be controlled at one or both of droplet generation (left panel) or droplet separation (right panel).

Figure 14:
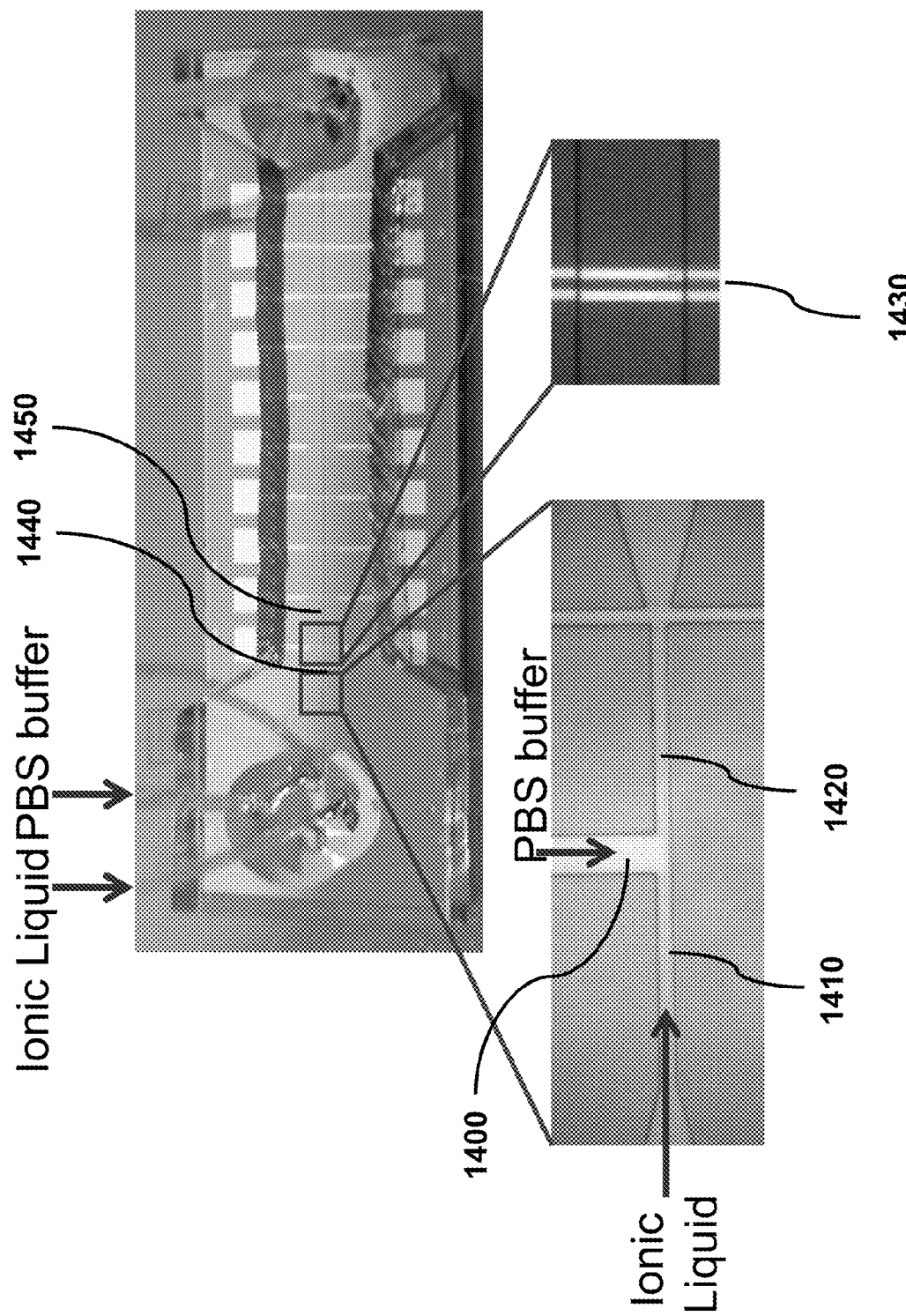
FIG. 14: Photograph of an experimental system to evaluate droplet generation, wherein the droplet comprises PBS (phosphate buffered saline) buffer surrounded by ionic liquid media. The top panel is the overall fluidic system. The bottom left panel is a close-up view of two inlet fluid feed parent conduits, one containing ionic liquid media and the other a PBS buffer, joining to form a collecting ("daughter") vessel to generate PBS droplets confined by a surrounding fluid comprising an ionic liquid. The bottom right panel is a close-up view of an electrode portion positioned along (e.g. on the surface) the collecting vessel in a perpendicular direction to the vessel's longitudinal axis of flow over which the flowing droplets pass.
Figure 16:
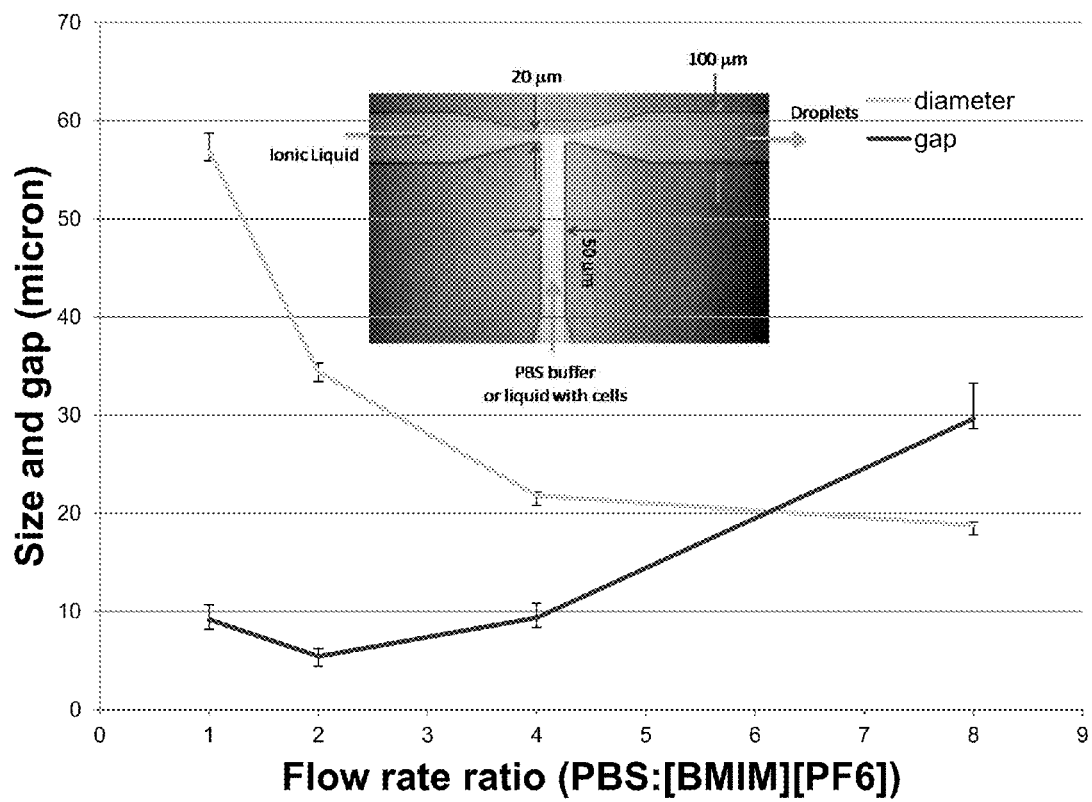
FIG. 16: Effect of flow-rate ratio of the feed vessels on droplet size ("diameter") and droplet spacing ("gap"). One feed vessel contains PBS (flow-rate varies from 0.2 μL/min to 0.025 μL/min) and the other feed vessel contains the ionic liquid [BMIM][PF$_6$] (0.2 μL/min) as illustrated by the inset photomicrograph.

An exemplary fluid conduit system is shown in FIG. 14. Sample inflow conduit 1400 introduces sample to the system, including to collecting conduit 1420, exemplified in this example as PBS buffer (or equivalently a sample to be tested, such as biological cells in PBS and PCR reagents relevant thereto), and a suspending fluid inflow conduit 1410 to provide a surrounding media, such as ionic liquid (IL), to collecting conduit 1420. In an aspect, the PCR cycling occurs after droplet formation. In an aspect different temperature zones (illustrated by 1440 and 1450) provide PCR or isothermal amplification to the droplet during flow. In an aspect, the droplet flow is stopped and thermal cycling occurs on a substantially stationary droplet or a plurality of stationary droplets. After the appropriate number of cycles, flow may be re-established to ensure droplets are electrically detected by the electrodes. Alternatively, PCR may occur upstream of droplet generation, with the amplified product confined in the droplet that then passes the electrodes for electrical detection. In this manner, flow need not be stopped, but instead the bulk amplified sample provided by an inlet conduit. Conduits 1400 and 1410 establish a flow of droplets containing PCR solution and sample surrounded by suspending media that flows along collecting conduit 1420. Flow rates and relative inlet flow ratios are selectably adjusted by controlling flow-rates in one or both inlet flow vessels, such as by a microfluidic pump or pressure control. Collecting conduit 1420 transports droplets to electrodes that are in fluidly connected to the collecting conduit (e.g., physically contacting fluid in the collecting conduit), such as electrode array 1430 that measures a droplet electrical parameter, such as electric potential or other parameter that can be used to calculate or measure the droplet electric impedance. In an aspect, the electrode array comprises at least one pair of parallel electrode strips oriented orthogonal to the droplet flow direction, as illustrated in FIG. 14 (lower left photograph). In an aspect, the opposed electrodes are separated by a separation distance that is within 50%, within 25% or is within 10% the average diameter of the droplet. As desired, other electrode geometries are employed, including more than two electrodes or the interdigitated electrodes described herein. In an aspect, the conduits are channels having a rectangular cross-section, a square cross-section, a circular cross-section, or an elliptical cross-section. In an aspect, the cross-sectional shape and/or area varies with position along the conduit, such as being tapered (see, e.g., inset of FIG. 16).

Figure 15:
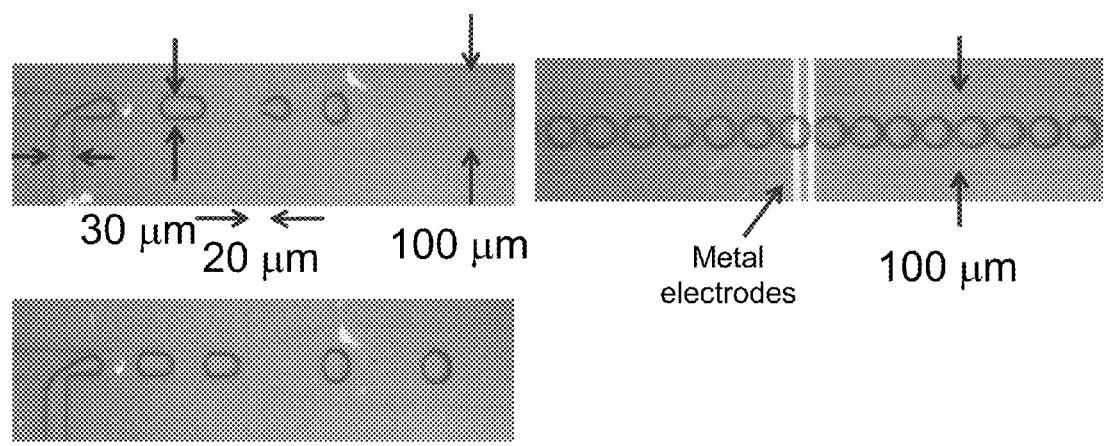
FIG. 15: Photographs of the generation of PBS droplets in viscous fluids from two parent feed vessels joining to form a single collecting vessel. Various physical parameters impact the size and/or spacing of the droplets.

FIG. 15 is a photomicrograph of PBS droplet generation in a viscous fluid. In an embodiment, any of the methods and devices provided herein relate to droplet generation, wherein one or more of droplet size, velocity, spacing are controlled. Various dimensionless parameters may be used to select appropriate physical conditions to obtain desired droplet properties. For example, the Weber Number (We) is used to parameterize droplet breakup processes, where inertial and capillary pressure are more important than viscous stresses:

$$We=\rho v^2 I/\sigma$$

where $\rho$ is the fluid density, v, is fluid velocity, I is droplet diameter, and $\sigma$ surface tension.

Another relevant dimensionless parameter is the Capillary number (Ca), and can be more important than We for characterizing droplet formation in microfluidic device:

$$Ca=\mu v/\gamma,$$

where $\mu$ is the viscosity of the media surrounding the droplet (e.g., oil), v is the velocity of the bulk flow rate, and $\gamma$ the interfacial tension between the droplet and the media surrounding the droplet.

In an aspect, any of the methods provided herein relate droplet formation and the use of an ionic liquid outside of droplets to improve electrical measurements and signal to noise ratio. One example of droplet generation control is provided in FIG. 16. In an embodiment, the droplet generation is by controlling the ratio of inlet flows (e.g., ratio of the inlet droplet-material flow-rate to inlet droplet surrounding media flow-rate), Other flow parameters relevant to control of droplet generation include, but are not limited to, total flow rate, bifurcation angle between inlet vessels and/or collecting vessel, fluid density, fluid viscosity, vessel dimension (e.g., diameter, characteristic width or height for non-circular conduits), Reynolds number). In an aspect, any of the methods provided herein relate to controlling a droplet parameter such as droplet diameter, volume or spacing, by varying one or more flow parameters, such as illustrated by the effect of inlet flow ratio on droplet size and gap illustrated in FIG. 16.

Figures 17A, 17B:
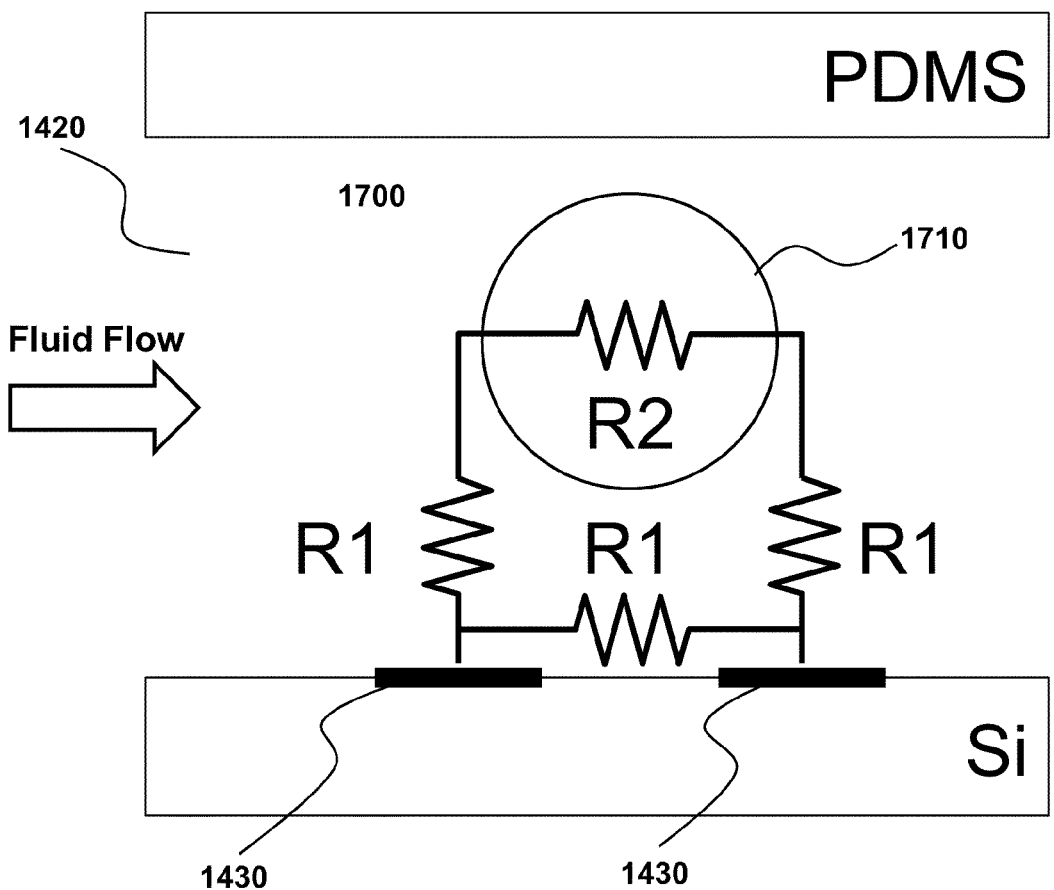
FIG. 17A: Schematic of electrical measurement of flowing droplets surrounded by ionic liquid by electrode array.
FIG. 17B is a table summarizing the calculated electrical resistivity of various fluids.

A schematic of the electrical measurement of droplets in a conduit is provided in FIG. 17A (with further reference to FIG. 14). The arrow indicates the direction of fluid flow of suspending fluid 1700 and droplet 1710 along collecting conduit 1420. A pair of electrodes form electrode array 1430 that are configured to detect an electrical parameter of droplet 1710 as it passes the array. This embodiment may be further incorporated into any of the other biochips provided herein, such as in FIG. 2 at the genomic detection portion (e.g., the droplet corresponds to the confined region). FIG. 14 shows sample inflow conduit 1400 and suspending fluid inflow conduit 1410 fluidly connected to collecting conduit 1420 for generating a confined volume that is a droplet. The droplet may comprise an aqueous solution such as PCR solution. In an aspect, the electrical parameter is measured for a droplet 1710 (in this example PBS) surrounded by surrounding media 1700, such as ionic liquid immiscible with the droplet, by an electrode array 1720, in this example a pair of electrodes, so that dielectric capacitance of the droplet is measured, thereby detecting PCR product in the droplet. In an aspect, three electrodes are used. In an aspect, more than three electrodes are used. In an aspect, the droplet is surrounded by an IL, as experimental results indicate it is difficult to detect droplets surrounded by low-ionic solution such as mineral oil. In particular, no significant variation in voltage during flow of the systems summarized in FIGS. 18-19 is detected, suggesting droplets suspended in a suspending fluid that is oil are not ideal. Accordingly, an IL that is [bmim]$PF_6$ is used to surround the droplet. Other exemplary IL are summarized in FIG. 20. FIG. 21 is a plot of voltage as a function of time for flowing droplets (FIG. 21) and plugs (FIG. 22). Accordingly, an aspect of any of the methods provided herein relates to detecting PCR product in a droplet that is surrounded by a suspending fluid or media that is an ionic liquid.

Figure 23A:
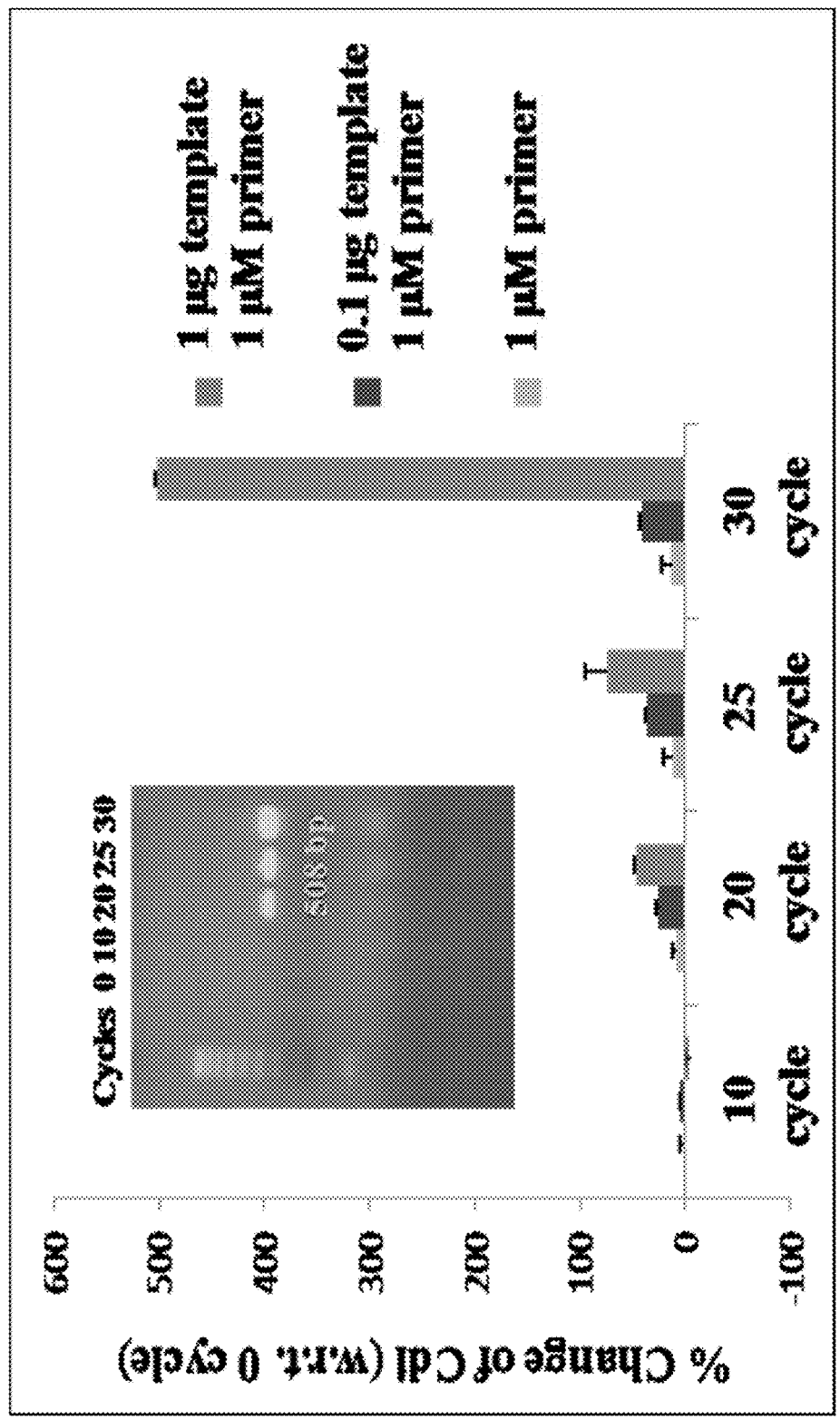
FIG. 23A: Detection of *L. monocytogenes* The dielectric capacitance of the solution is plotted as a function of PCR cycle number for three different conditions of template amount and primer concentration. The electrically-detected results are confirmed with gel electrophoresis as indicated by the gel diagram.
Figure 23B:
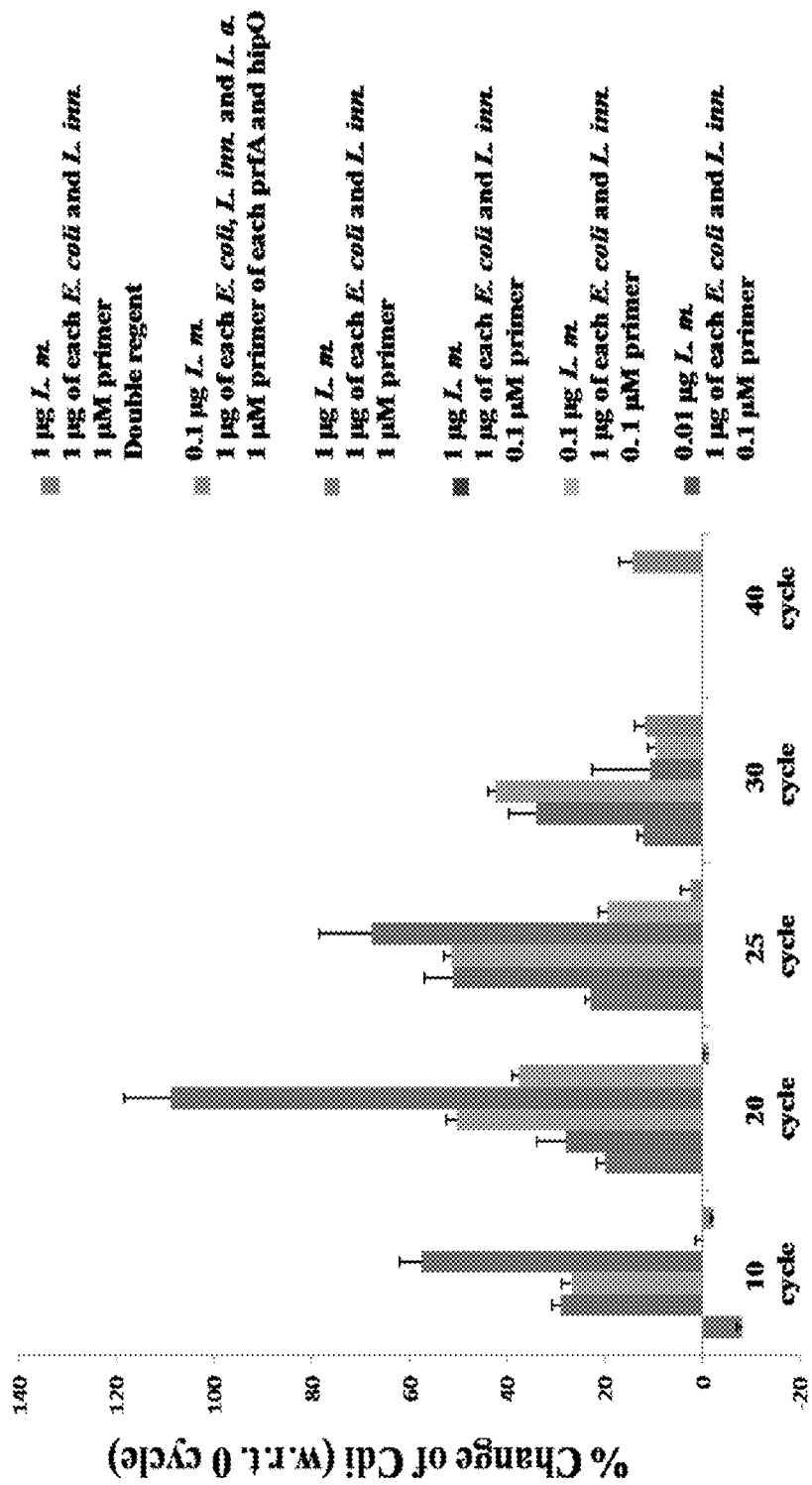
FIG. 23B: The dielectric capacitance of the solution is plotted as a function of PCR cycle number for various conditions of template amount, primer concentration, and cell concentration (of *L. monocytogenes, E. coli* and *L. inn*).
Figure 23C:
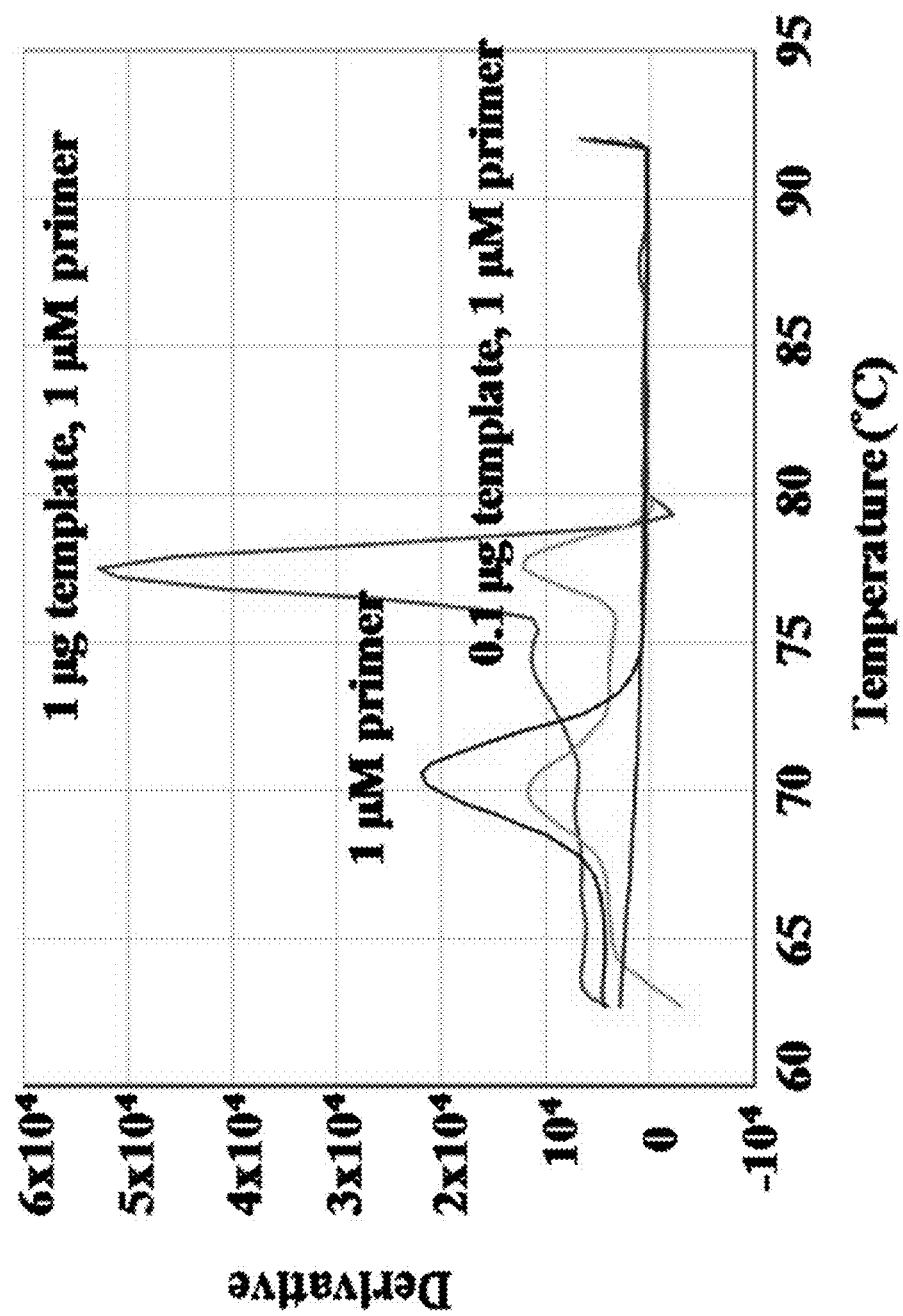
FIG. 23C is a plot of derivative amount as a function of temperature for various experimental conditions (e.g., template and/or primer concentrations). The experimental conditions include prfA 508 by segment target for specific detection of *Listeria monocytogenes* with primers as provided in SEQ ID NOs:5-6. The sample is PCR mix plus DNA template and the control is PCR mix only.
Figure 25:
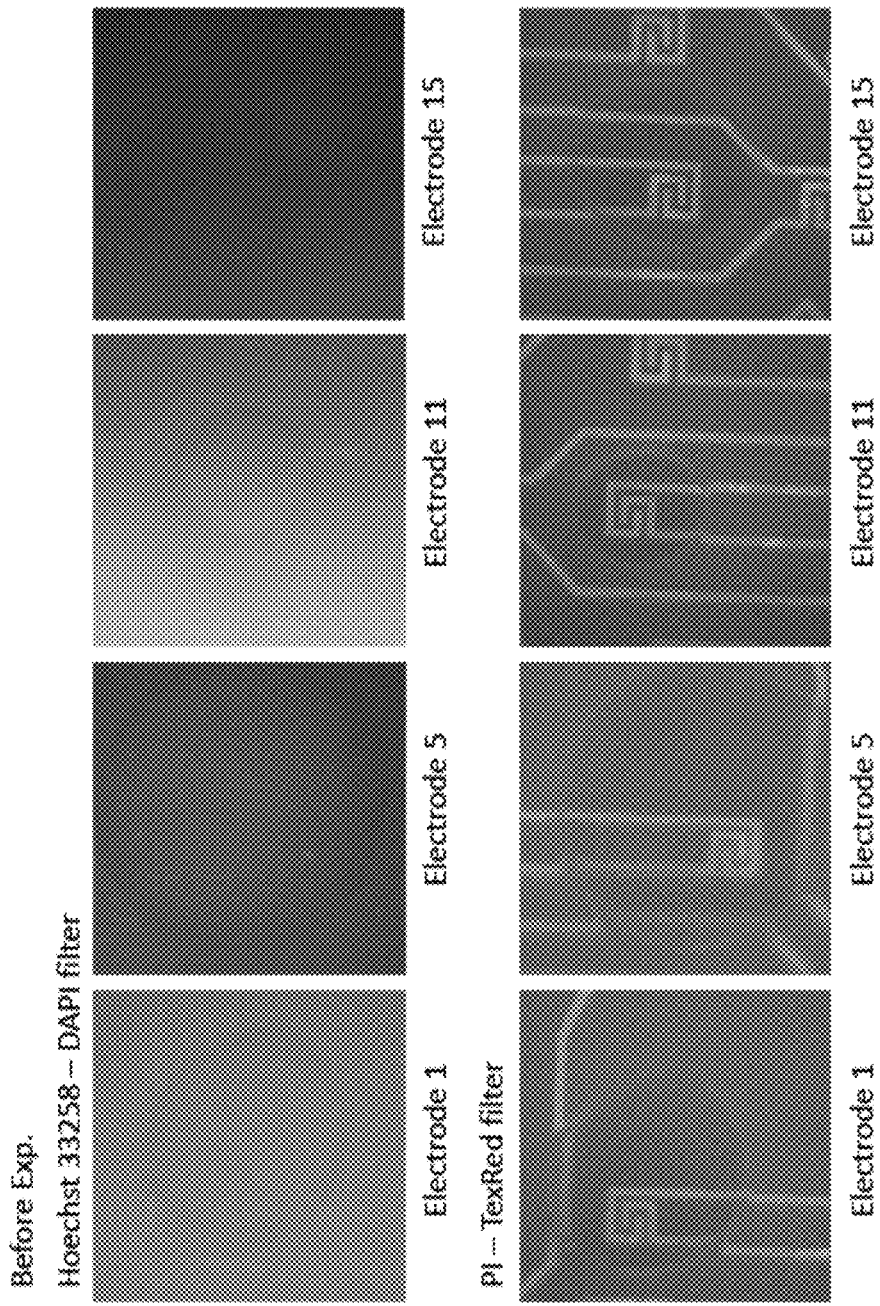
FIG. 25: Photographs of droplet position for various electrodes in a fluidic system. The top panels relate to an optical DAPI filter to optically detect Hoechst 33258; the bottom panels use a TexRed filter to optically detect PI (propidium iodide). The photographs are before exposure to appropriate wavelength to excite the dyes.
Figure 26:
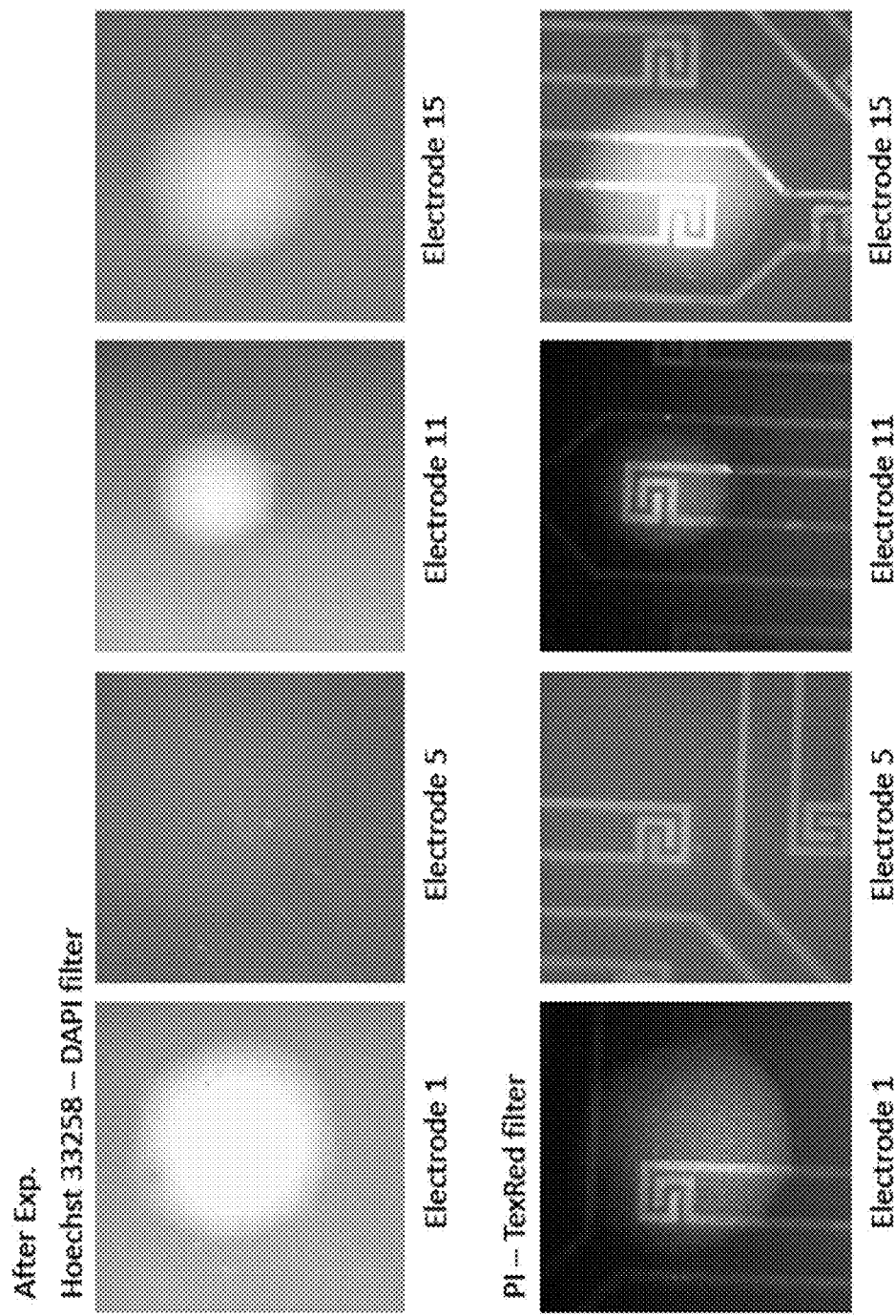
FIG. 26: Photographs of droplet position for various electrodes in a fluidic system. The top panels relate to an optical DAPI filter to optically detect Hoechst 33258; the bottom panels use a TexRed filter to optically detect PI (propidium iodide). The droplets are exposed to appropriate wavelengths to excite the dyes, indicating that in three of the four electrode systems, significant biologic material is confined in the droplet.
Figure 27:
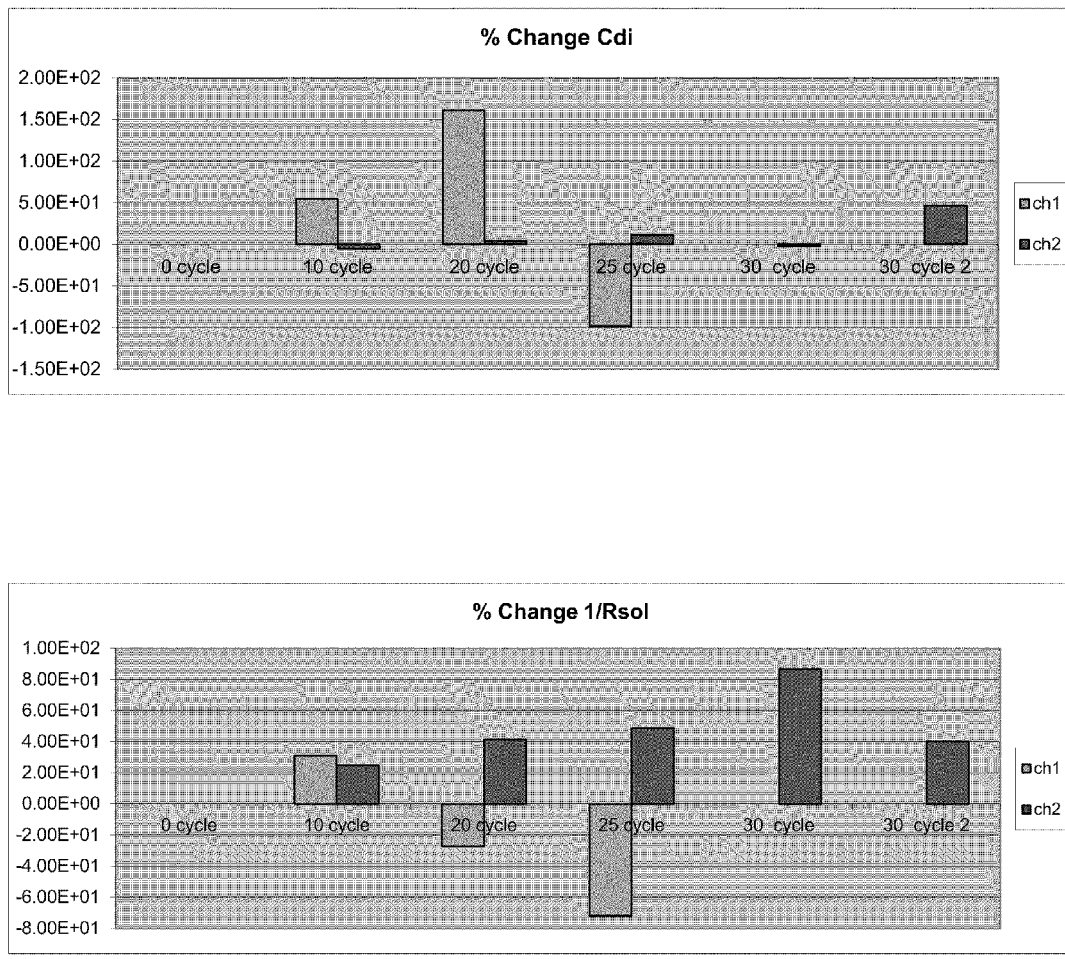
FIG. 27: Plot of percentage change in Cdi as a function of number of PCR cycles for two channels. The bottom panel is a plot of resistivity as a function of number of PCR cycles for two channels.

Various label-free detection of PCR product by a method of the present invention is provided in FIG. 23A-23C. FIG. 24 demonstrates the PCR amplification can be confined to a droplet. Those droplets may be introduced to an electrode, either in a stationary condition or under flow. FIGS. 25-26 illustrate the droplet positioned near an electrode, such as the electrode pairs having a geometry in FIGS. 25-26. The droplets contain approximately 170 cells, based on the concentration of the cells in the solution from which the droplet is formed and the size of droplet (assuming a sphere of diameter 150 μm and $3\times10^8$ cells/mL).

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a volume or size range, temperature range, a length range, a time range, a velocity, a pressure or rates thereof, a composition, or a concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

TABLE 1

Summary of Sequences

| SEQ ID NO: | Description | Sequence | Type |
|---|---|---|---|
| 1 | MAV primer set specific to M. avium (sense) | CCT CAA GAC GCA TGT CTT CT | DNA |
| 2 | MAV primer set specific to M. avium (anti-sense) | ACA GCT CCC TCC CAA AAG GG | DNA |
| 3 | universal primer set, MYCOB (sense) | ATG CAA GTC GAA CGG AAA GG | DNA |
| 4 | universal primer set, MYCOB (anti-sense) | TGC ACA CAG GCC ACA AGG GA | DNA |
| 5 | primer for PCR reaction targeted on L. monocytogenes prfA genes (5' to 3') | CGGGATAAAACCAAAACAATTT | DNA |
| 6 | primer for PCR reaction targeted on L. monocytogenes prfA genes (5' to 3') | TGAGCTATGTGCGATGCCACTT | DNA |

We claim:

1. A method of detecting a nucleic acid amplification product in solution, said method comprising:

providing a microfluidic amplification chamber comprising an electrode array on at least one surface of said microfluidic amplification chamber;

introducing a solution that may contain a template to be amplified by nucleic acid amplification in said microfluidic amplification chamber;

performing a nucleic acid amplification on said solution, wherein said nucleic acid amplification is performed in a confined region or said nucleic acid amplification product is contained in a confined region, to generate an amplified nucleic acid amplification product in solution, wherein said confined region has a volume selected from a range that is greater than or equal to 0.5 pL and less than or equal to 1 nL;

applying an electric potential to said electrode array to produce an electric field in said confined region; and measuring an electrical parameter of said solution in said confined region, wherein said electrical parameter is solution impedance, thereby detecting said nucleic acid amplification product in solution;

wherein said step of introducing the solution comprises:
providing a droplet of the solution surrounded by a suspending fluid comprising an ionic liquid, and the droplet corresponds to the confined region; and
electrically contacting the droplet with the electrode array;
wherein said detection of nucleic acid amplification is label-free.

2. The method of claim 1, wherein said confined region has a volume that is less than or equal to:
1 pL for detecting said nucleic acid amplification product from a bacterial cell; and
10 pL for detecting said nucleic acid amplification product from a mammalian cell.

3. The method of claim 1, wherein said electrode array is positioned on one surface of said microfluidic amplification chamber.

4. The method of claim 1, wherein said electrode array comprises an interdigitated array of electrodes having a width selected from a range that is greater than or equal to 10 nm and less than or equal to 100 pm and a separation distance between adjacent electrodes selected from a range that is greater than or equal to 10 nm and less than or equal to 100 μm.

5. The method of claim 1, wherein said microfluidic amplification chamber comprises side walls formed of PDMS and a bottom surface of $SiO_2$, wherein said bottom surface supports said electrode array.

6. The method of claim 1, wherein said microfluidic amplification chamber is controllably isolated by one or more fluid control valves.

7. The method of claim 6, wherein said fluid control valve is operably connected to a reservoir containing said solution for performing nucleic acid amplification or to a reservoir containing said solution that may contain template to be amplified by nucleic acid amplification reaction.

8. The method of claim 1, wherein said confined region has a minimum concentration of template in said confined region that is greater than or equal to 10 template molecules per pico liter of volume.

9. The method of claim 1, wherein said method has a detection limit of as low as 0.1 μg DNA templates in said confined volume.

10. The method of claim 1, wherein said detecting is performed continuously or after each nucleic acid amplification cycle.

11. The method of claim 10, wherein said nucleic acid amplification is by polymerase chain reaction (PCR) and said detecting is capable of resolving a PCR product concentration difference between consecutive PCR cycles.

12. The method of claim 11, wherein said consecutive cycle is for a PCR cycle number that is selected from a range that is greater than or equal to 4 and less than or equal to 9.

13. The method of claim 1, wherein said nucleic acid amplification is performed on a sample for which the detection comprises a presence or an absence of said nucleic acid amplification product.

14. The method of claim 13, wherein said sample comprises one or more target cells, said method further comprising lysing said target cells and contacting said lysate with said solution.

15. The method of claim 14 wherein said nucleic acid amplification product is a contiguous sequence of bacterial DNA.

16. The method of claim 14, wherein said target cells comprise a plurality cell populations, and said method is for detecting a food-borne pathogen.

17. The method of claim 1, wherein said ionic liquid is a hydrophobic liquid that is immiscible with an aqueous solution.

18. The method of claim 17, further comprising the step of:
introducing the suspending fluid to a collecting conduit at a suspending fluid flow-rate;
introducing the solution to the collecting conduit at a solution flow rate; and
forming the droplet having a user-selected droplet volume or droplet spacing by adjusting an inlet flow ratio, said inlet flow ratio corresponding to the ratio of suspending fluid flow-rate to solution flow-rate.

19. The method of claim 18, wherein the formed droplet flows past said electrode array and said measured electrical parameter is a dielectric capacitance of said droplet.

20. The method of claim 1, wherein said detection has a sensitivity that is as low as 1 template molecule/ 10 pL.

21. The method of claim 1, wherein said microfluidic amplification chamber has a volume that is selected from a range of 10 μL to 150 μL.

22. The method of claim 1, wherein prior to said nucleic acid amplification step, said solution comprises DNA having a concentration that is selected from a range that is greater than or equal to $5*10^8$ DNA molecules/μL and less than or equal to $10^{10}$ DNA molecules/μL.

23. The method of claim 1, wherein said nucleic acid amplification product is DNA or RNA.

24. The method of claim 23, wherein said nucleic acid amplification product is DNA having a length that is selected from a range that is greater than or equal to 50 base pairs and less than or equal to 5000 base pairs.

25. The method of claim 1, wherein said detection is performed in a point-of-care detection assay.

26. The method of claim 1, further comprising identifying the presence or absence of nucleic acid amplification product.

27. The method of claim 1, further comprising determining the concentration of the nucleic acid amplification product or the number of nucleic acid amplification product.

28. The method of claim 1, wherein the nucleic acid amplification comprises isothermal amplification of RNA.

29. The method of claim 1, wherein the detection of said nucleic acid amplification product is for the presence or absence of a pathogen or a genetic defect that predisposes an individual to a disease state.

30. The method of claim 29, wherein the pathogen is a bacterial cell selected from the group consisting of: *Listeria moncytogenes; Escherichia coli; Campylobacter jejune; Listeria innocua;* and *Lactobacillus acidophilus.*

31. A method of detecting a nucleic acid amplification product in solution from a sample, said method comprising:
obtaining a sample comprising cells;
introducing said sample to an integrated biochip, wherein said integrated biochip comprises a microfluidic amplification chamber having an electrode array on one or more surfaces of said microfluidic amplification chamber, and performing the following steps on said integrated biochip:
concentrating said cells;
lysing said cells to obtain a lysate;
introducing to said microfluidic chamber said lysate and a solution for performing a nucleic acid amplification on a template in said lysate, thereby forming a nucleic acid amplification solution, wherein said nucleic acid amplification is a droplet surrounded by a suspending fluid comprising an ionic fluid;

performing a nucleic acid amplification on said droplet, wherein said nucleic acid amplification is performed in a confined region corresponding to said droplet to generate from said template an amplified nucleic acid amplification product in said droplet, wherein said confined region has a volume that is less than 1 nL applying an electric potential to said electrode array to produce an electric field in said confined region; and measuring an electrical parameter of said nucleic acid amplification solution in said confined region, wherein said electrical parameter is solution impedance, thereby detecting said nucleic acid amplification product in solution;

wherein said detection of nucleic acid amplification is label-free.

32. The method of claim 31, further comprising growing said cells in said integrated biochip, thereby increasing the number of cells in said integrated biochip.

33. The method of claim 31 wherein said confined region has a volume that is less than or equal to 100 pL.

34. The method of claim 31, wherein said concentrating step is by dielectrophoresis, antibody-based capture, cell culturing, or any combination thereof.

35. The method of claim 31, wherein said lysing step is by heating.

36. The method of claim 17, wherein said ionic liquid is an immidazolium-based ionic liquid of formula:

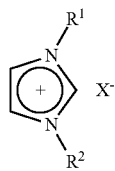

wherein R1 and R2 are independently selected to be H or alkyl; and

X is selected from the group consisting of: Cl$^-$/AlCl$_3$, PF$_6$, BF$_4$, Cl, Br, I,NO$_3$, [SO$_4$]$_2$; and (CF$_3$SO$_2$)$_2$N.

37. The method of claim 1, further comprising the step of applying a hydrophobic surface coating to a surface of said microfluidic amplification chamber to increase droplet stability throughout the thermocycling process.

38. The method of claim 37, wherein said hydrophobic surface coating comprises trichloro-perfluorooctyl-silane.

39. The method of claim 1, wherein said nucleic acid amplification is by PCR.

40. The method of claim 1, wherein said microfluidic amplification chamber comprises:

a collecting conduit fluidically connected to the electrode array;

a sample inflow conduit that provides the solution to the collecting conduit; and a suspending fluid inflow conduit that provides the surrounding media comprising an ionic liquid to the conduit, wherein the surrounding media in the collecting conduit surrounds the solution in the collecting conduit to form the droplet of solution.

41. The method of claim 31, wherein said microfluidic amplification chamber comprises:

a collecting conduit fluidically connected to the electrode array;

a sample inflow conduit that provides the solution to the collecting conduit; and a suspending fluid inflow conduit that provides the surrounding media comprising an ionic liquid to the conduit, wherein the surrounding media in the collecting conduit surrounds the solution in the collecting conduit to form the droplet of solution.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:

```
<223> OTHER INFORMATION: synthetic construct

<400> SEQUENCE: 1
cctcaagacg catgtcttct                                              20

<210> SEQ ID NO 2
<211> LENGTH: 20
<212> TYPE: DNA
<213> ORGANISM: Artificial Sequence
<220> FEATURE:
<223> OTHER INFORMATION: synthetic construct

<400> SEQUENCE: 2
acagctccct cccaaaaggg                                              20

<210> SEQ ID NO 3
<211> LENGTH: 20
<212> TYPE: DNA
<213> ORGANISM: Artificial Sequence
<220> FEATURE:
<223> OTHER INFORMATION: synthetic construct

<400> SEQUENCE: 3
atgcaagtcg aacggaaagg                                              20

<210> SEQ ID NO 4
<211> LENGTH: 20
<212> TYPE: DNA
<213> ORGANISM: Artificial Sequence
<220> FEATURE:
<223> OTHER INFORMATION: synthetic construct

<400> SEQUENCE: 4
tgcacacagg ccacaaggga                                              20

<210> SEQ ID NO 5
<211> LENGTH: 22
<212> TYPE: DNA
<213> ORGANISM: Artificial Sequence
<220> FEATURE:
<223> OTHER INFORMATION: synthetic construct

<400> SEQUENCE: 5
cgggataaaa ccaaaacaat tt                                           22

<210> SEQ ID NO 6
<211> LENGTH: 22
<212> TYPE: DNA
<213> ORGANISM: Artificial Sequence
<220> FEATURE:
<223> OTHER INFORMATION: synthetic construct

<400> SEQUENCE: 6
tgagctatgt gcgatgccac tt                                           22
```